United States Patent
Khanna

(10) Patent No.: US 9,468,703 B2
(45) Date of Patent: Oct. 18, 2016

(54) DECOMPRESSIVE CRANIOTOMY DEVICE AND METHODOLOGY

(76) Inventor: Rohit Khanna, Daytona Beach, FL (US)

(*) Notice: Subject to any disclaimer, the term of this patent is extended or adjusted under 35 U.S.C. 154(b) by 607 days.

(21) Appl. No.: 13/316,518

(22) Filed: Dec. 11, 2011

(65) Prior Publication Data

US 2012/0184999 A1     Jul. 19, 2012

Related U.S. Application Data

(60) Provisional application No. 61/422,640, filed on Dec. 13, 2010.

(51) Int. Cl.
| | | |
|---|---|---|
| *A61B 17/88* | (2006.01) | |
| *A61L 31/02* | (2006.01) | |
| *A61B 17/68* | (2006.01) | |
| *A61B 17/80* | (2006.01) | |
| *A61L 31/04* | (2006.01) | |
| *A61B 17/00* | (2006.01) | |

(52) U.S. Cl.
CPC ............ *A61L 31/022* (2013.01); *A61B 17/688* (2013.01); *A61B 17/8004* (2013.01); *A61B 17/8061* (2013.01); *A61L 31/04* (2013.01); *A61B 2017/00004* (2013.01); *A61B 2017/00862* (2013.01)

(58) Field of Classification Search
CPC ............ A61B 17/688; A61B 17/8004; A61B 17/8061; A61B 17/7055; A61B 17/80
USPC ........... 606/280–299, 70, 71, 903; 623/17.19
See application file for complete search history.

(56) References Cited

U.S. PATENT DOCUMENTS

| | | |
|---|---|---|
| 5,578,036 A | 11/1996 | Stone et al. |
| 5,707,373 A | 1/1998 | Sevrain et al. |
| 5,800,436 A | 9/1998 | Lerch |
| 5,902,304 A * | 5/1999 | Walker et al. ............ 606/71 |
| 5,916,200 A | 6/1999 | Eppley et al. |
| 5,916,217 A | 6/1999 | Manthrop et al. |
| 5,993,448 A | 11/1999 | Remmier |
| 6,093,188 A | 7/2000 | Murray |
| 6,187,004 B1 | 2/2001 | Fearon |
| 6,197,030 B1 * | 3/2001 | Pham ....................... 606/323 |
| 6,355,036 B1 | 3/2002 | Nakajima |
| 6,379,363 B1 | 4/2002 | Herrington et al. |
| 6,485,493 B1 | 11/2002 | Bremer |
| 6,585,739 B2 | 7/2003 | Kuras et al. |
| 6,685,707 B2 | 2/2004 | Roman et al. |
| 6,755,834 B2 | 6/2004 | Amis |
| 7,048,737 B2 | 5/2006 | Wellisz et al. |
| 7,361,178 B2 | 4/2008 | Hearn et al. |

(Continued)

FOREIGN PATENT DOCUMENTS

WO    WO-2012/082571 A2    6/2012

*Primary Examiner* — Kevin T Truong
*Assistant Examiner* — Si Ming Ku

(57) ABSTRACT

Certain embodiments of the present invention include a cranial fixation device for fixing a bone flap to the skull following a craniotomy. The device may accommodate variations in intracranial pressure without allowing the bone flap to move inward beyond the skull surface. Other embodiments include a method for cranial fixation. The method may include joining the bone flap to one portion of the fixation device and joining the skull to another portion of the fixation device. The method may also include responding to changes in intracranial pressure. The method may also include upward and downward movement of the fixation device and constraining the movement of the bone flap.

9 Claims, 88 Drawing Sheets

(56) References Cited

U.S. PATENT DOCUMENTS

| | | |
|---|---|---|
| 7,387,633 B2 | 6/2008 | Ahmad et al. |
| 7,867,262 B2 | 1/2011 | Morales et al. |
| 8,206,425 B2 | 6/2012 | Khanna |
| 2004/0172029 A1* | 9/2004 | Lerch ............................ 606/71 |
| 2005/0107813 A1 | 5/2005 | Garcia |
| 2007/0185489 A1 | 8/2007 | Abdou |
| 2007/0293865 A1 | 12/2007 | Ko |
| 2008/0154312 A1 | 6/2008 | Colleran et al. |
| 2008/0172097 A1* | 7/2008 | Lerch et al. ................. 606/324 |
| 2008/0200954 A1* | 8/2008 | Tucci ............................ 606/280 |
| 2008/0275555 A1* | 11/2008 | Makower et al. ......... 623/14.12 |
| 2011/0028972 A1 | 2/2011 | Khanna |
| 2011/0028973 A1 | 2/2011 | Khanna |
| 2011/0034959 A1* | 2/2011 | Sevrain et al. .............. 606/324 |
| 2012/0165879 A1 | 6/2012 | Khanna |
| 2012/0203284 A1 | 8/2012 | Khanna |

* cited by examiner

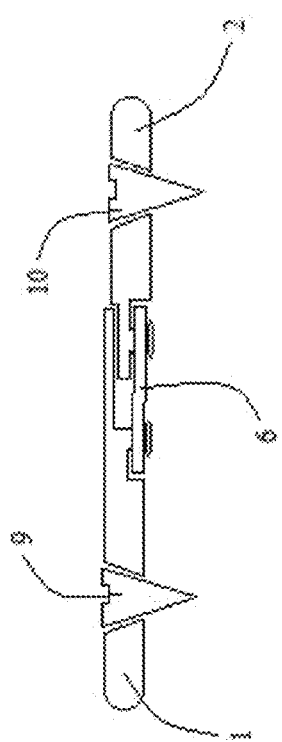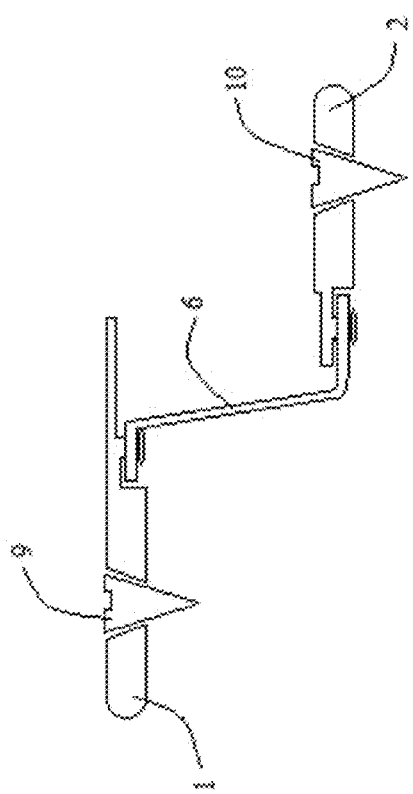

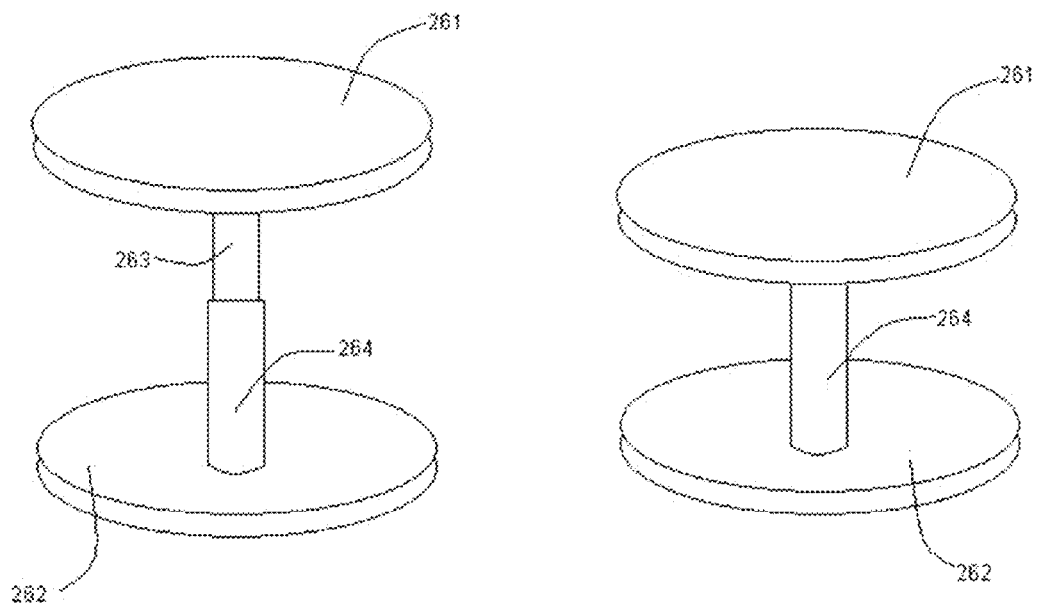
Fig. 97    Fig. 98
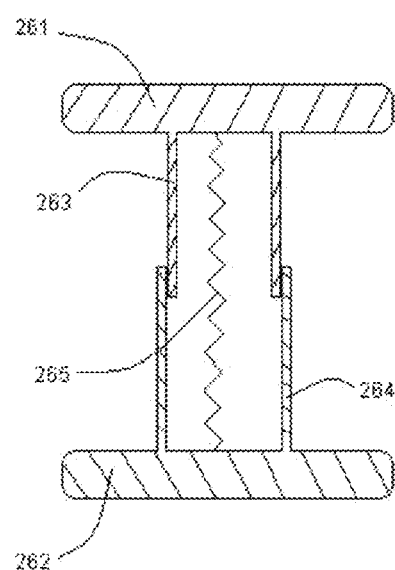 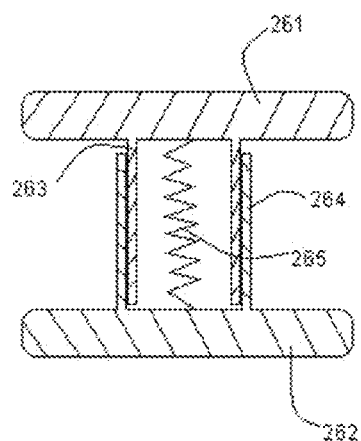
Fig. 99    Fig. 100

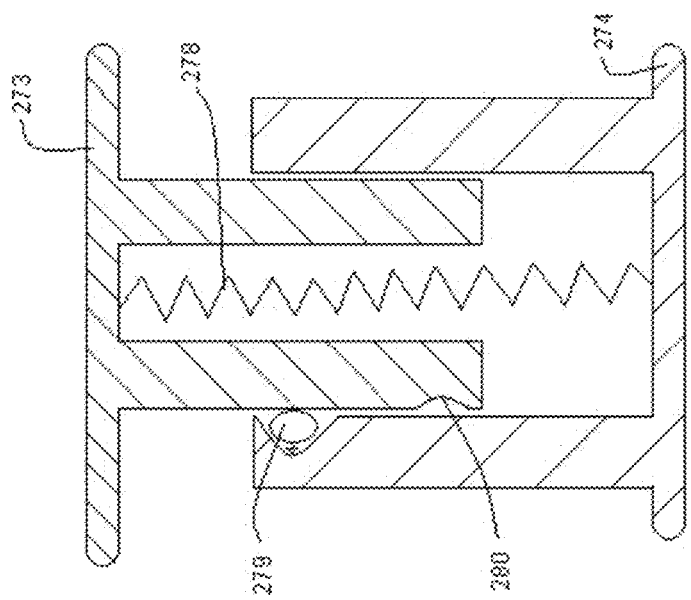
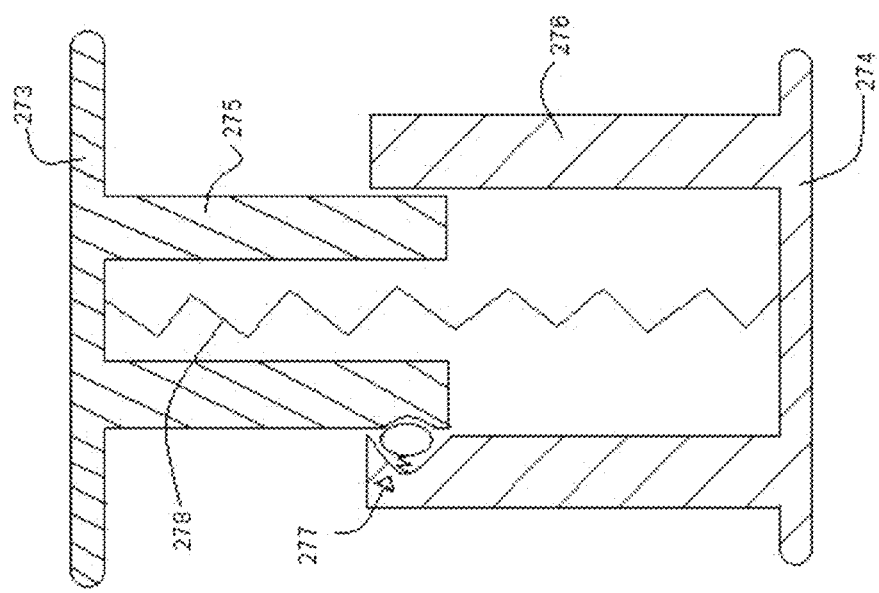

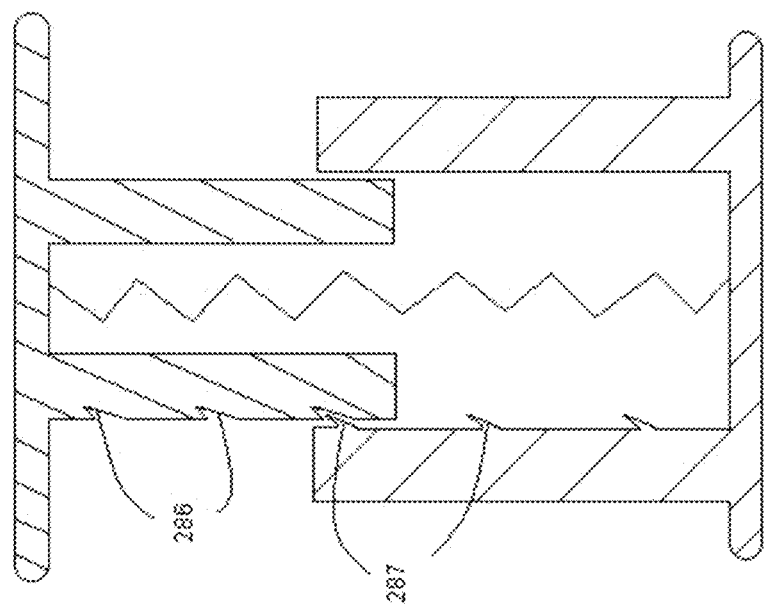
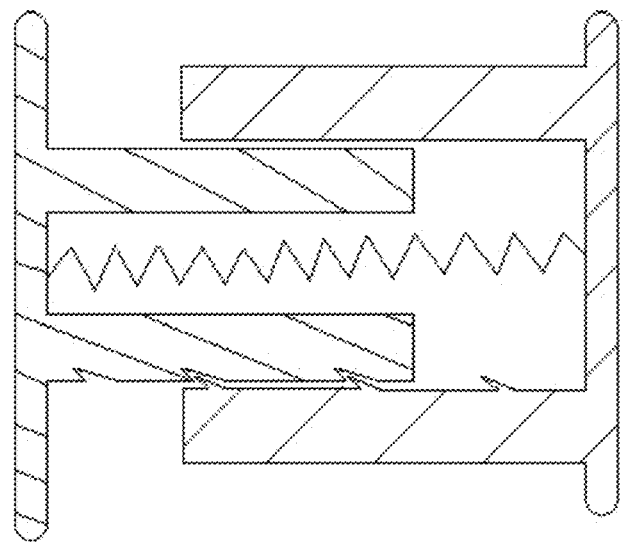

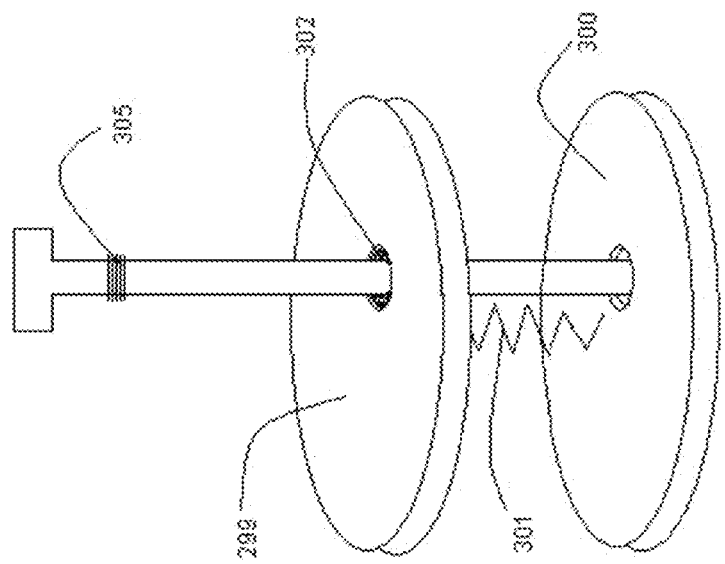
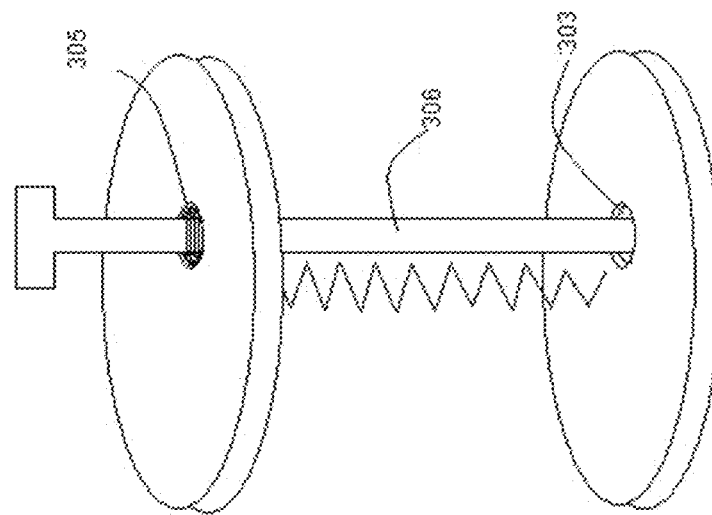

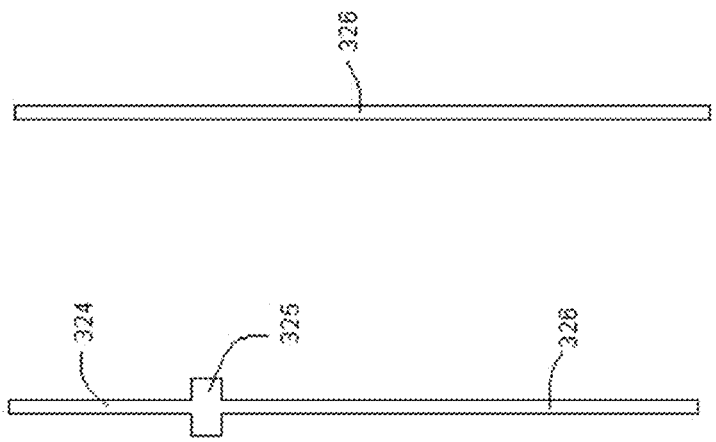
Fig. 135
Fig. 136
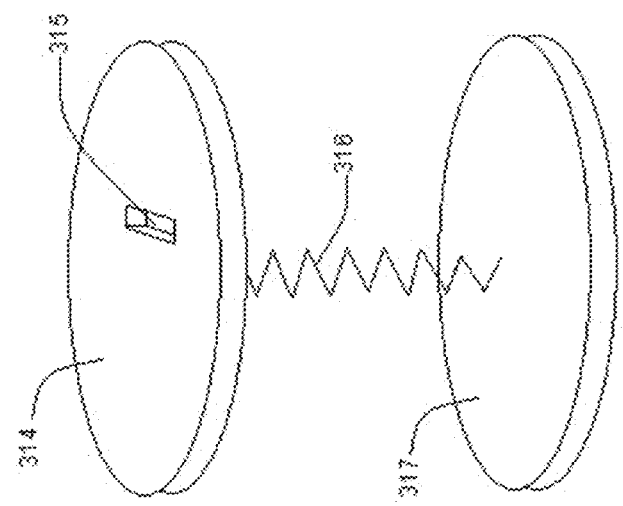
Fig. 134

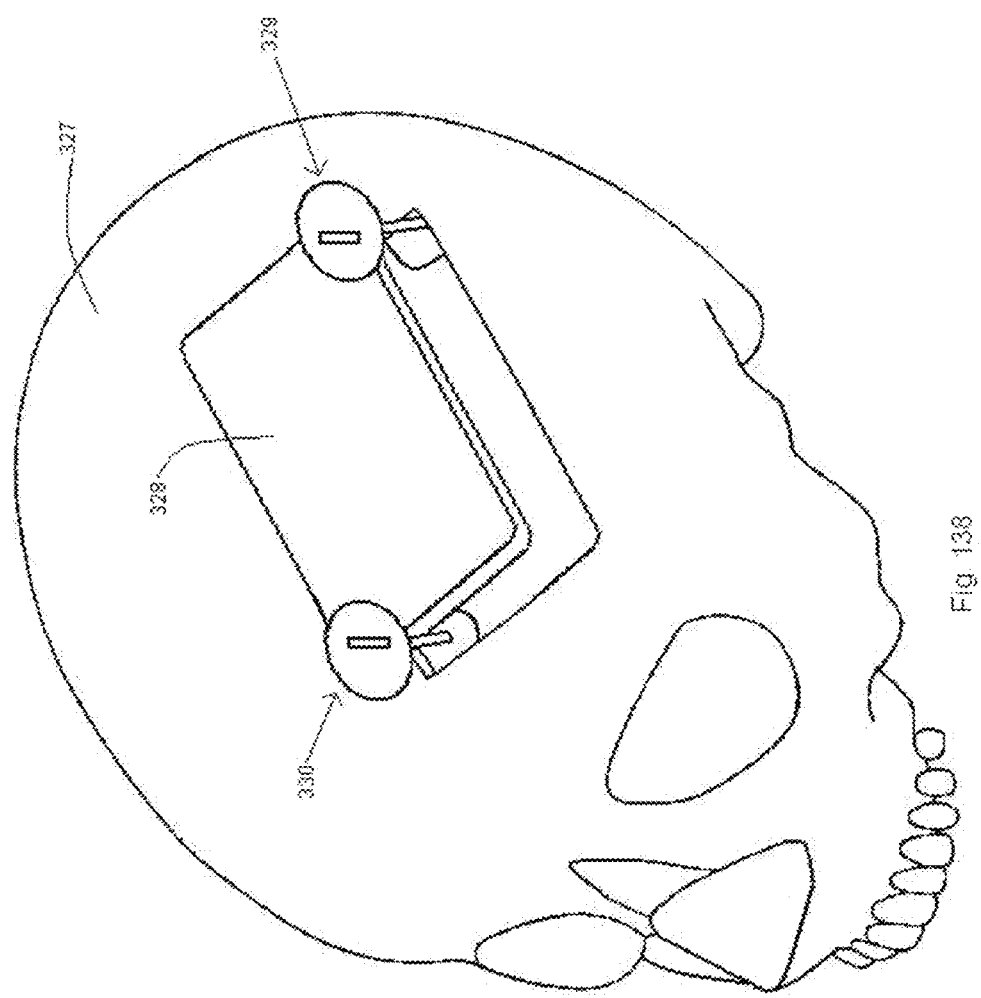

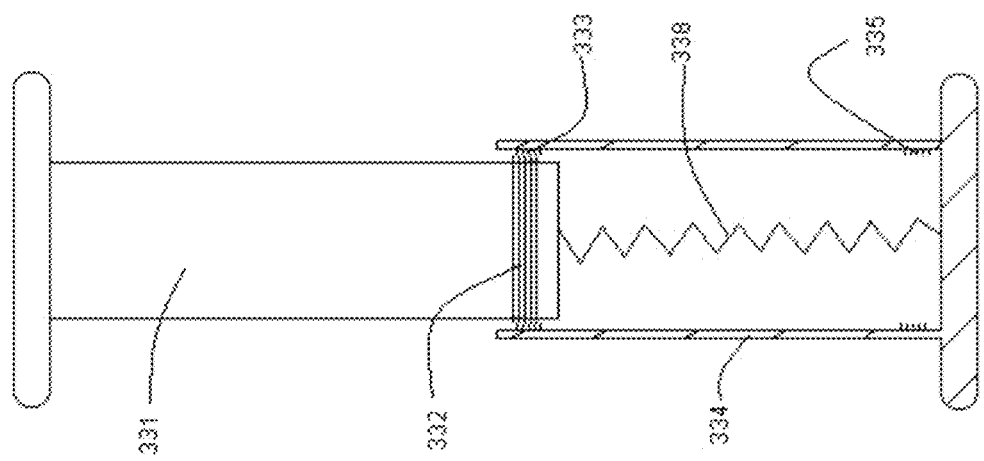
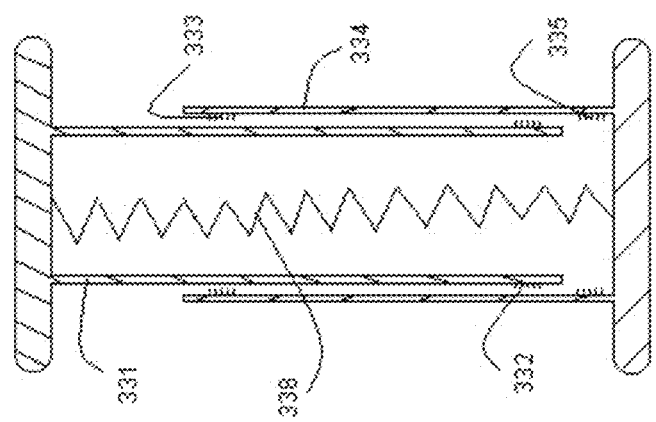

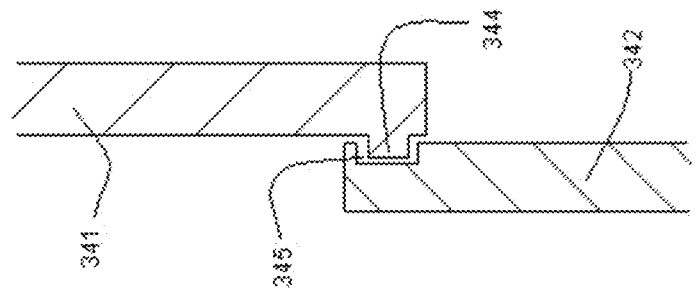
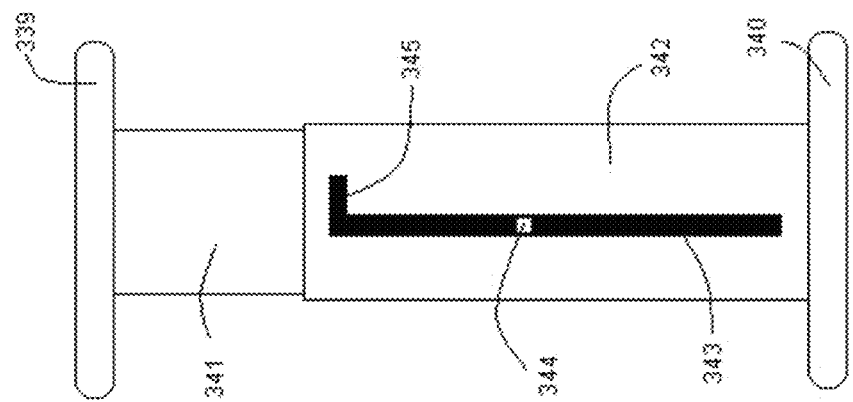
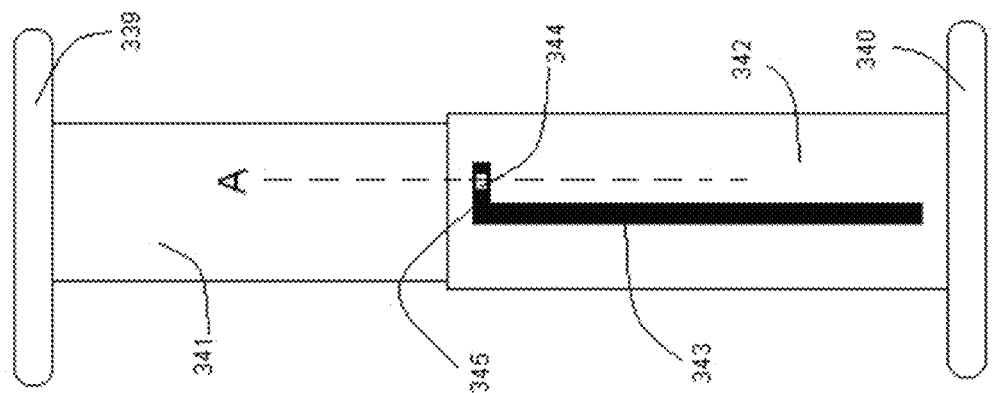

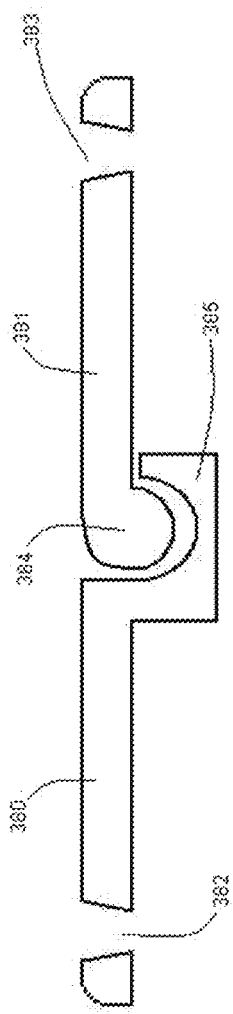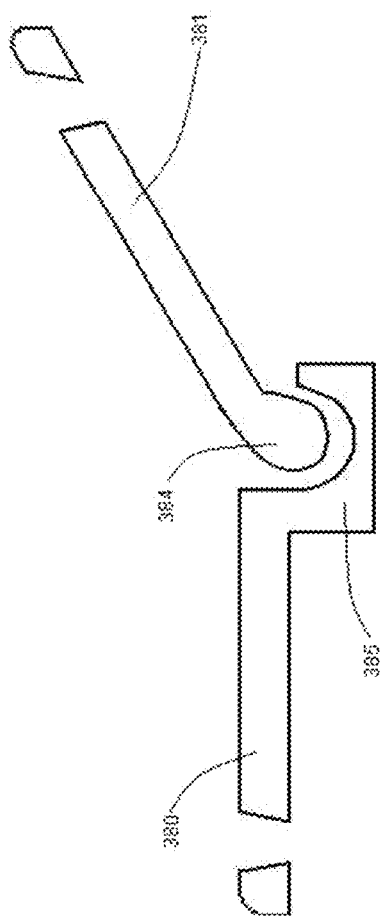

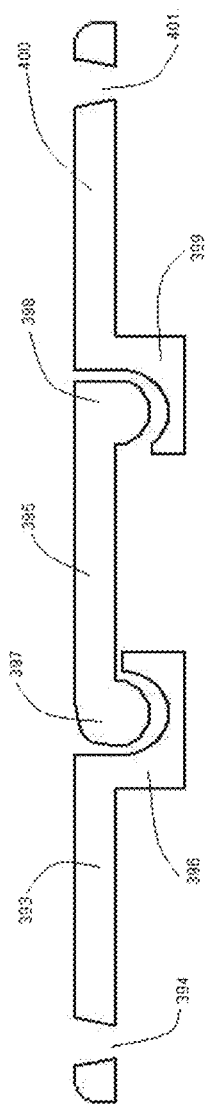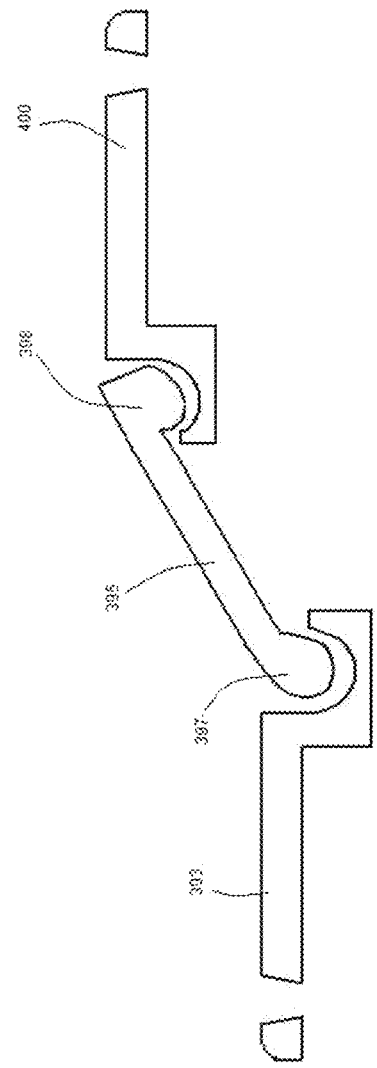
Fig. 163
Fig. 164

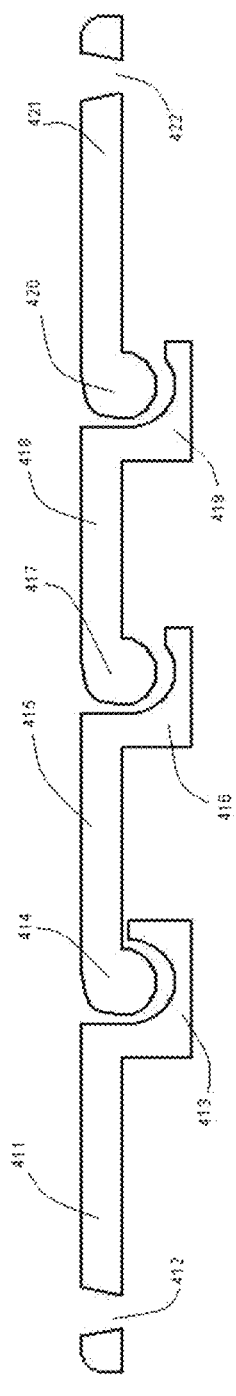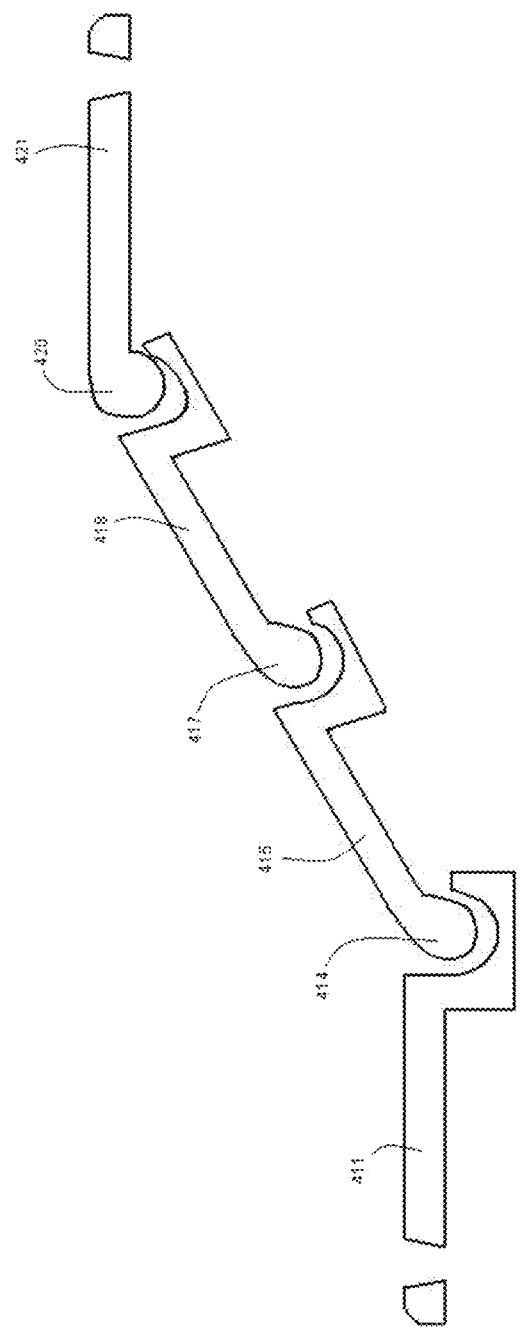

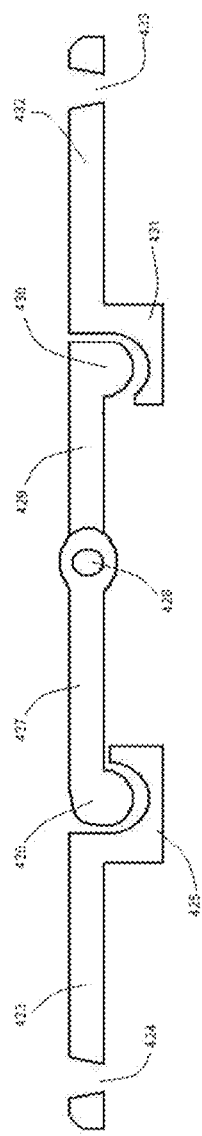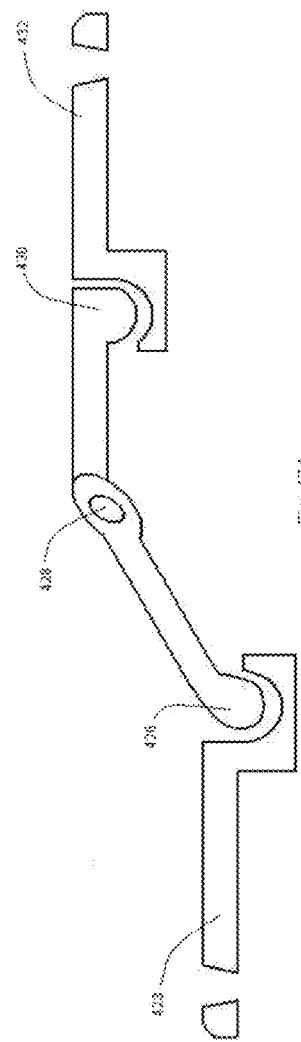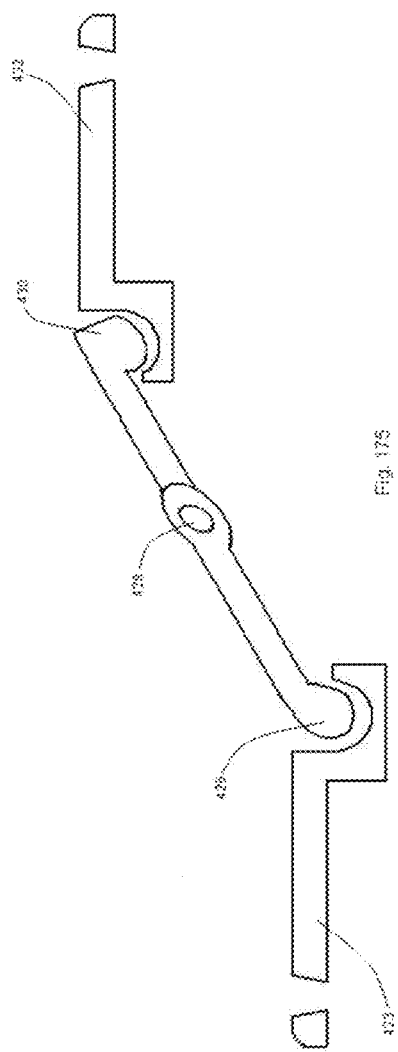

DECOMPRESSIVE CRANIOTOMY DEVICE AND METHODOLOGY

CROSS-REFERENCE TO RELATED APPLICATIONS

The present Utility patent application claims priority benefit of the U.S. provisional application for patent Ser. No. 61/422,640 entitled "Decompressive Craniotomy Device", filed on Dec. 13, 2010, under 35 U.S.C. 119(e). The contents of this related provisional application are incorporated herein by reference for all purposes to the extent that such subject matter is not inconsistent herewith or limiting hereof.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to medical devices. More particularly, one or more embodiments of the invention relate to a device and method for performing a decompressive craniotomy.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Neurosurgery routinely involves performing craniotomies for exposure of the brain and intracranial contents for various intracranial pathologies including, but not limited to, tumors, head injuries, vascular malformations, aneurysms, infections, hemorrhages, strokes, and brain swelling. A craniotomy typically involves the creation of burr holes and the removal of a portion of the skull (i.e., bone flap) with subsequent healing of the bone flap for closure.

By way of educational background, an aspect of the prior art generally useful to be aware of is that several methods and fixation devices are currently available for re-attaching the bone flap to the skull including small metallic or absorbable plates with screws or wires. Another current method is the use of cranial clamps consisting of two connected circular elements placed on the inside and outside surfaces of the skull. The aforementioned cranial fixation devices generally provide for a rigid fixation of the bone flap to the skull.

In cases of post-operative intracranial hemorrhaging and/or the development of brain swelling, a decompressive craniectomy is typically performed. A decompressive craniectomy is a neurosurgical procedure generally used to treat increased pressure within the skull, herein referred to as intracranial pressure (ICP), from causes such as, but not limited to, head injury, stroke, brain tumor, infection, cerebral hemorrhage, space occupying lesions, hypoxia, hypertension, aneurysm, arteriovenous malformation, venous sinus thrombosis, craniosynostosis, and hydrocephalus. The technique of performing a decompressive craniectomy often involves the removal of a portion of the skull and opening of the dura mater covering the brain, thereby allowing the swollen brain to herniate outwards through the surgical skull defect rather than downwards to compress the brainstem. The procedure generally improves outcomes by lowering ICP. Increased ICP is often debilitating or fatal because this pressure may result in compression of the brain and restriction of cerebral blood flow. A typical aim of a decompressive craniectomy is to reduce this pressure. In general, it is believed that the larger the bone flap, the more ICP is reduced. Following removal of the bone flap, the dural opening is typically closed with a patch graft taken from a cow, pig, cadaver, or a synthetic graft. A synthetic collagen matrix is often used as a graft since the matrix is capable of expanding. In addition to reducing ICP, studies typically have shown that a decompressive craniectomy may improve cerebral perfusion pressure and cerebral blood flow in patients with head injuries. A decompressive craniectomy may also be used in some cases to treat major strokes associated with malignant brain swelling and increased ICP. It is believed that a decompressive craniectomy typically improves survival and functional outcome in patients with severe brain swelling from causes such as, but not limited to, head injury or stroke if performed in a timely manner. There usually is an inherent time delay between diagnosing the cause of the increased ICP and performing a decompressive craniectomy. Typically, once a post-operative increase in ICP is detected, either through a clinical exam or an ICP monitoring device, medical treatment is initiated and CT or MRI imaging is obtained to identify the underlying cause of the increased ICP. If the need for another surgery or a decompressive craniectomy is identified, the anesthesiologist and operating room staff are notified and surgery is generally performed as promptly as possible. Unfortunately, at times the operating room and/or staff are unavailable, which may increase the time before the surgery can be performed. Despite the best of attempts by the surgeon, in some cases of massive brain swelling or a rapidly developing post-operative hemorrhage, this delay may result in irreversible brainstem injury and in some cases a consequent vegetative state or death.

After a craniectomy, it is believed that the risk of brain injury is increased because of the removed bone flap, particularly after the patient heals and becomes mobile again. In addition, there is often an obvious cosmetic skin deformity. Therefore, special measures are generally taken to protect the brain, such as, but not limited to, a helmet or a temporary implant in the skull. Other risks that may arise out of a craniectomy include, without limitation, infection, cerebrospinal fluid leakage, hydrocephalus, encephalomyocele, subdural hygroma and hemorrhage.

Once the patient has healed sufficiently, the craniectomy skull defect is usually closed with a cranioplasty. A cranioplasty typically involves the repair of a defect in the vault of the skull. This repair may be carried out by using bone removed in an earlier surgery that has been preserved or by using bone from elsewhere as a graft. Bone that may be used as a graft may include, without limitation, the iliac bone bounding the pelvis, ribs or a portion of adjacent skull bone. If possible, the original bone flap is generally preserved after the craniectomy in anticipation of the cranioplasty. The bone flap is usually stored sterilely in a freezer until the patient is ready for implantation of the bone flap into the craniectomy skull defect. Typically, this time period can last several months since it may take this long to treat the underlying cause of the increased ICP. This extended time period may result in the increased risk of brain injury and may also cause an increased risk of infection in the stored bone flap. Another technique of storing a removed bone flap typically involves placing the bone flap under the skin in the abdomen of the patient. This technique generally requires a surgical procedure to place the bone flap in the abdomen and another surgical procedure to remove the bone flap, thereby typically increasing consequent risks to the patient. In cases where the bone flap cannot be replaced due to infection or any other reason, the skull defect is generally repaired with a prosthetic plate or titanium mesh and bone cement. A prosthetic plate typically cannot completely replicate the original skull defect, and therefore some cosmetic deformity often persists following a prosthetic cranioplasty. The prosthesis may also increase the risk of infection. The risks associated with cranioplasty typically include, without limitation, infection, hemorrhage, brain injury, seizures, and death along with other risks inherent to any surgery and general anesthesia. It is also usually necessary for the patient to remain in the hospital for a week or so after a cranioplasty.

By way of educational background, another aspect of the prior art generally useful to be aware of is that some cranial fixation devices describe their use for distraction osteogenesis. Distraction osteogenesis is a surgical process used to reconstruct craniofacial deformities. The bone is fractured into two segments, and the two bone ends of the bone are gradually moved apart during the distraction phase, allowing new bone to form in the gap and reshape the length of the bone. When the desired length is reached, a consolidation phase follows in which the bone is allowed to solidify in the gap. For example, without limitation, one such device describes a telescopic bone plate for use in bone lengthening by distraction osteogenesis. The bone plate is attached to osteomically separated mandible or skull sections by a thread screw assembly. The extent of the required distraction can be adjusted by an external screwdriver. Another such device describes a skull fixation device typically used for the treatment of craniofacial deformities that provides for relative movement of the skull segments by a percutaneously placed external wrench. Yet another such device describes a mandible or skull expansion plate. The extent of the expansion is adjusted by an externally placed device. Another currently available skull expansion plate comprises a hinged plate at one end and a bone adjuster at the other end comprising two plates with a shaft. The shaft is operated externally to adjust the distance between the bone flap and the skull.

The aforementioned cranial fixation devices in the prior art provide for treatment of craniofacial defects, in particular craniosynostosis. These devices generally require an external screwdriver or other external adjustment means to control the extent of the skull movement allowed and do not typically describe or provide for outward or inward movement of the bone flap relative to the skull in response to a change in the ICP. These devices are also generally placed on the outer surface of the skull and have substantially high profiles which may result in increasing the risk of scalp irritation and palpable cosmetic deformities. One can expect that chronic scalp irritation may cause erosion and exposure of the device through the skin with consequent life threatening infections.

By way of educational background, another aspect of the prior art generally useful to be aware of is that there are multiple methods for performing a decompressive craniectomy. One method of performing a decompressive craniectomy involves attaching the bone flap to the skull with a hinged plate. This method describes attaching the hinged plate to one end of the bone flap and attaching the other end of the bone flap to a rigid plate or no plate at all. The described method typically involves another surgery to fixate the unconstrained bone flap at the rigid plate or plate free end to the skull once the brain swelling subsides. Another method describes a deformable plate which may be used instead of a hinged plate as the bone flap attachment. This construct also typically involves another surgery to fixate the unconstrained bone flap at the straight plate or plate free end of the bone flap. The end of the bone flap attached to the hinged or deformable plate is generally unable to move outwards, and therefore allows limited bone flap movement. Another method involves the use of a two part, sliding device for cranial fixation. This device protrudes outwards from the skull surface and may result in a cosmetic defect, overlying skin irritation, risk of erosion or infection, and typically requires another operation to remove the device once the bone flap heals to the skull.

In view of the foregoing, it is clear that these traditional techniques are not perfect and leave room for more optimal approaches.

SUMMARY OF THE INVENTION

The present invention relates to a cranial fixation device for fixing a bone flap to the skull following a craniotomy. It also provides for constrained outward movement of the bone flap to immediately accommodate for an increase in intracranial pressure (ICP) and subsequently allowing for the bone flap to move inwards up to the skull once the ICP normalizes. Since the decompressive procedure involves leaving the bone flap in place rather than removing it as is done in a decompressive craniectomy, this procedure is more appropriately coined as a decompressive craniotomy.

In one embodiment, the cranial fixation device comprises of two heads with one head attached to the outer surface of the bone flap and the other head attached to the outer surface of the skull. The heads are attached to the skull and bone flap with screws and also connected with each other with an elastomeric band. With an increase in ICP, the elastomeric band allows the head attached to the bone flap to move outwards to accommodate the rise in ICP. With subsequent normalization of the ICP, the elastomeric band retracts the heads and brings the bone flap back to the skull level.

In another embodiment, the cranial fixation device comprises of two heads connected with an elastomeric cord or a spring. One head is positioned on the outer surface of the skull and bone flap and the other head positioned on the inner surface of the skull and bone flap with the elastomeric component positioned in the skull defect or burr hole. With an increase in ICP, the elastomeric cord or spring allows the head attached to the bone flap to move outwards to accommodate the rise in ICP. With subsequent normalization of the ICP, the elastomeric band retracts the heads and brings the bone flap back to the skull level. The heads can also be attached to the bone flap and/or skull with screws, clamps, or spikes.

In another embodiment, the cranial fixation device comprises of two heads with one head attached to the skull and the other to the bone flap. The heads are attached to the skull and bone flap with screws. The telescopic portion slidably connects the two heads and is positioned in the skull burr hole defect. The heads and telescopic extensions are also connected with an elastomeric cord or a spring which maintains the heads and the telescopic extensions in a retracted position when the ICP is normal. With a rise in ICP, the telescopic portion allows outward movement of the bone flap as well as inward movement of the bone flap up to the skull level and does not allow the bone flap to move inward inside the cranium below the skull level.

In another embodiment, the cranial plate comprises of screw holes for attachment of one end to the bone flap and another end to the skull and an intermediate component that is designed to reversibly expand or contract based on the intracranial pressure. The intermediate component comprises a plurality of bridges extending between the attaching portions with each bridge including an elastic tension spring extendable along the bridge arranged in series.

An increase in ICP can result from several pathologies including traumatic injury, stroke, hypoxia, hypertension, brain tumor, aneurysm, arteriovenous malformation, infection, venous sinus thrombosis, craniosynostosis, and hydrocephalus. Traumatic injury can be either closed head injury from blunt trauma or penetrating head injury from a gunshot wound and usually results in development of brain swelling and hemorrhage comprising of subdural hemorrhage, epidural hemorrhage, subarachnoid hemorrhage, intra-ventricular hemorrhage, brain hemorrhage, and cerebral contusions. Strokes can be ischemic, hemorrhagic or a combination of both and usually result from cerebral vessel occlusion. Vessel occlusion can be from an arterial embolus from carotid or vertebral artery stenosis, atrial fibrillation, heart septal defect, heart valve abnormalities, heart or aortic aneurysm surgery, carotid or vertebral artery dissection/thrombosis, and vasculitis. Larger strokes result in the development of severe cerebral cytotoxic edema and brain swelling. Treatment of the strokes with antiplatelet therapy or anticoagulation can also lead to the development of cerebral hemorrhage in some cases, further worsening the brain swelling. Strokes can also be caused by cerebral vessel occlusion from atherosclerotic disease, vasospasm from aneurysmal or traumatic subarachnoid hemorrhage, vasculitis, and a hypercoagulable state. Cerebral venous sinus occlusion can result in significant diffuse brain swelling as well as hemorrhage. Hypertension is a frequent cause of cerebral hemorrhage particularly deep brain and intraventricular hemorrhage. Severe hypertension can also lead to diffuse brain swelling even without any hemorrhage. Hypoxia from cardiac arrest or apnea can lead to diffuse cerebral cytotoxic injury and consequent brain swelling. Ruptured cerebral aneurysms result in subarachnoid hemorrhage but not infrequently also cerebral and intraventricular hemorrhage with associated hydrocephalus which can result in significant and immediate rise in ICP. Ruptured arteriovenous malformations can also result in cerebral and intraventricular hemorrhage. Some arteriovenous malformations like Vein of Galen aneurysm can enlarge to a significant size leading to a rise in intracranial pressure without even rupturing. Brain tumors either metastatic or primary like gliomas and meningiomas, often cause brain swelling from vasogenic edema. Infections include brain abscess, subdural empyema, epidural abscess, and cerebritis can also lead to significant brain swelling. Seizures can lead to diffuse brain swelling from increased cerebral blood flow and metabolism.

When an increase in ICP exceeds the normal range, the bone flap is pushed outwards and places the telescopic portion in an extended position. Once the ICP normalizes, the telescopic portions fall back into a retracted position facilitated by the flexible components (elastic cord or a spring). The retracted telescopic portion position approximates the two heads and thereby the bone flap and the skull. Typically two more of the cranial fixation devices would be needed to achieve this form of decompressive craniectomy. Alternatively, a cranial fixation device can be placed on one side of the bone flap and a hinge device can be placed on the other side to provide a similar but limited decompressive craniotomy. In another embodiment of the cranial fixation device, the heads are attached to the skull and bone flap with spikes or a combination of screws on one head and spikes on the other. In another embodiment of the cranial fixation device, one or both head comprise of clamps which are attached to the skull and/or bone flap.

In another embodiment, the cranial fixation device telescopic portion comprises a locking mechanism that engages when the telescopic bone fastener is in a retracted position. The retracted telescopic portion position approximates the bone flap to the skull when the intracranial pressure is in the normal range. With an increase in ICP, the pressure placed on the bone flap disengages the telescopic bone fastener locking mechanism and allows outward movement of the bone flap to accommodate the increase in ICP. Subsequently, once the ICP normalizes, the bone flap retracts back to the skull level facilitated by the spring or elastomeric band/cord. The locking mechanism comprises of one or more collapsible balls mounted on one telescopic extension with corresponding sockets on the said second telescopic component. Other locking mechanisms include ratchet teeth, ratchet teeth and pawl mechanism, collapsible ratchet teeth, threads, hook mechanism, and ridges with notches.

Several locking mechanisms are described here forth. In one embodiment of the cranial fixation device, the locking mechanism comprises a ridge in one telescopic extension with a corresponding socket or defect in the other telescopic extension. In another embodiment of the cranial fixation device, the locking mechanism comprises of ridges in the telescopic extension with notches in the other telescopic extension. In another embodiment of the cranial fixation device, the locking mechanism comprises of ratchet teeth in the telescopic extensions. In another embodiment of the cranial fixation device, the locking mechanism comprises of ratchet teeth in one telescopic extension with a pawl in the other telescopic extension. The ratchet teeth can be unidirectional or bidirectional. In another embodiment of the cranial fixation device, the locking mechanism comprises of collapsible ratchet teeth in the telescopic extension with an engaging defect or ratchet teeth in the other telescopic extension. In another embodiment of the cranial fixation device, the locking mechanism comprises a hook in one telescopic extension with a corresponding engaging hole in the other telescopic extension.

Rather than providing a fixed locked position once implanted as described in all the cranial fixation devices in the prior art, the current invention allows for constrained outward movement of the bone flap relative to the skull in cases of cerebral swelling and subsequently retracts the bone flap against the skull once the swelling subsides.

In the various embodiments described herein the preferred head configuration is circular or semi-circular so as to cover the burr hole or skull opening. Other plate configurations could be rectangular, square, straight, X-shaped, Y-shaped, fan shaped, or any other configuration able to connect the skull to the bone flap. Similarly, the telescopic configurations described are either cylindrical or rectangular and designed to fit into the skull defect or burr hole. Other telescopic configurations could be partially solid, tapered, V-shaped or any other configuration that fits the skull opening. The positioning of the telescopic portion in the burr hole skull defect provides for a very low profile cranial fixation with no scalp irritation or risk of skin erosion. The cranial fixation device can be made of titanium or titanium alloy for MRI imaging compatibility. They could also be made of a bio-absorbable material (polyesters, poly amino acids, polyanhydrides, polyorthoesters, polyurethanes, polycarbonates, homopolymers, copolymers of poly lactic acid and poly glycolic acid, copolyesters of e-caprolactone, trimethylene carbonate, and para-dioxanone), or allograft or xenograft bone that is absorbed by the body over time once the bone flap has fused with the skull. Alternatively, it could made of a radiolucent material (polyetheretherketone), plastic, or a combination of plastic and metal to reduce CT and MRI imaging artifact.

Although the application for the cranial fixation device described in the various embodiments is for fixation of the bone flap to the skull following a craniotomy and provide for a method of decompressive craniectomy for treatment of increased intracranial pressure, it can also be used to cover a burr hole or skull fracture and treat congenital cranial skull defects like craniosynostosis Various embodiments and advantages of the current invention are set forth in the following detailed description and claims which will be readily apparent to one skilled in the art.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 1 through 4 illustrate an exemplary cranial fixation device in accordance with an embodiment of the present invention. FIG. 1 is a diagrammatic side view of the device in a contracted position. FIG. 2 is a diagrammatic side view of the device in an expanded position view, FIG. 3 is a diagrammatic side view with screws in place, and FIG. 4 is a diagrammatic side view with screws in place.

FIG. 5 is a cross-sectional side view of the device in a contracted position. FIG. 6 is a cross-sectional side view of the device in an expanded position view. FIG. 7 is a top view of the device in a contracted position. FIG. 8 is a top view of the device in an expanded position view. FIG. 9 is a cross-sectional top view of the device in a contracted position. FIG. 10 is a cross-sectional top view of the device in an expanded position view.

FIG. 11 is a perspective side view of the device in a contracted position and FIG. 12 is a perspective side view of the device in an extended position.

FIG. 13 is a perspective side view of the device in a contracted position and FIG. 14 is a perspective side view of the device in an extended position.

FIG. 16 is a diagrammatic side view of the device in a contracted position. FIG. 15 is a diagrammatic side view of the device in an expanded position view.

FIG. 18 is a diagrammatic side view of the device in a contracted position. FIG. 17 is a diagrammatic side view of the device in an expanded position view.

FIG. 19 is a perspective side view of the device in a contracted position, FIG. 20 is a perspective side view of the device in a partially extended position, and FIG. 21 is a perspective side view of the device in an extended position.

FIG. 22 is a cross-sectional side view of the device in a contracted position. FIG. 23 is a cross-sectional side view of the device in an expanded position view.

FIG. 24 is a cross-sectional side view of the device in a contracted position. FIG. 25 is a cross-sectional side view of the device in an expanded position view.

FIG. 20 shows a brain in a non-swollen state, and FIG. 21 shows the brain in a swollen state.

FIG. 28 is a perspective side view of the device in a contracted position and FIG. 29 is a perspective side view of the device in an extended position.

FIG. 30 is a cross-sectional side view of the device in a contracted position. FIG. 31 is a cross-sectional side view of the device in an expanded position view.

FIG. 32 is a cross-sectional side view of the device in a contracted position. FIG. 33 is a cross-sectional side view of the device in an expanded position view.

FIG. 35 is a cross-sectional side view of the device in a contracted position. FIG. 34 is a cross-sectional side view of the device in an expanded position view.

FIG. 36 is a perspective side view of the device in a contracted position and FIG. 37 is a perspective side view of the device in an extended position. FIG. 38 is a cross-sectional side view of the device in a contracted position. FIG. 39 is a cross-sectional side view of the device in an expanded position view.

FIG. 40 is a cross-sectional side view of the device in a contracted position. FIG. 41 is a cross-sectional side view of the device in an expanded position view.

FIG. 42 is a cross-sectional side view of the device in a contracted position. FIG. 43 is a cross-sectional side view of the device in an expanded position view.

FIG. 44 is a cross-sectional side view of the device in a contracted position. FIG. 45 is a cross-sectional side view of the device in an expanded position view.

FIG. 46 is a cross-sectional side view of the device in a contracted position. FIG. 47 is a cross-sectional side view of the device in an expanded position view.

FIG. 48 is a cross-sectional side view of the device in a contracted position. FIG. 49 is a cross-sectional side view of the device in an expanded position view.

FIG. 50 is a cross-sectional side view of the device in a contracted position. FIG. 51 is a cross-sectional side view of the device in an expanded position view.

FIG. 52 is a cross-sectional side view of the device in a contracted position: FIG. 53 is a cross-sectional side view of the device in an expanded position view.

FIG. 54 is a cross-sectional side view of the device in a contracted position. FIG. 55 is a cross-sectional side view of the device in an expanded position view.

FIG. 56 is a cross-sectional side view of the device in a contracted position. FIG. 57 is a cross-sectional side view of the device in an expanded position view.

FIG. 58 is a cross-sectional side view of the device in a contracted position. FIG. 59 is a cross-sectional side view of the device in an expanded position view.

FIG. 60 is a cross-sectional side view of the device in a contracted position. FIG. 61 is a cross-sectional side view of the device in an expanded position view.

FIG. 62 is a perspective side view of the device in a contracted position, FIG. 63 is a perspective side view of the device in a partially extended position, and FIG. 64 is a perspective side view of the device in an extended position.

FIG. 65 is a perspective side view of the device in a contracted position and FIG. 66 is a perspective side view of the device in an extended position.

FIG. 67 is a perspective side view of the device in a contracted position and FIG. 68 is a perspective side view of the device in an extended position.

FIG. 69 is a perspective side view of the device in a contracted position and FIG. 70 is a perspective side view of the device in an extended position.

FIG. 71 shows a brain in a non-swollen state, and FIG. 72 shows the brain in a swollen state.

FIG. 73 is a perspective side view of the device in a contracted position and FIG. 74 is a perspective side view of the device in an extended position.

FIG. 75 shows a brain in a non-swollen state, and FIG. 76 shows the brain in a swollen state.

FIG. 77 is a perspective side view of the device in a contracted position and FIG. 78 is a perspective side view of the device in an extended position.

FIG. 79 is a perspective side view of the device in a contracted position and FIG. 80 is a perspective side view of the device in an extended position.

FIG. 81 shows a brain in a non-swollen state, and FIG. 82 shows the brain in a swollen state.

FIG. 83 is a perspective side view of the device in a contracted position and FIG. 84 is a cross-sectional side view of the device in an extended position.

FIG. 85 is a perspective side view of the device in a contracted position and FIG. 86 is a perspective side view of the device in an extended position.

FIG. 87 is a perspective side view of the device in a contracted position and FIG. 88 is a perspective side view of the device in an extended position.

FIG. 89 is a perspective side view of the device in a contracted position and FIG. 90 is a perspective side view of the device in an extended position.

FIG. 91 is a perspective side view of the device in a contracted position and FIG. 92 is a perspective side view of the device in an extended position.

FIG. 93 is a perspective side view of the device in a contracted position and FIG. 94 is a perspective side view of the device in an extended position.

FIG. 95 shows a brain in a non-swollen state, and FIG. 96 shows the brain in a swollen state.

FIGS. 97 through 100 illustrate an exemplary cranial fixation device in accordance with an embodiment of the present invention. FIG. 98 is a perspective side view of the device in a contracted position and FIG. 97 is a perspective side view of the device in an extended position. FIG. 100 is a cross-sectional side view of the device in a contracted position. FIG. 99 is a cross-sectional side view of the device in an expanded position view.

FIG. 101 is a perspective side view of the device in a contracted position, FIG. 102 is a perspective side view of the device in a partially extended position, and FIG. 103 is a perspective side view of the device in an extended position. FIG. 104 is a perspective side view of the device implanted in the contracted position.

FIGS. 105 and 106 illustrate an exemplary cranial fixation device in accordance with an embodiment of the present invention. FIG. 106 is a cross-sectional side view of the device in a contracted position. FIG. 105 is a cross-sectional side view of the device in an expanded position view.

FIG. 108 is a cross-sectional side view of the device in a contracted position. FIG. 107 is a cross-sectional side view of the device in an expanded position view.

FIG. 110 is a cross-sectional side view of the device in a contracted position. FIG. 109 is a cross-sectional side view of the device in an expanded position view.

FIGS. 111 and 112 illustrate an exemplary cranial fixation device in accordance with an embodiment of the present invention. FIG. 112 is a cross-sectional side view of the device in a contracted position. FIG. 111 is a cross-sectional side view of the device in an expanded position view.

FIG. 113 is a cross-sectional side view of the device in a contracted position. FIG. 114 is a cross-sectional side view of the device in an expanded position view.

FIG. 115 is a cross-sectional side view of the device in a contracted position. FIG. 116 is a cross-sectional side view of the device in an expanded position view.

FIG. 120 is a schematic view of the cranial fixation device in FIG. 117 in an extended state with the removable distracter in FIG. 118 in place.

FIG. 121 is a schematic view of the cranial fixation device in FIG. 117 in a retracted state with the distracter in FIG. 118 in place.

FIG. 134 is a schematic view of another embodiment of the cranial fixation device.

FIG. 135 is schematic view of the distracter for the cranial fixation device in FIG. 134.

FIG. 136 is another schematic side view of the distracter in FIG. 135.

FIGS. 137 and 138 are perspective side views of the fixation device implanted in the skull following a craniotomy. FIG. 137 illustrates the retracted position of the bone flap and FIG. 138 illustrates the outward position of the bone flap.

FIGS. 141 and 142 illustrate an exemplary cranial fixation device in accordance with an embodiment of the present invention. FIG. 141 is a cross-sectional side view of the device in a contracted position. FIG. 142 is a cross-sectional side view of the device in an expanded position view.

FIGS. 143 through 145 illustrate an exemplary cranial fixation device in accordance with an embodiment of the present invention. FIG. 114 is side view of the device in a contracted position. FIG. 143 is a cross-sectional side view of the device in an expanded position view. FIG. 145 is a cross-sectional view taken along the line A in FIG. 143.

FIG. 146A is a perspective side view of the device in a partially extended position. FIG. 16B is another perspective side view of the device in a partially extended position. FIG. 147 is a perspective side view of the device in a completely extended position view. FIG. 148 is a perspective side view of the device in a retracted position.

FIG. 150 is a perspective side view of the device in a contracted position and FIG. 149 is a perspective side view of the device in an extended position.

FIG. 151 is a cross-sectional side view of the device in a contracted position. FIG. 152 is a cross-sectional side view of the device in an expanded position view.

FIG. 153 is a cross-sectional side view of the device in a contracted position. FIG. 154 is a cross-sectional side view of the device in an expanded position view.

FIG. 155 is a cross-sectional side view of the device in a contracted position. FIG. 156 is a cross-sectional side view of the device in a partially extended position view. FIG. 157 is a cross-sectional side view of the device in a fully extended position view.

FIGS. 158 and 159 illustrate an exemplary cranial fixation device in accordance with an embodiment of the present invention. FIG. 158 is a cross-sectional side view of the single hinge device in a straight position. FIG. 159 is a cross-sectional side view of the device in an upward position view.

FIG. 162 is a perspective side view of the double hinged device in a straight position and FIG. 161 is a cross-sectional side view of the device in a straight position. FIG. 162 is a cross-sectional side view of the device in an upward position view.

FIGS. 163 and 164 illustrate an exemplary cranial fixation device in accordance with an embodiment of the present invention. FIG. 163 is a cross-sectional side view of the double hinge device in a straight position. FIG. 164 is a cross-sectional side view of the device in an upward position view.

FIG. 165 is a perspective side view of the triple hinged device in a straight position and FIGS. 161 through 170 are cross-sectional side views of the device in different positions.

FIGS. 171 and 172 illustrate an exemplary cranial fixation device in accordance with an embodiment of the present invention. FIG. 171 is a cross-sectional side view of the triple hinge device in a straight position. FIG. 172 is a cross-sectional side view of the device in an upward position view.

FIGS. 173 through 175 illustrate an exemplary cranial fixation device in accordance with an embodiment of the present invention. FIG. 163 is a cross-sectional side view of the triple hinge device in a straight position. FIGS. 174 and 175 are cross-sectional side views of the device in an upward position view.

FIG. 176 is a top view of the device in a straight position. FIG. 177 is a bottom view of the device in a straight position. FIG. 178 is a cross-sectional top view of the device. FIG. 179 is a cross-sectional side view of the device in a straight position. FIG. 180 is a cross-sectional side view of the device in a straight position. FIG. 181 is a cross-sectional side view of the device in a partial upward position. FIG. 182 is a cross-sectional side view of the device in a complete upward position.

FIG. 183 is a side view of the device in a straight position. FIG. 184 is a cross-sectional side view of the device in a straight position. FIG. 185 is a cross-sectional side view of the device in an upward position. FIG. 186 is a top view of the device and FIG. 187 is a cross-sectional top view of the device.

FIG. 188 is a perspective side view of the device in a contracted position and FIG. 189 is a perspective side view of the device in an extended position.

FIG. 190 is a perspective side view of the device in a contracted position and FIG. 191 is a perspective side view of the device in an extended position. FIG. 191*a* is a cross-sectional view of the device taken along line A in FIG. 191.

FIG. 192 is a perspective side view of the device in a contracted position and FIG. 192 is a perspective side view of the device in an extended position.

FIG. 194 is a perspective side view of the device in a contracted position, FIG. 195 is a perspective side view of the device in an extended position, and FIG. 196 is a perspective side view of the device in an extended and upward position.

FIG. 197 is a perspective side view of the device in a contracted position and FIG. 198 is a perspective side view of the device in an extended position.

FIG. 199 shows a brain in a non-swollen state, and FIG. 200 shows the brain in a swollen state.

FIG. 201 is a top view of the device in a contracted position and FIG. 202 is a top view of the device in an extended position.

FIG. 203 is a top view of the device in a contracted position and FIG. 204 is a top view of the device in an extended position.

FIG. 206 is a top view of the device in a contracted position and FIG. 206 is a perspective side view of the device in a contracted position.

FIG. 207 is a side view of the device in a contracted position and FIG. 208 is a side view of the device in an extended position.

FIG. 209 is a side view of the device in a contracted position and FIG. 210 is a side view of the device in an extended position.

DETAILED DESCRIPTION OF SOME EMBODIMENTS

Figure 1:
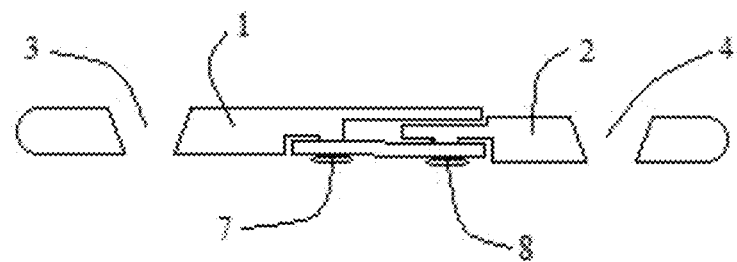

Embodiments of the present invention are best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Considering the complexities and risks typically involved in the post-operative management of critically ill patients undergoing a craniotomy, a practical embodiment of the present invention provides a method and a cranial fixation device for fixing a bone flap to the skull following a craniotomy with immediate treatment of increased ICP that generally avoids the need for performing a subsequent cranioplasty. Many practical embodiments provide cranial fixation following a craniotomy with a fixation device that allows for constrained movement of the bone flap to immediately accommodate an increase in ICP and subsequently enables the bone flap to move inward toward the skull once the ICP normalizes. In many practical embodiments this fixation device is a flexible and expandable cranial fixation plate. In some practical embodiments, the cranial fixation device comprises spaced anchor portions and an expandable intermediate component extending between the anchor portions allowing for expansion and contraction. Since the decompressive procedure provided in many practical embodiments involves leaving the bone flap in place rather than removing the bone flap as is typically done in a decompressive craniectomy, this procedure is herein referred to as a decompressive craniotomy.

Figure 2:
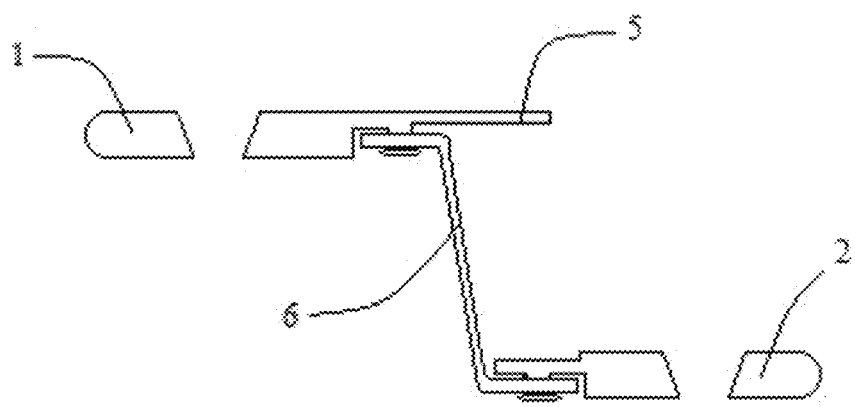

The decompressive craniotomy device as shown in FIGS. 1-4 comprises of a head 1 and a head 2 with an elastomeric band 6 connecting the two heads. The head 1 also contains an extension 7 to secure the band 6 and the head 2 contains an extension 8 to secure the band 6. The elastomeric band is stretchable and allows for inward or outward movement of the heads relative to each other. The medial edge of the head has an extension 5 that overlaps with the head 2 when they are approximated, thereby not allowing the head 1 to move inward beyond the head 2. The head 1 has holes 3 which allows placement of screws 9 attaching the head to the outer surface of the bone flap. Head 2 has holes 4 through which screws 10 can be placed for attachment of the head to the outer surface of the skull. FIG. 1 shows the heads approximated by the elastomeric band and FIG. 2 shows the head 1 moved outwards relative to head 2 in response to an increased ICP.

Figure 5:
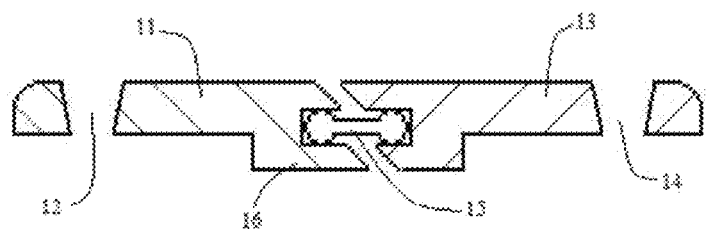
FIGS. 5 through 10 illustrate an exemplary cranial fixation device, in accordance with an embodiment of the present invention.
Figure 6:
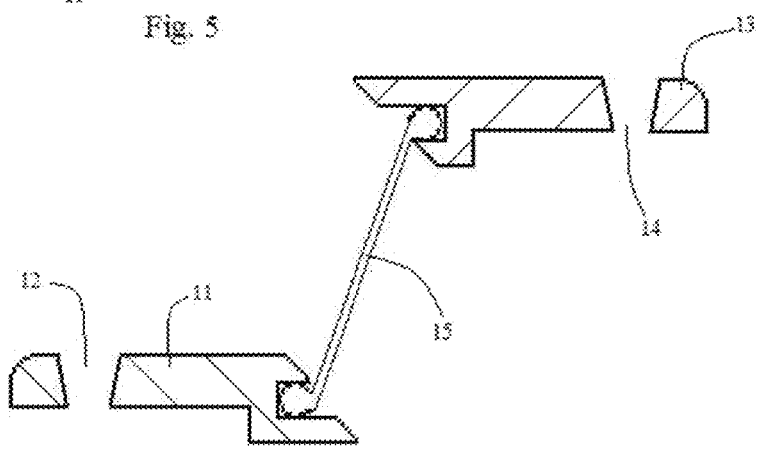
Figure 7:
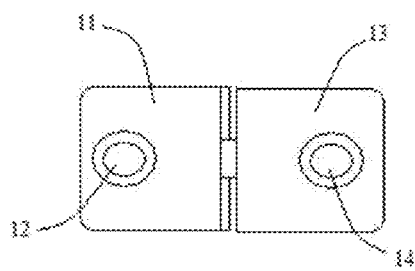
Figure 8:
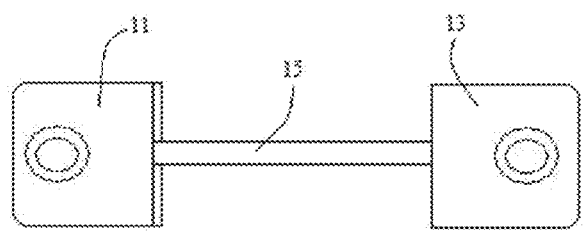
Figure 9:
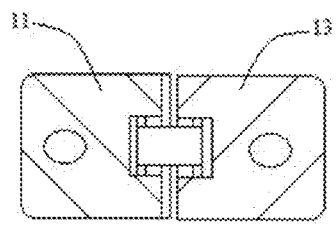
Figure 10:
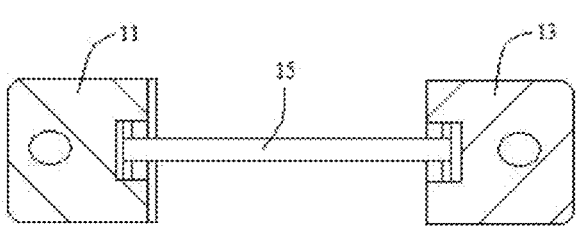

In another embodiment of the decompressive craniotomy device as shown in FIGS. 5-10, the heads 11 and a head 13 are connected with an elastomeric band 15 residing in a housing portion 16 positioned in the skull burr hole defect. The elastomeric band 15 is stretchable and allows for inward or outward movement of the heads relative to each other. The medial edges of the heads 11 and 13 are sloped and overlap each other thereby not allowing the head 11 to move inward beyond the head 13. The head 13 has holes 14 which allows placement of screws attaching the head to the outer surface of the bone flap. Head 11 has holes 12 through which screws can be placed for attachment of the head to the outer surface of the skull. FIGS. 5, 7, and 9 show the heads approximated by the elastomeric band and FIGS. 6, 8, and 10 show the head 11 moved outwards relative to head 13 in response to an increased ICP.

Figure 11:
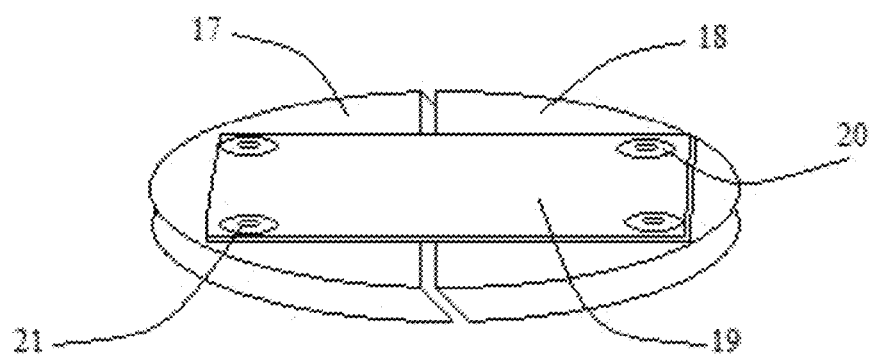
FIGS. 11 and 12 illustrate an exemplary cranial fixation device in accordance with an embodiment of the present invention.
Figure 12:
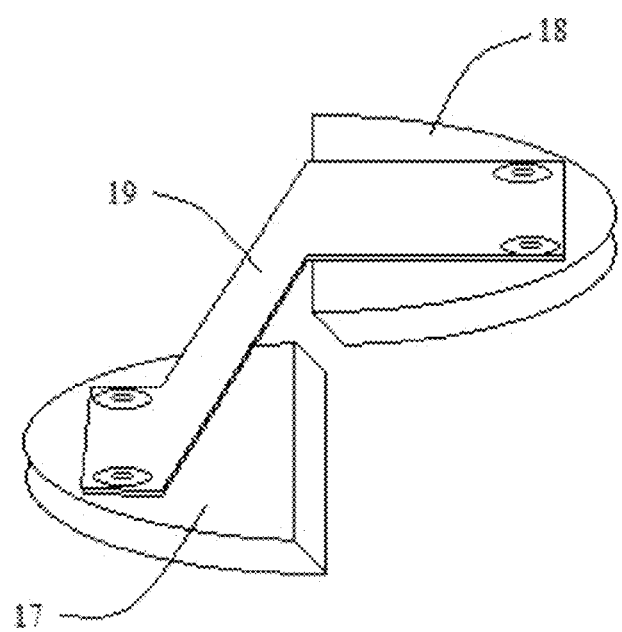

In another embodiment of the decompressive craniotomy device as shown in FIGS. 11 and 12, the heads 17 and 18 are connected with an elastomeric band 19. The elastomeric band 19 is stretchable and allows for inward or outward movement of the heads relative to each other. The medial edges of the heads 17 and 18 are sloped and overlap each other thereby not allowing the head 17 to move inward beyond the head 18. The head 18 has holes 20 which allows placement of screws attaching the head to the outer surface of the bone flap. Head 17 has holes 22 through which screws can be placed for attachment of the head to the outer surface of the skull. FIG. 11 shows the heads approximated by the elastomeric band and FIG. 12 shows the head 18 moved outwards relative to head 17 in response to an increased ICP.

Figure 13:
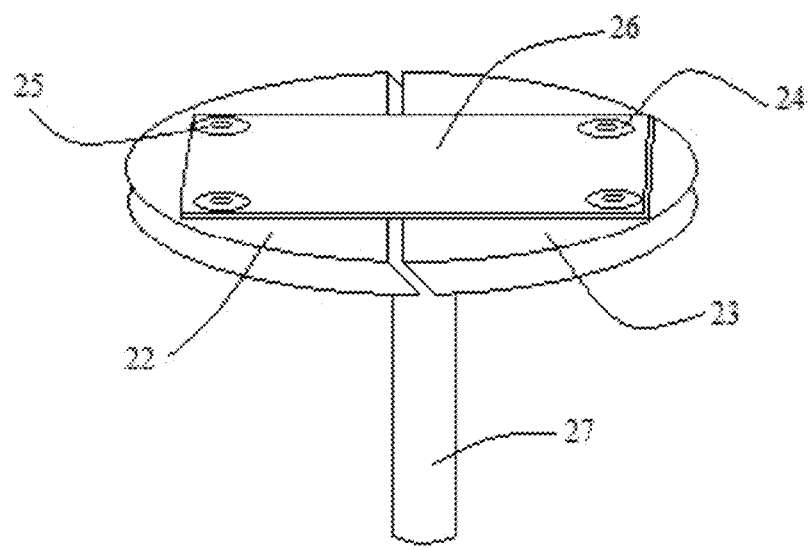
FIGS. 13 and 14 illustrate an exemplary cranial fixation device in accordance with an embodiment of the present invention.
Figure 14:
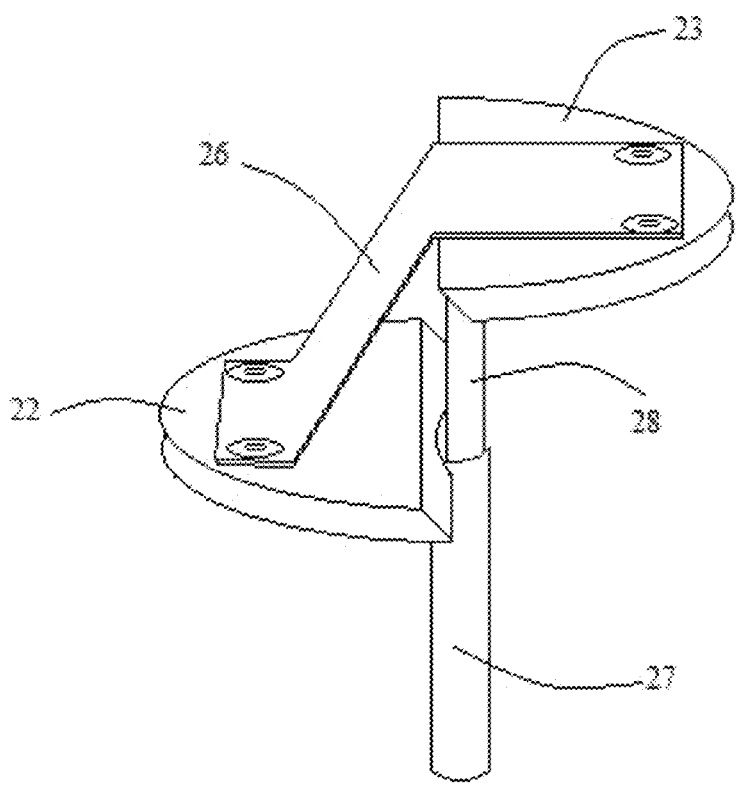

In another embodiment of the decompressive craniotomy device as shown in FIGS. 13 and 14, the heads 22 and 22 are connected with an elastomeric band 26. The heads also comprise a telescopic extension 28 and 27. The elastomeric band 19 is stretchable and allows for inward or outward movement of the heads controlled by the telescopic extensions relative to each other. The medial edges of the heads 22 and 23 are sloped and overlap each other thereby not allowing the head 23 to move inward beyond the head 22. The head 23 has holes 24 which allows placement of screws attaching the head to the outer surface of the bone flap. Head 22 has holes 25 through which screws can be placed for attachment of the head to the outer surface of the skull. FIG. 13 shows the heads approximated by the elastomeric band with the telescopic extensions in a retracted position and FIG. 14 shows the head 23 moved outwards relative to head 22 in response to an increased ICP with the telescopic extensions 27 and 28 placed in an extended position.

Figure 15:
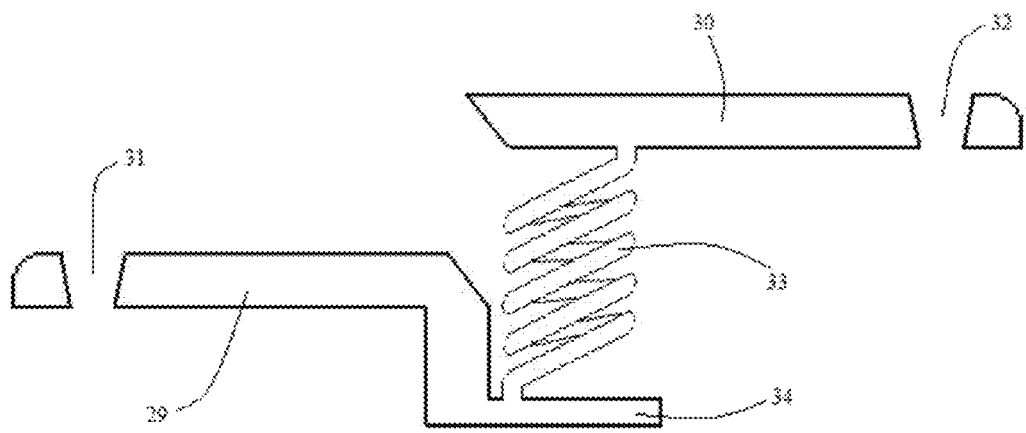
FIGS. 15 and 16 illustrate an exemplary cranial fixation device in accordance with an embodiment of the present invention.
Figure 16:
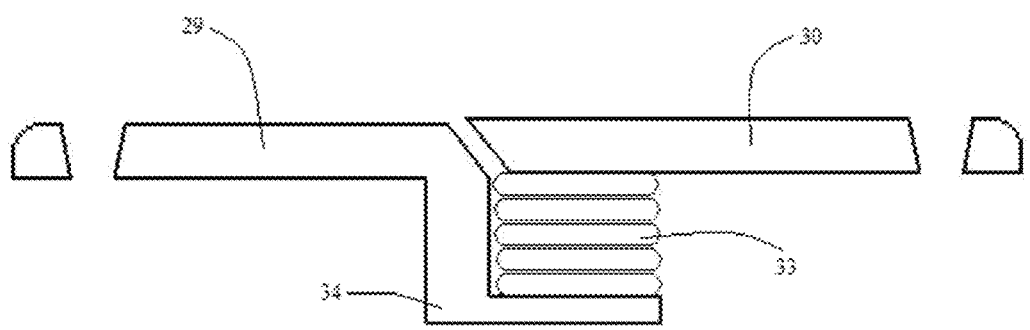

In another embodiment, the decompressive craniotomy device as shown in FIGS. 15 and 16 comprises of a head 29 and a head 30. The head 29 also contains an extension 34 attached to a spring 33. The spring 33 is also attached to the head 30 at the other end. The spring stretches to allow for inward or outward movement of the heads relative to each other. The medial edges of the heads are sloped and overlap when they are approximated, thereby not allowing the head 30 to move inward beyond the head 29. The head 30 has holes 32 which allows placement of screws attaching the head to the outer surface of the bone flap. Head 29 has holes 31 through which screws can be placed for attachment of the head to the outer surface of the skull. The extension 34 with the spring 33 are designed to be positioned in the skull burr hole defect to provide a very low profile and avoid any skin irritation. FIG. 16 shows the heads approximated by the spring 33 and FIG. 15 shows the head 30 moved outwards relative to head 29 in response to an increased ICP.

Figure 17:
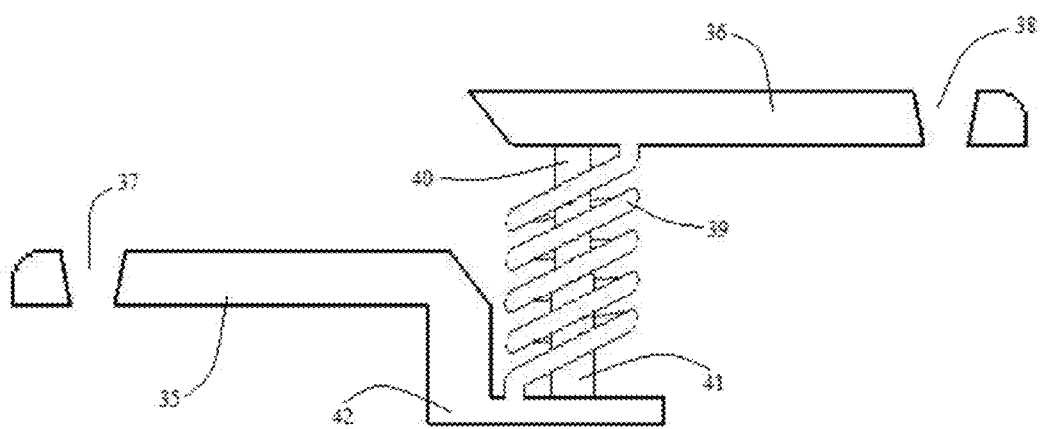
FIGS. 17 and 18 illustrate an exemplary cranial fixation device in accordance with an embodiment of the present invention.
Figure 18:
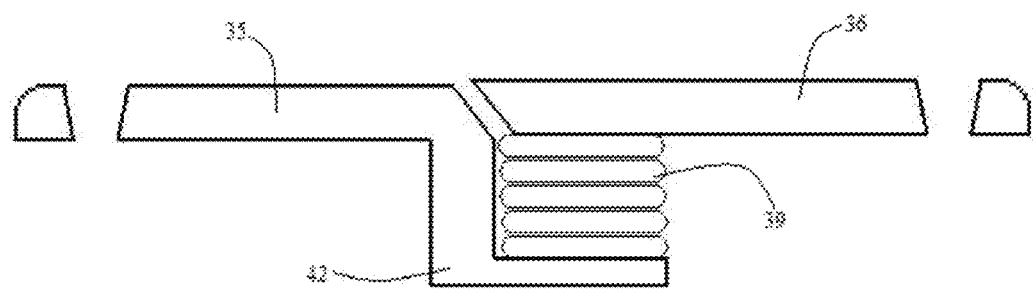

In another embodiment, the decompressive craniotomy device as shown in FIGS. 17 and 18 comprises of a head 35 and a head 36. The head 35 also contains an extension 42 attached to a spring 39. The spring 39 is also attached to the head 36 at the other end. The heads 35 and 36 are also connected by telescopic extensions 40 and 41 The spring along with the telescopic extensions expand and retract to allow for inward or outward movement of the heads relative to each other. The medial edges of the heads are sloped and overlap when they are approximated, thereby not allowing the head 36 to move inward beyond the head 35. The head 36 has holes 38 which allows placement of screws attaching the head to the outer surface of the bone flap. Head 35 has holes 37 through which screws can be placed for attachment of the head to the outer surface of the skull. FIG. 18 shows the heads approximated by the spring 39 and FIG. 14 shows the head 36 moved outwards relative to head 35 in response to an increased ICP with the spring 39 and telescopic extensions 40 and 41 in an extended position.

Figure 19:
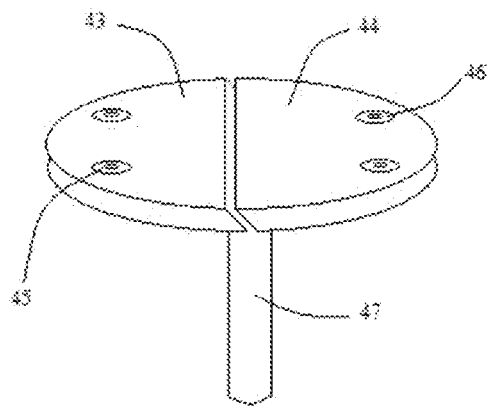
FIGS. 19 through 21 illustrate an exemplary cranial fixation device in accordance with an embodiment of the present invention.
Figure 20:
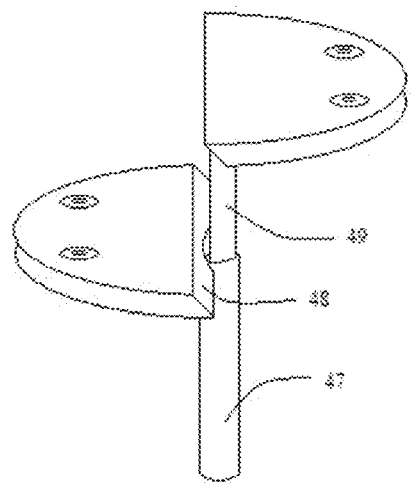
Figure 21:
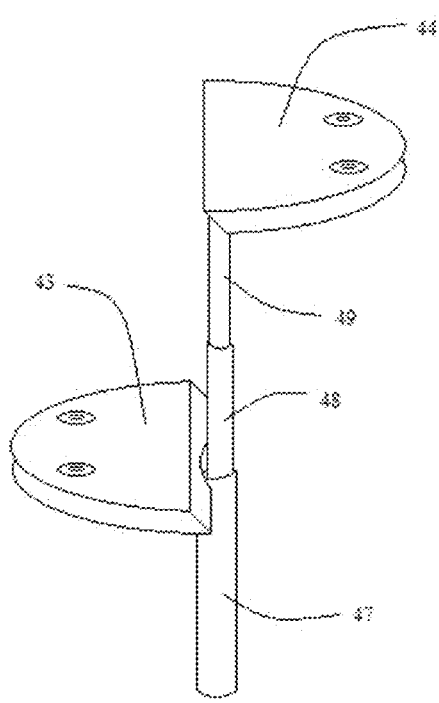
Figure 22:
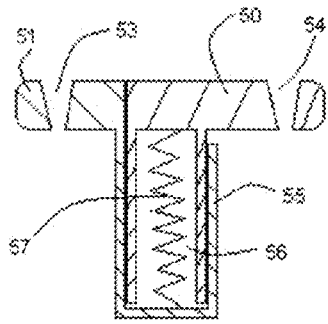
FIGS. 22 and 23 illustrate an exemplary cranial fixation device in accordance with an embodiment of the present invention.
Figure 23:
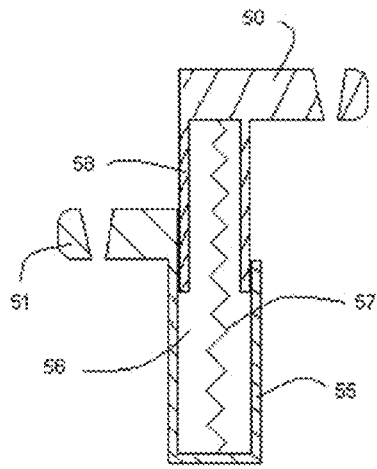
Figure 24:
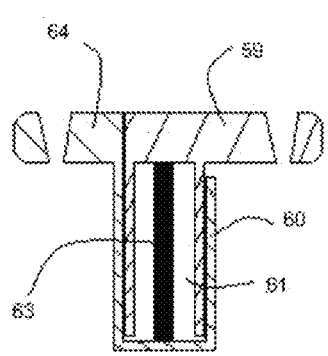
FIGS. 24 and 25 illustrate an exemplary cranial fixation device in accordance with an embodiment of the present invention.
Figure 25:
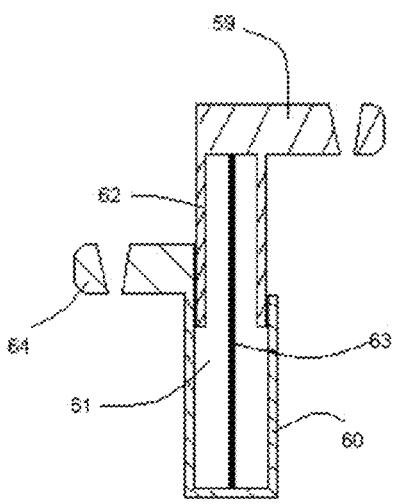

The decompressive craniotomy device as shown in FIGS. 19 and 20 comprises of a head 43 with an extension 47 and a head 44 with an extension 49. The extensions 47 and 49 are telescopic and allow for inward or outward movement of the heads relative to each other. The medial edges of the heads 19 and 20 are sloped 48 and overlap each other when the heads are approximated, thereby not allowing the head 44 to move inward beyond the head 43. The head 43 has holes 45 which allows placement of screws attaching the head to the outer surface of the skull. Head 44 has holes 46 through which screws can be plated for attachment of the head to the outer surface of the bone flap. FIG. 19 shows the telescopic extensions in a compressed position whereby extension 49 is contained in the extension 47 and FIG. 20 shows the extensions 47 and 49 in a distracted position. FIG. 21 illustrates another embodiment of the cranial fixation device with an intermediate telescopic component 48 which allows the two heads 43 and 44 attached to their respective bone flap and skull to move outwards further if needed to accommodate an increase in intracranial pressure. The heads or telescopic components are connected with a flexible material like a spring or an elastomeric band which retracts the telescopic extensions thereby positioning the bone flap down towards the skull once the ICP has reduced to a normal level. The flexible material provides constrained inward and outward movement of the heads depending upon the ICP. As shown in FIGS. 22 and 23, the two heads 50 and 51 contain telescopic extensions 55 and 58 with bone screw holes 53 and 54. The head 50 is attached to a spring 57 that is housed in the hollow component 56 of the telescopic extension and is also attached to the telescopic extension 55. In the current embodiment the spring is shown residing inside the telescopic extensions but in other embodiments it can be placed outside the telescopic extensions. With normalization of the intracranial pressure the spring 57 retracts the heads and telescopic extensions to approximate the two heads 50 and 51 together as shown in FIG. 22. With an increase in intracranial pressure the head 50 connected to the bone flap is pushed outwards and places the telescopic extensions 55 and 58 in an extended position as shown in FIG. 23. FIGS. 24 and 25 illustrate another embodiment of the fixation device with heads 59 and 64 and telescopic extensions 60 and 62 with an elastomeric band 63 that is housed in the hollow portion 61 of the telescopic extensions. FIG. 24 shows the retracted position of the telescopes with heads approximated and FIG. 25 shows the extended position of the telescopic extensions.

Figure 26:
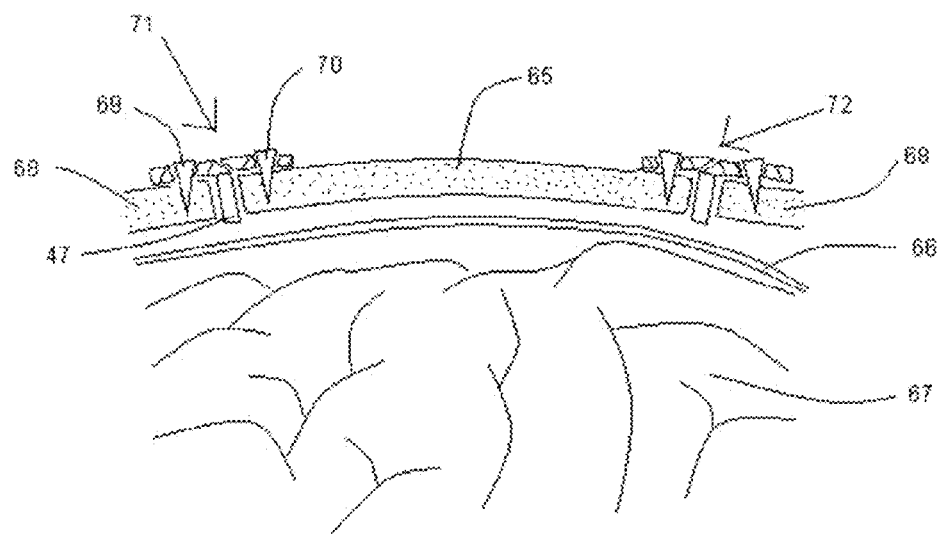
FIGS. 26 and 27 are cross sectional side views of exemplary cranial fixation devices attached to a skull and a bone flap for a decompressive craniotomy, in accordance with an embodiment of the present invention.
Figure 27:
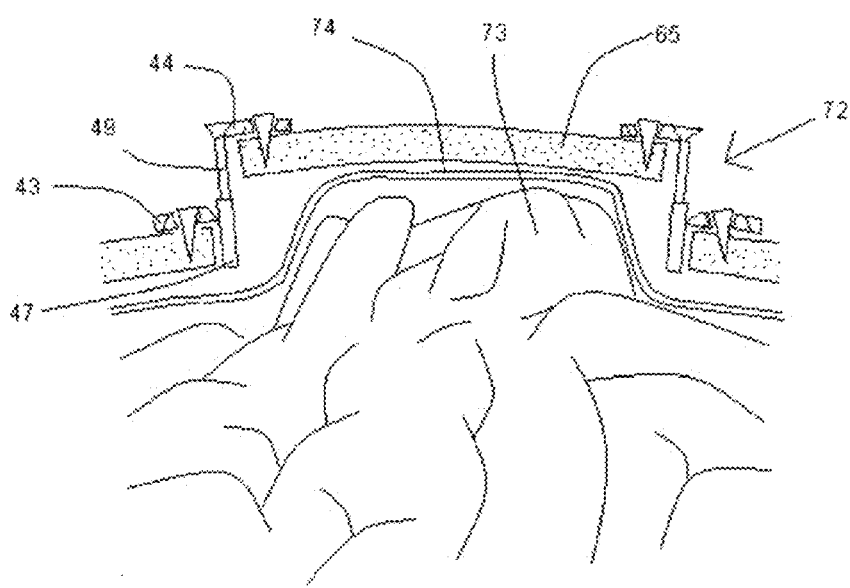

The method of decompressive craniotomy with the device shown in FIGS. 19 and 20 is illustrated in FIGS. 26 and 27. FIG. 26 illustrates the cranial fixation device 71 in place attached to the bone flap 65 with screw 70 and attached to the skull 68 with screw 69. The brain 67 and dura 66 are shown in their normal position. Typically two or more of the cranial fixation devices 71 and 72 would be placed to fixate the bone flap 65 to the skull 68 with the cranial fixation device telescopes in a retracted position approximating the bone flap to the skull. As shown in FIG. 27, with the development of brain swelling or an increase in intracranial pressure from a hemorrhage, the swollen brain 73 pushes against the bone flap 65. The pressure on the bone flap places the cranial fixation device 71 telescopes 47 and 49 in an extended position thereby allowing the head 44 attached to the bone flap to move outwards relative to the head 43 attached to the skull and accommodate the brain swelling. The dural closure material 74 is preferably a collagen matrix that allows expansion but is not necessary. The dura can be left open or other dural substitutes made from autograft, allograft, or xenograft material can also be used. Once the brain swelling subsides, the bone flap moves back in towards the skull but the overlap of the cranial fixation heads prevents the bone flap from moving inside the skull.

Figure 28:
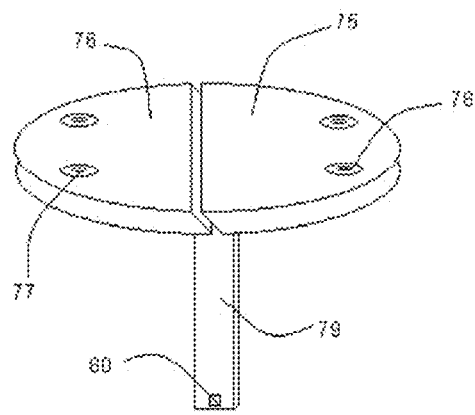
FIGS. 28 and 29 illustrate an exemplary cranial fixation device in accordance with an embodiment of the present invention.
Figure 29:
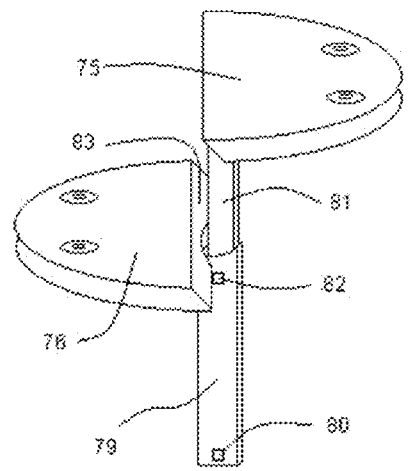
Figure 30:
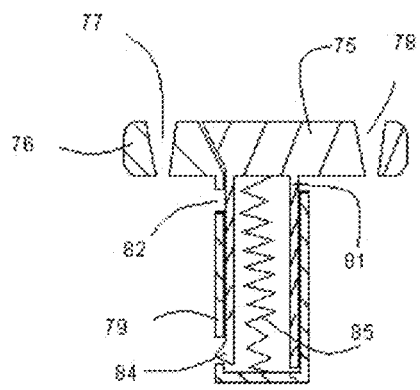
FIGS. 30 and 31 illustrate an exemplary cranial fixation device in accordance with an embodiment of the present invention.
Figure 31:
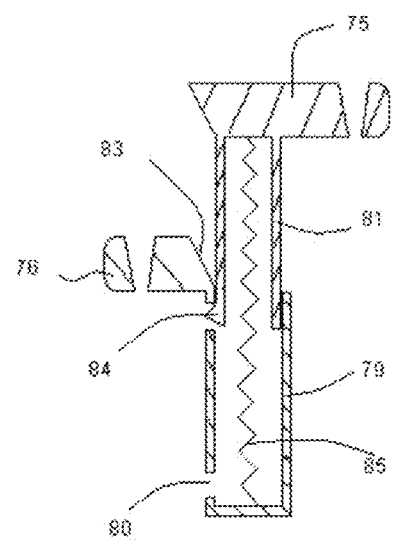
Figure 32:
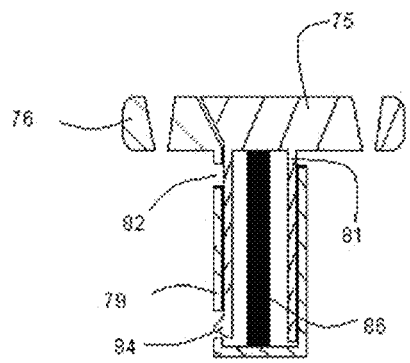
FIGS. 32 and 33 illustrate an exemplary cranial fixation device in accordance with an embodiment of the present invention.
Figure 33:
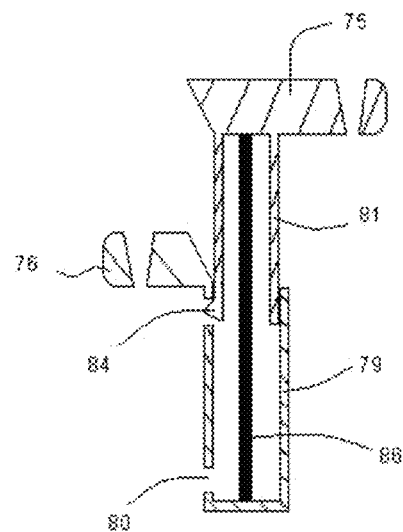

In another embodiment of the decompressive craniotomy device as shown in FIGS. 28-31, the head 76 comprises an extension 79 and the head 75 comprises an extension 81. The extensions 79 and 81 are telescopic and allow for inward or outward movement of the heads relative to each other. The medial edges of the heads 76 and 75 are sloped 83 and overlap each other when the heads are approximated, thereby not allowing the head 75 to move inward beyond the head 76. The head 76 has holes 77 which allows placement of screws attaching the head to the skull. Head 75 has holes 78 through which screws can be placed for attachment of the head to the bone flap. The spring 85 is attached to the head 75 at one end and the telescopic extension 79 at the other end. FIGS. 28 and 30 show the telescopic extensions in a compressed position whereby extension 81 is contained inside the extension 79 and FIGS. 29 and 31 show the extensions 81 and 79 in a distracted position. The telescopic extension 79 also comprises recesses 80 and 82 which engage with a ridge 84 on the telescopic extension 81. The recess 80 engages with ridge on the telescopic extension 81 in a completely retracted position and the recess 84 engages with the ridge 30 on the telescopic extension 81 in a completely extended position and therefore prevents the extension 81 from completely pulling out of the extension 79. In another embodiment as shown in FIGS. 32 and 33, the cranial fixation device comprises of an elastomeric cord 86 rather than a spring. In FIG. 32 the cord 86 is shown in a contracted position pulling the heads 75 and 76 together and in FIG. 33 the cord 86 is stretched due to an increase in ICP distracting the telescopic extensions and pushing the head 75 outwards relative to the head 76.

Figure 34:
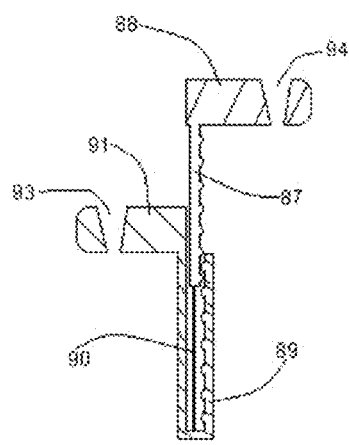
FIGS. 34 and 35 illustrate an exemplary cranial fixation device in accordance with an embodiment of the present invention.
Figure 35:
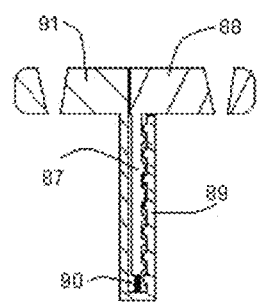

In another embodiment of the decompressive craniotomy device shown in FIGS. 34 and 35, the heads 88 and 91 each contain a telescopic extension 87 and 89. The extension 89 houses the extension 87 which are connected with an elastomeric cord 90. The telescopic extensions 87 and 89 also comprise ridges that engage with each other. The head 88 comprises of holes 94 for placement of screws to attach to the bone flap. The head 91 comprises of holes 93 for placement of screw to attach to the skull. FIG. 34 shows the distracted position of the telescopic extensions 87 and 89 with the head 88 pushed outwards by an increase in ICP. The elastomeric cord 90 is stretched and once the ICP normalizes the cord 90 pulls the head 88 inwards and places the telescopic extensions in a retracted position as shown in FIG. 35.

Figure 36:
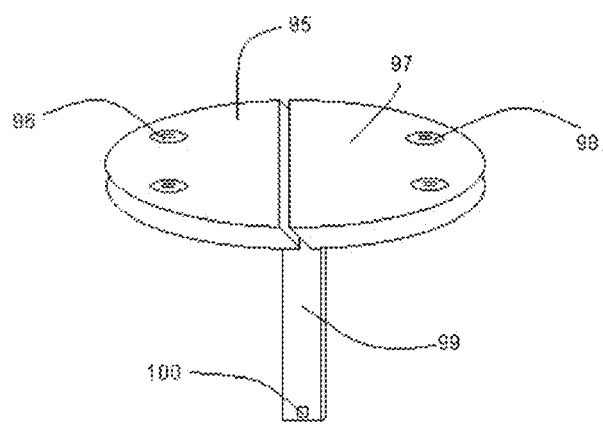
FIGS. 36 through 39 illustrate an exemplary cranial fixation device in accordance with an embodiment of the present invention.
Figure 37:
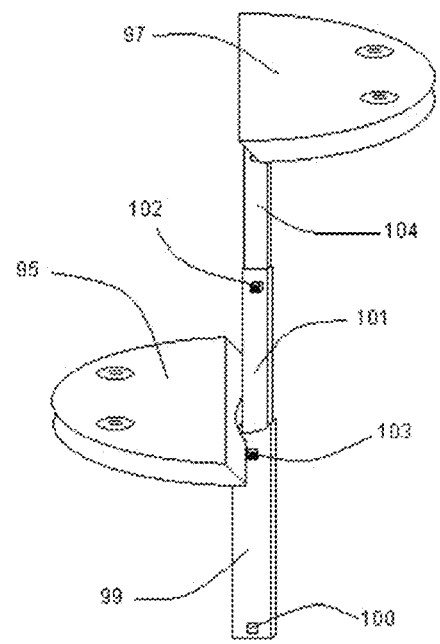
Figure 38:
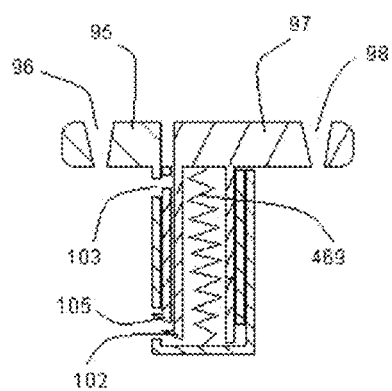
Figure 39:
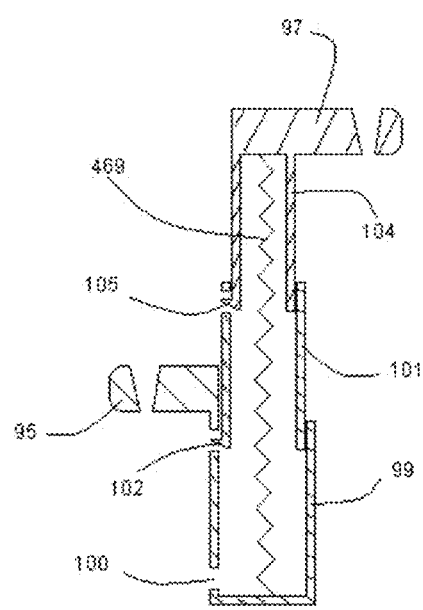

In another embodiment of the decompressive craniotomy device as shown in FIGS. 36-39, the head 95 comprises an extension 99 and the head 97 comprises an extension 104. An intermediate telescopic extension 101 connects the extensions 99 and 104. The telescopic extensions allow for inward or outward movement of the heads relative to each other. The head 95 has holes 96 which allows placement of screws attaching the head to the skull. Head 97 has holes 98 through which screws can be placed for attachment of the head to the bone flap. FIGS. 36 and 38 show the telescopic extensions in a retracted position whereby extensions 101 and 104 are contained inside the extension 99 and FIGS. 37 and 39 show the extensions 101 and 104 in a distracted position. The telescopic extension 99 also comprises recesses 100 and 103 which engage with a ridge 102 on the telescopic extension 101. The recess 100 engages with ridge 102 on the telescopic extension 101 along with ridge 105 on the telescopic extension 104 in a completely retracted position. The recess 41 engages with the ridge 102 on the telescopic extension 101 in an extended position and prevents the extension 101 from completely pulling out of the extension 99. The telescopic extension 101 also comprises of a recess which engages a ridge 102 on the telescopic extension 104 in an extended position as shown in FIG. 39. In a retracted position as seen in FIG. 38 the ridge 105 engages with the ridge 102 and maintains the telescopes in that position.

Figure 40:
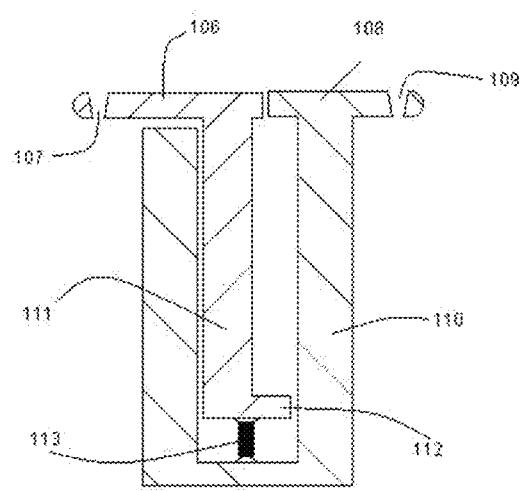
FIGS. 40 and 41 illustrate an exemplary cranial fixation device in accordance with an embodiment of the present invention.
Figure 41:
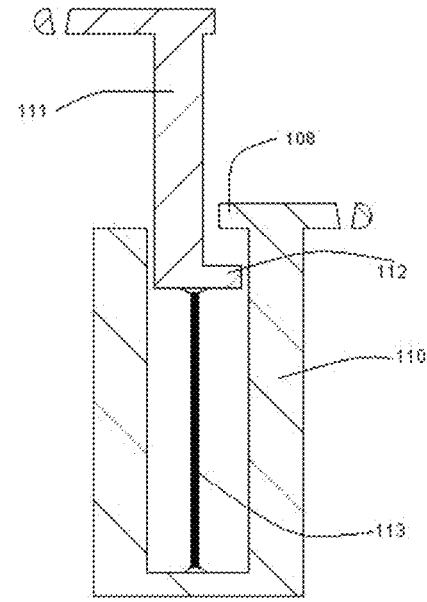
Figure 42:
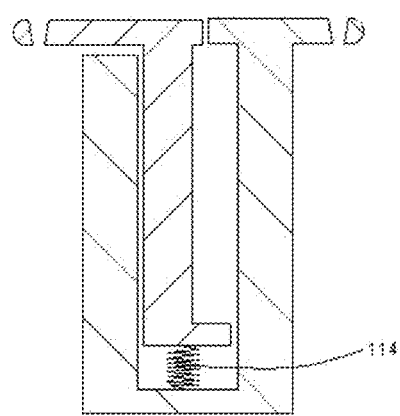
FIGS. 42 and 43 illustrate an exemplary cranial fixation device in accordance with an embodiment of the present invention.
Figure 43:
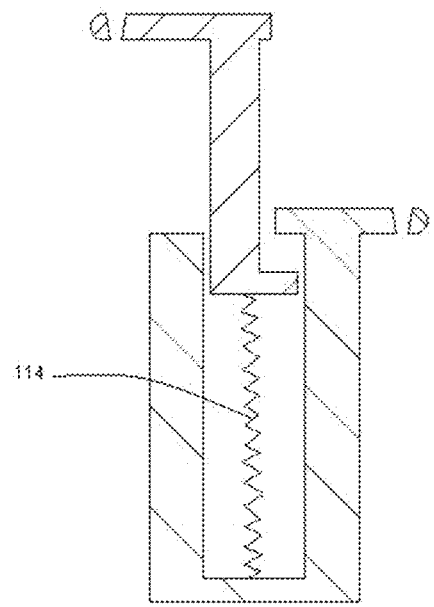

In another embodiment of the decompressive craniotomy device as shown in FIGS. 40 and 41, the head 106 comprises an extension 111 and the head 108 comprises an extension 110. The head 108 has holes 109 which allows placement of screws attaching the head to the skull. Head. 106 has holes 107 through which screws can be placed for attachment of the head to the bone flap. The extensions 110 and 111 are telescopic and connected with an elastomeric cord 113 that allow for constrained inward or outward movement of the heads relative to each other. The telescopic extension 111 also comprises an extension 112 at one end. FIG. 40 shows the telescopic extensions 110 and 111 in a compressed position. FIG. 41 shows the extensions 110 and 111 in a distracted position with the extension 112 preventing the telescopic extension 111 from pulling out of the telescopic component 110. Another embodiment of the decompressive craniotomy device described above in FIGS. 40 and 41 is shown in FIGS. 42 and 43. The device comprises of a spring 114 instead of an elastomeric band.

Figure 44:
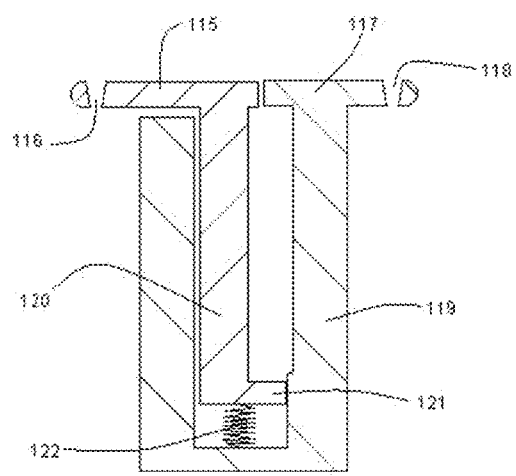
FIGS. 44 and 45 illustrate an exemplary cranial fixation device in accordance with an embodiment of the present invention.
Figure 45:
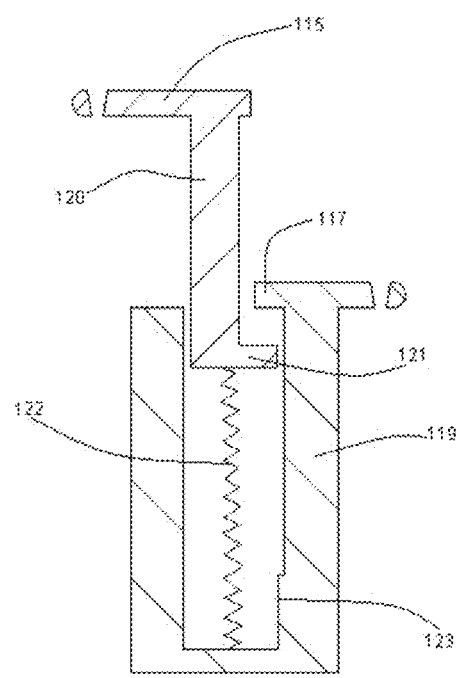
Figure 46:
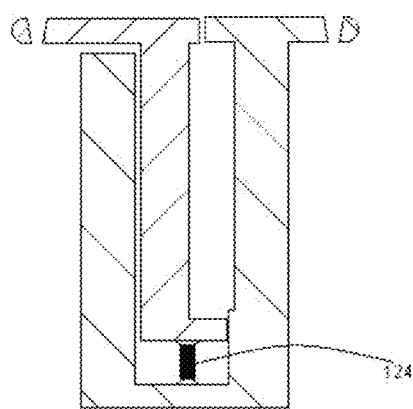
FIGS. 46 and 47 illustrate an exemplary cranial fixation device in accordance with an embodiment of the present invention.
Figure 47:
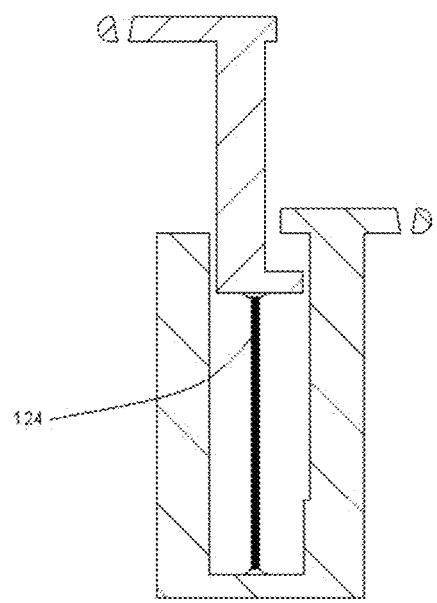

In another embodiment of the decompressive craniotomy device as shown in FIGS. 44 and 45, the head 115 comprises an extension 120 and the head 117 comprises an extension 119. The head 117 has holes 118 which allows placement of screws attaching the head to the skull. Head 115 has holes 116 through which screws can be placed for attachment of the head to the bone flap. The extensions 119 and 120 are telescopic and connected with a contraction spring 122 that allow for constrained inward or outward movement of the heads relative to each other. The telescopic extension 120 also comprises an extension 121 at one end. FIG. 44 shows the telescopic extensions 119 and 120 in a compressed position. The extension 121 engages with an enlargement 123 in the distal end of the telescopic component 119 to maintain the compressed position. FIG. 45 shows the extensions 119 and 120 in a distracted position with the extension 121 preventing the telescopic extension 120 from pulling out of the telescopic component 119. Another embodiment of the decompressive craniotomy device described above in FIGS. 44 and 45 is shown in FIGS. 46 and 47. The device comprises of an elastomeric cord 124 instead of a spring.

Figure 48:
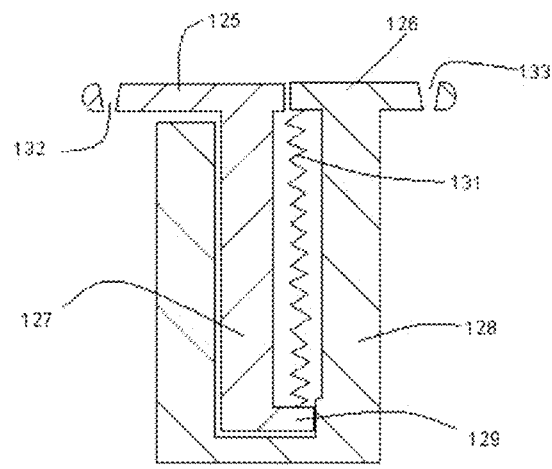
FIGS. 48 and 49 illustrate an exemplary cranial fixation device in accordance with an embodiment of the present invention.
Figure 49:
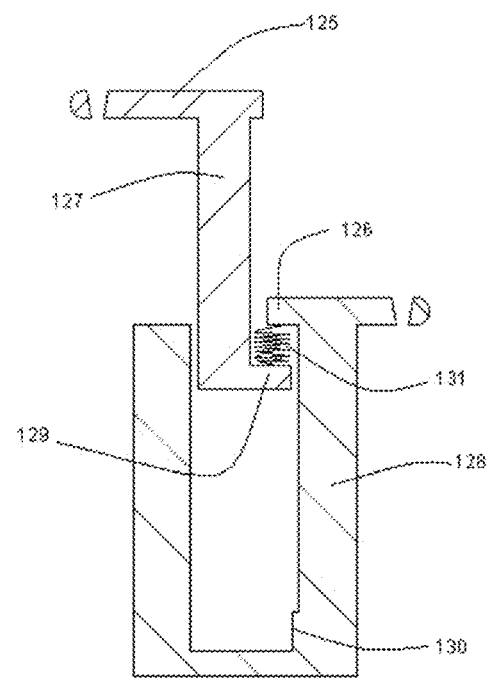

In another embodiment of the decompressive craniotomy device as shown in FIGS. 48 and 49, the head 125 comprises an extension 127 and the head 126 comprises an extension 128. The head 126 has holes 133 which allows placement of screws attaching the head to the skull. Head 125 has holes 132 through which screws can be placed for attachment of the head to the bone flap. The extensions 127 and 128 are telescopic and allow for inward or outward movement of the heads relative to each other. The telescopic extension 127 also comprises an extension 129 at one end. The extension 129 is connected to a distraction spring 131 which is connected to the head 126 at the other end. The distraction spring forces the heads together by pushing the extension 129 away from the head 126. FIG. 48 shows the telescopic extensions 127 and 128 in a compressed position. The extension 129 engages with an enlargement 130 in the distal end of the telescopic component 128 to maintain the compressed position. FIG. 49 shows the extensions 127 and 128 in a distracted position with the extension 129 preventing the telescopic extension 127 from pulling out of the telescopic component 128.

Figure 50:
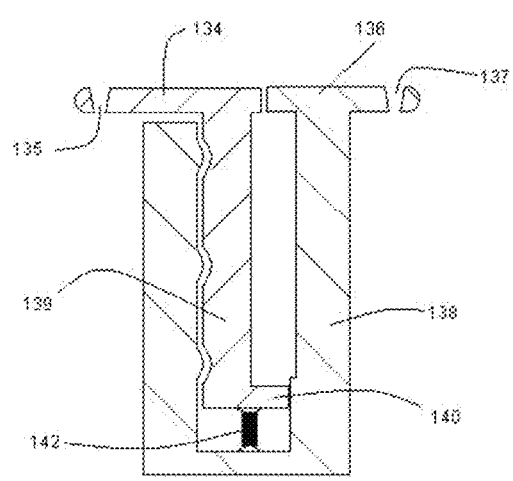
FIGS. 50 and 51 illustrate an exemplary cranial fixation device in accordance with an embodiment of the present invention.
Figure 51:
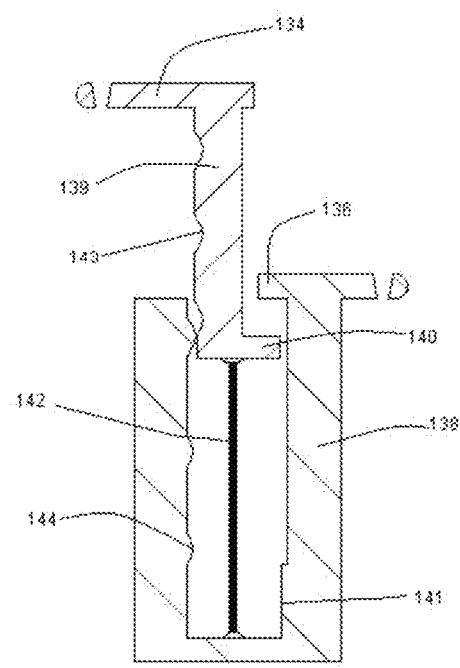
Figure 52:
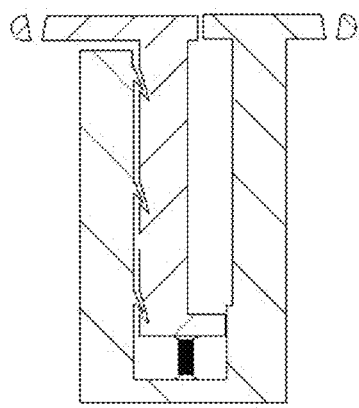
FIGS. 52 and 53 illustrate an exemplary cranial fixation device in accordance with an embodiment of the present invention.
Figure 53:
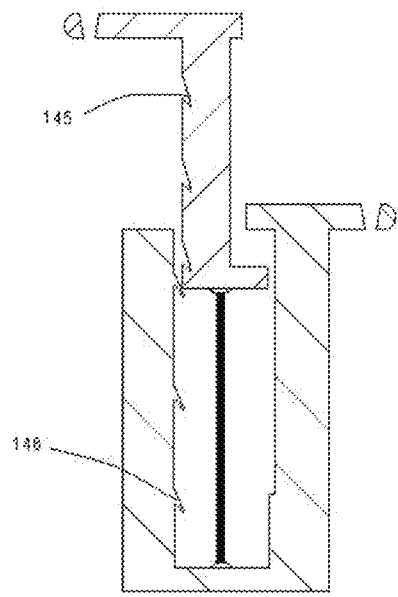

In another embodiment of the decompressive craniotomy device as shown in FIGS. 50 and 51, the head 134 comprises an extension 139 and the head 136 comprises an extension 138. The head 136 has holes 137 which allows placement of screws attaching the head to the skull. Head 134 has holes 135 through which screws can be placed for attachment of the head to the bone flap. The extensions 138 and 139 are telescopic and connected with an elastomeric cord 142 that allow for constrained inward or outward movement of the heads relative to each other. The telescopic extensions 138 and 139 comprise of ridges 144 and sockets 143 that engage in different telescopic compression and distraction positions. The telescopic extension 139 also comprises an extension 140 at one end. FIG. 50 shows the telescopic extensions 138 and 139 in a compressed position. The extension 140 engages with an enlargement 141 in the distal end of the telescopic component 138 to maintain the compressed position. FIG. 51 shows the extensions 138 and 139 in a distracted position with the extension 140 preventing the telescopic extension 139 from pulling out of the telescopic component 138. Another embodiment of the decompressive craniotomy device described above in FIGS. 50 and 51 is shown in FIGS. 52 and 53. The device comprises of ratchet teeth 145 and 146 in the telescopic extensions instead of ridges.

Figure 54:
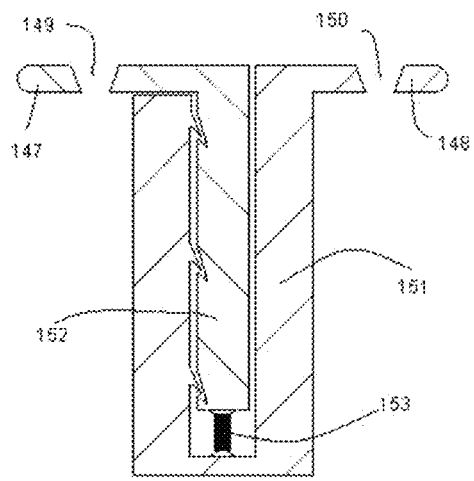
FIGS. 54 and 55 illustrate an exemplary cranial fixation device in accordance with an embodiment of the present invention.
Figure 56:
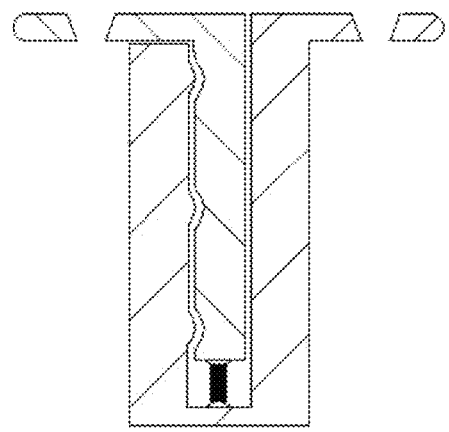
FIGS. 56 and 57 illustrate an exemplary cranial fixation device in accordance with an embodiment of the present invention.
Figure 55:
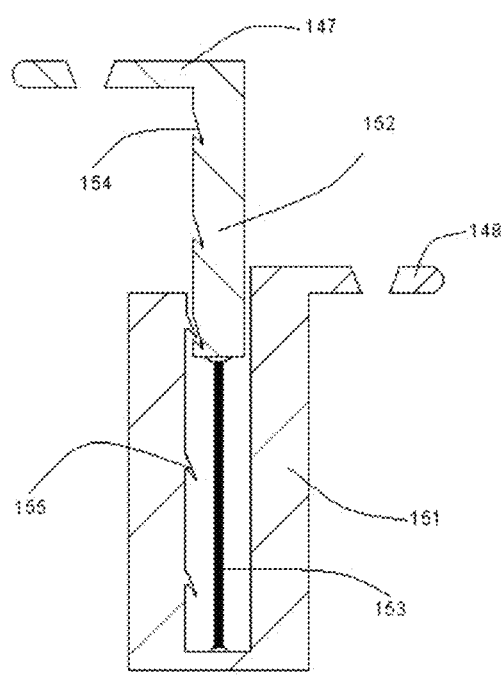
Figure 57:
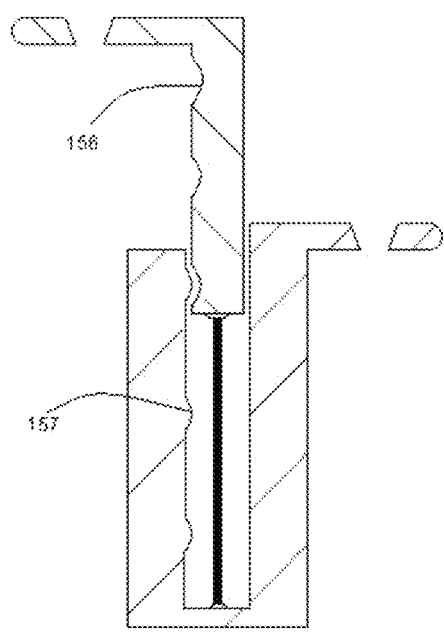
Figure 58:
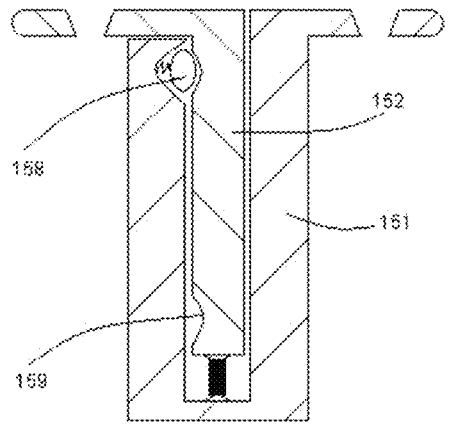
FIGS. 58 and 59 illustrate an exemplary cranial fixation device in accordance with an embodiment of the present invention.
Figure 60:
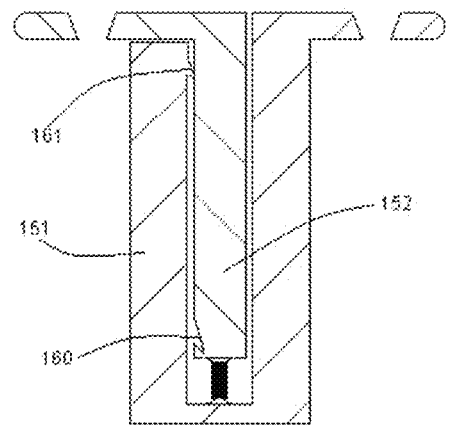
FIGS. 60 and 61 illustrate an exemplary cranial fixation device in accordance with an embodiment of the present invention.
Figure 59:
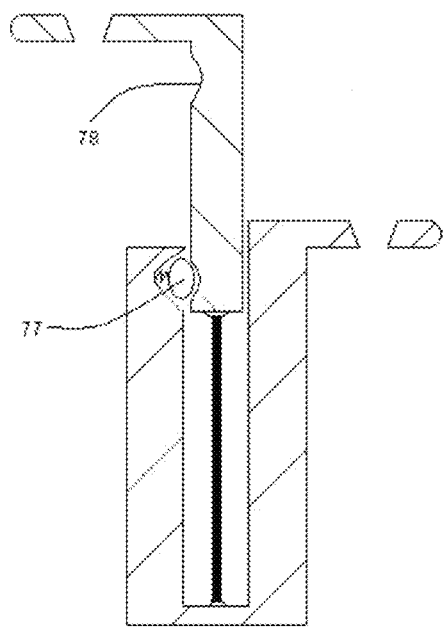
Figure 61:
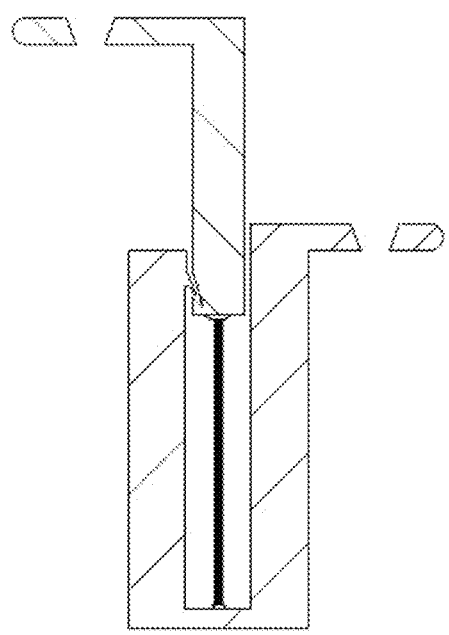

In another embodiment of the decompressive craniotomy device shown in FIGS. 54 and 55, the heads 147 and 148 each contain a telescopic extension 152 and 151. The extension 151 houses the extension 152 which are connected with an elastomeric cord 153. The telescopic extensions 151 and 152 also comprise of multiple ratchet teeth 155 and 154 respectively that engage with each other. The head 147 comprises of holes 149 for placement of screws to attach to the bone flap. The head 148 comprises of holes 150 for placement of screw to attach to the skull. FIG. 55 shows the distracted position of the telescopic extensions 151 and 152 with the head 147 pushed outwards by an increase in ICP. The elastomeric cord 153 is stretched and once the ICP normalizes the cord 153 pulls the head 147 inwards and places the telescopic extensions in a retracted position as shown in FIG. 54. Another embodiment of the decompressive craniotomy device described above in FIGS. 54 and 55 is shown in FIGS. 56 and 57. The device comprises of ridges 157 and 156 in the telescopic extensions instead of ratchet teeth. In another embodiment of the decompressive craniotomy device described above in FIGS. 56 and 57 is shown in FIGS. 58 and 59. The device comprises of a ball 158 and socket 159 engaging mechanism in the telescopic extensions 151 and 152 instead of ratchet teeth. The telescopic extension 152 contains recesses 159 at the proximal and distal ends that engage with the ball 158 at the proximal end of the telescopic housing portion 151. FIG. 58 shows the ball and socket mechanism engaged in a compressed position and FIG. 59 shows the ball and socket mechanism engaged in a distracted position. In yet another embodiment of the decompressive craniotomy device described above in FIGS. 56 and 57 is shown in FIGS. 60 and 61. The device comprises of a single ratchet tooth 161 at the proximal end of the telescopic housing portion 151 that engages with a recess 160 at the distal end of the telescopic extension 152. FIG. 60 shows the ratchet tooth mechanism engaged in a compressed position and FIG. 61 shows the ratchet tooth mechanism disengaged in a distracted position.

Figure 62:
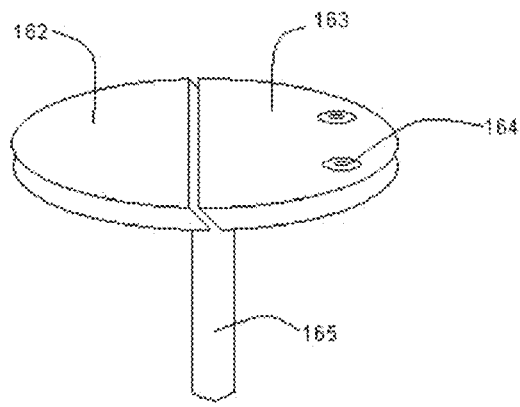
FIGS. 62 through 64 illustrate an exemplary cranial fixation device in accordance with an embodiment of the present invention.
Figure 63:
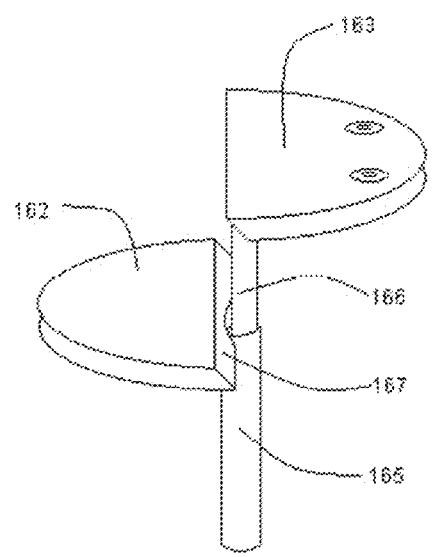
Figure 64:
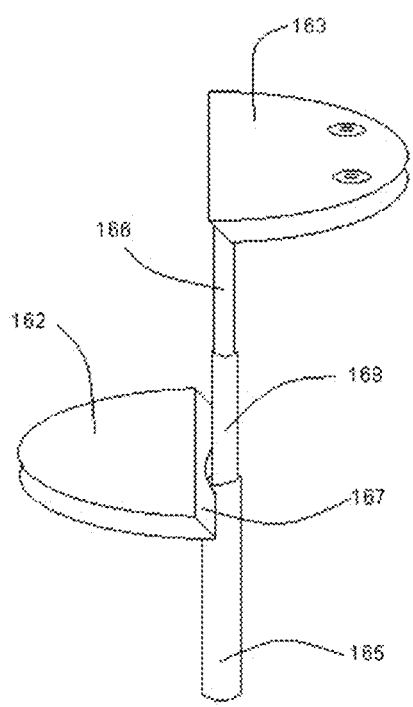

In another embodiment, the decompressive craniotomy device as shown in FIGS. 62 and 63 comprises a head 162 with an extension 165 and a head 163 with an extension 166. The extensions 165 and 166 are telescopic and allow for inward or outward movement of the heads relative to each other. The medial edges of the heads 162 and 163 are sloped 167 and overlap each other when the heads are approximated, thereby not allowing the head 163 to move inward beyond the head 162. The head 163 has holes 164 which allow placement of screws attaching the head to the bone flap and the head 162 rests on the outer surface of the skull. The extension 165 also houses a spring or an elastomeric cord connecting the telescopic extensions and/or the head 163. FIG. 62 shows the telescopic extensions in a compressed position whereby extension 166 is contained inside the extension 165 and FIG. 63 shows the extensions 166 and 165 in a distracted position. FIG. 64 illustrates another embodiment of the decompressive craniotomy device with an intermediate telescopic component 168 which allows the head 163 attached to the bone flap to move outwards further if needed to accommodate an increase in intracranial pressure or brain swelling.

Figure 65:
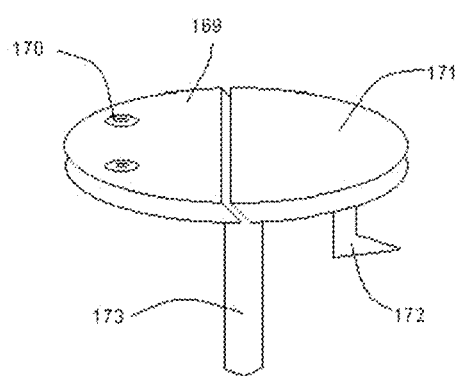
FIGS. 65 and 66 illustrate an exemplary cranial fixation device in accordance with an embodiment of the present invention.
Figure 66:
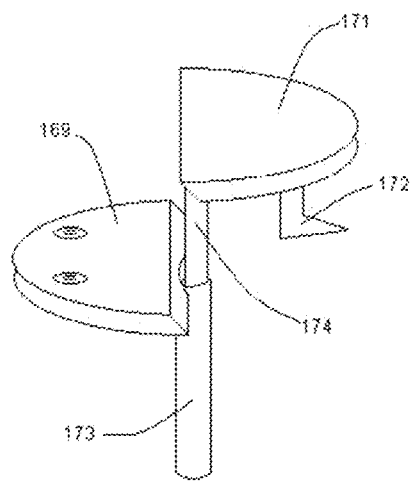

In another embodiment, the decompressive craniotomy device as shown in FIGS. 65 and 66 comprises a head 169 with an extension 173 and a head 171 with an extension 174. The extensions 173 and 174 are telescopic and allow for inward or outward movement of the heads relative to each other. The head 169 has holes 170 which allow placement of screws attaching the head to the skull and the head 171 has a clamp 172 that attaches to the diploe of the bone flap and the head 171 rests on the outer surface of the bone flap. The extension 173 also houses a spring or an elastomeric cord connecting the telescopic extensions and/or the head 171. FIG. 65 shows the telescopic extensions in a compressed position whereby extension 174 is contained inside the extension 173 and FIG. 66 shows the extensions 173 and 174 in a distracted position.

Figure 67:
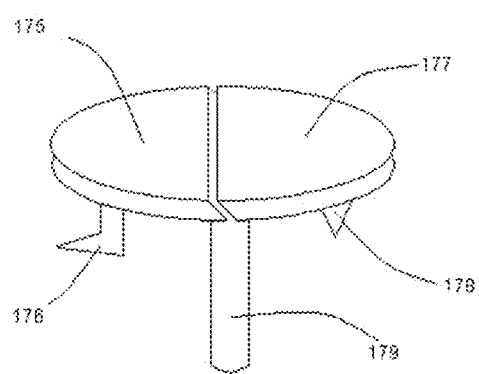
FIGS. 67 and 68 illustrate an exemplary cranial fixation device in accordance with an embodiment of the present invention.
Figure 68:
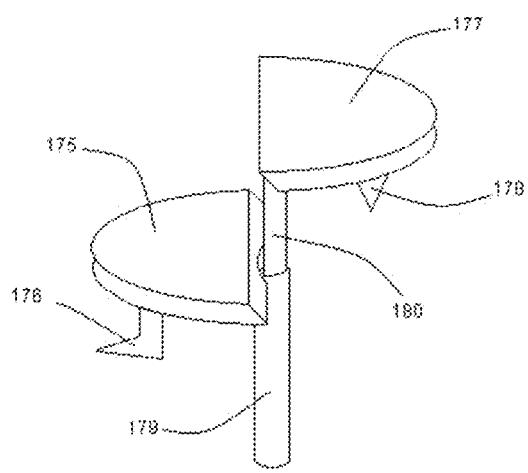

In another embodiment, the decompressive craniotomy device as shown in FIGS. 67 and 68 comprises a head 175 with an extension 179 and a head 177 with an extension 180. The extensions 179 and 180 are telescopic and allow for inward or outward movement of the heads relative to each other. The head 175 has a clamp 176 that secures the head to the skull and the head 177 has spikes 178 that attach to the bone flap. The extension 179 also houses a spring or an elastomeric cord connecting the telescopic extensions and/or the head 177. FIG. 67 shows the telescopic extensions in a compressed position whereby extension 180 is contained inside the extension 179 and FIG. 68 shows the extensions 179 and 180 in a distracted position.

Figure 69:
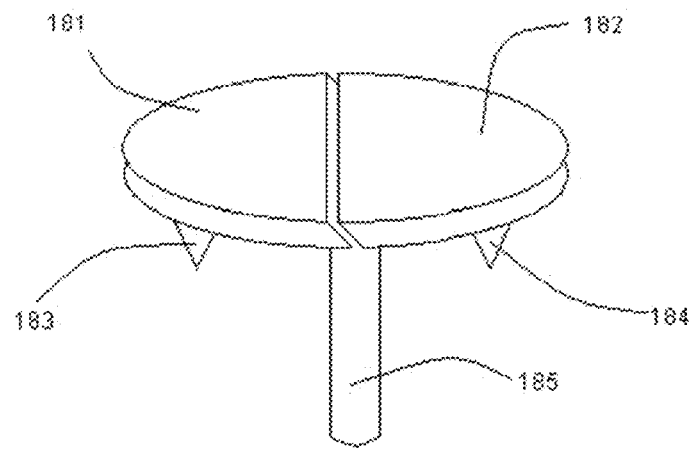
FIGS. 69 and 70 illustrate an exemplary cranial fixation device in accordance with an embodiment of the present invention.
Figure 70:
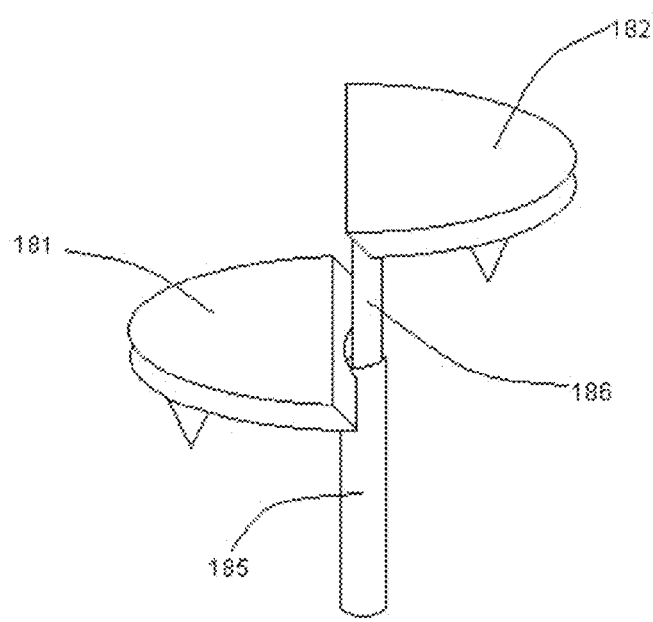

In another embodiment of the decompressive craniotomy device as shown in FIGS. 69 and 70, the head 181 comprises an extension 185 and the head 182 comprises an extension 186. The extensions 185 and 186 are telescopic and allow for inward or outward movement of the heads relative to each other. The heads 181 and 182 also comprise of spikes 183 and 184 that attach to the skull and bone flap respectively. The extension 185 also houses a spring or an elastomeric cord connecting the telescopic extensions and/or the head 182. FIG. 69 shows the telescopic extensions in a compressed position whereby extension 186 is contained inside the extension 185 and FIG. 47 shows the extensions 185 and 186 in a distracted position.

Figure 71:
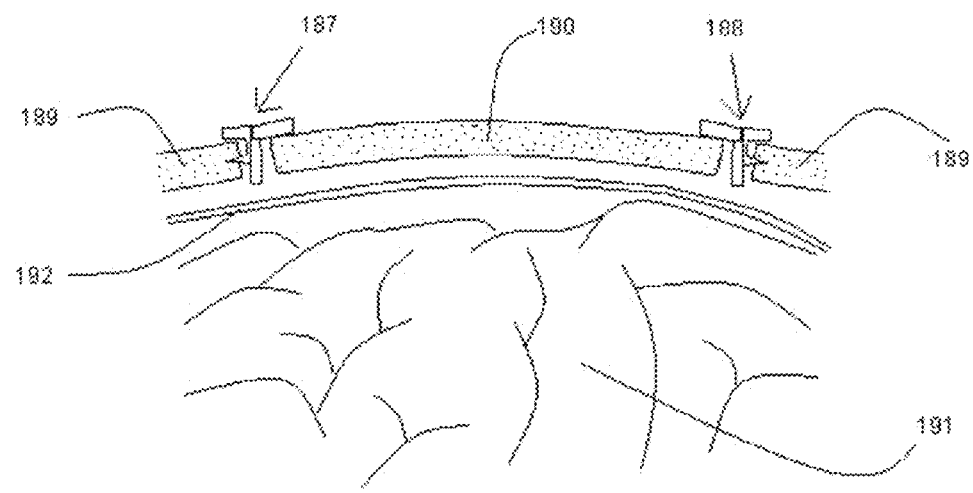
FIGS. 71 and 72 are cross sectional side views of exemplary cranial fixation devices attached to a skull and a bone flap for a decompressive craniotomy, in accordance with an embodiment of the present invention.
Figure 72:
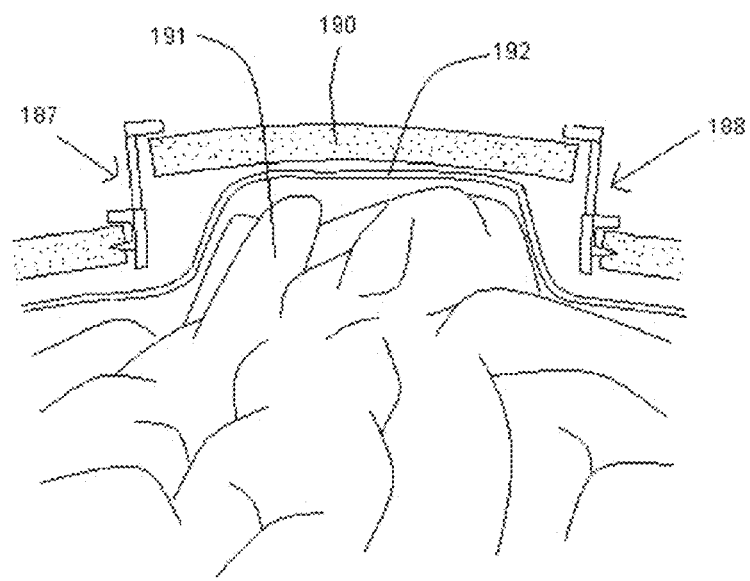

The method of decompressive craniotomy with the device in FIGS. 67 and 68 is illustrated in FIGS. 71 and 72. FIG. 71 shows the cranial fixation devices 187 and 188 in place attached to the outer surface of the bone flap 190 and the skull 189 and 190. The brain 191 and dura 192 are shown in their normal position. Typically two or more of the cranial fixation devices would be placed to fixate the bone flap 190 to the skull 189 and 190 with the device telescopes in a retracted position approximating the bone flap to the skull. As shown in FIG. 72, with the development of brain swelling or an increase in intracranial pressure from a hemorrhage, the brain 191 and dura 192 push against the bone flap 190. The pressure on the bone flap places the cranial fixation device 187 and 188 telescopes in an extended position thereby allowing the bone flap to move outwards and accommodate the brain swelling.

While the abovementioned cranial fixation device heads are positioned on the outer surface of the skull and bone flap, in other embodiments one head is positioned on the outer surface of the skull and/or bone flap and the other head is positioned on the inner surface. The head shapes can be rectangular or circular.

Figure 73:
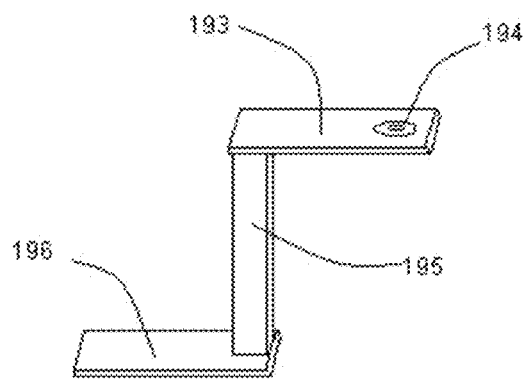
FIGS. 73 and 74 illustrate an exemplary cranial fixation device in accordance with an embodiment of the present invention.
Figure 74:
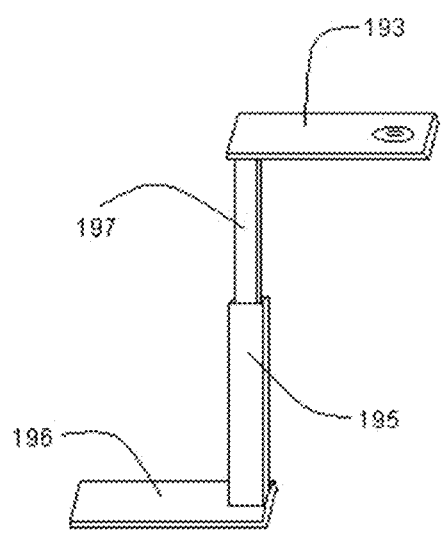
Figure 75:
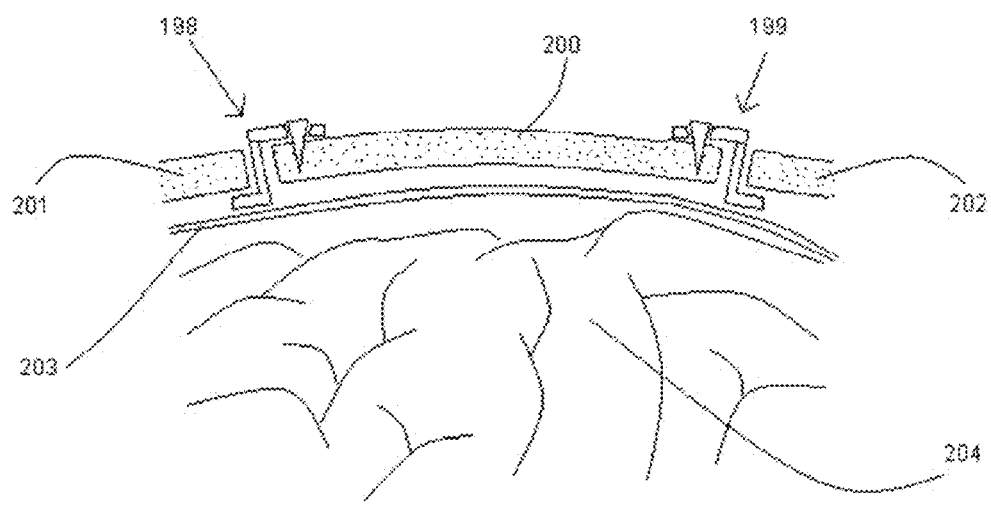
FIGS. 75 and 76 are cross sectional side views of exemplary cranial fixation devices attached to a skull and a bone flap for a decompressive craniotomy, in accordance with an embodiment of the present invention.
Figure 76:
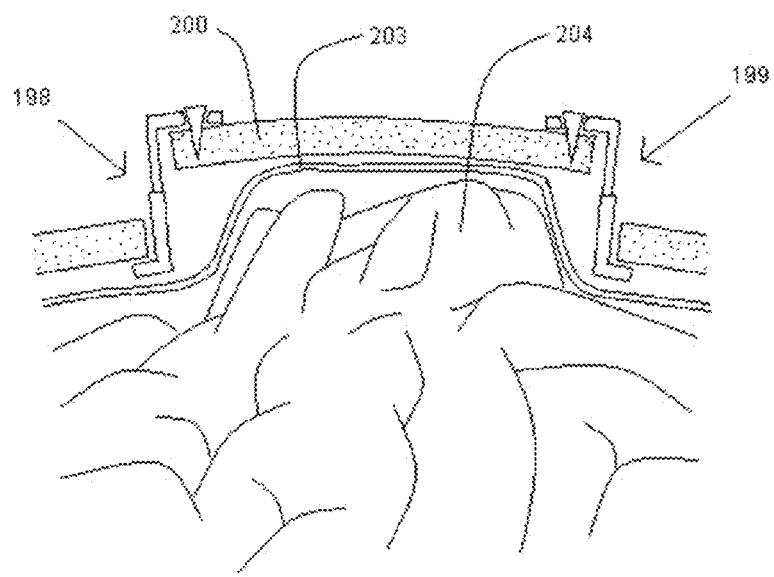

As shown in FIGS. 73 and 74 the head 193 rests on the outer surface of the bone flap and comprises a hole 194 for placement of a screw and a telescopic extension 197. The head 196 is positioned on the inner surface of the skull and comprises a telescopic housing extension 195. The extension 195 also houses a spring or an elastomeric cord connecting the telescopic extensions and/or the heads. FIG. 73 shows the telescopic extensions in a compressed position whereby extension 197 is contained inside the extension 195 and FIG. 74 shows the extensions 195 and 197 in a distracted position. The method of decompressive craniotomy with the device in FIGS. 73 and 74 is illustrated in FIGS. 75 and 76. FIG. 75 shows the devices 198 and 199 in place attached to the outer surface of the bone flap 200 with screws and the inner surface of the skull 201 and 202. The brain 204 and dura 203 are shown in their normal position. Typically two or more of the cranial fixation devices would be placed to fixate the bone flap 200 to the skull 201 and 202 with the cranial fixation device telescopes in a retracted position approximating the bone flap to the skull. As shown in FIG. 76, with the development of brain swelling or an increase in intracranial pressure from a hemorrhage, the swollen brain 204 and dura 203 push against the bone flap 200. The pressure on the bone flap places the cranial fixation device 198 and 199 telescopes in an extended position thereby allowing the bone flap to move outwards and accommodate the brain swelling.

Figure 77:
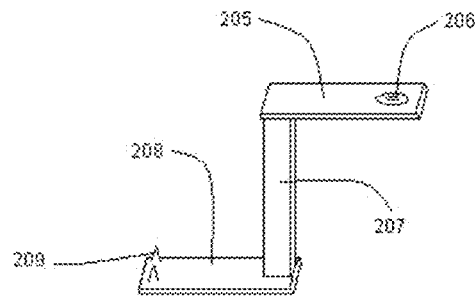
FIGS. 77 and 78 illustrate an exemplary cranial fixation device in accordance with an embodiment of the present invention.
Figure 78:
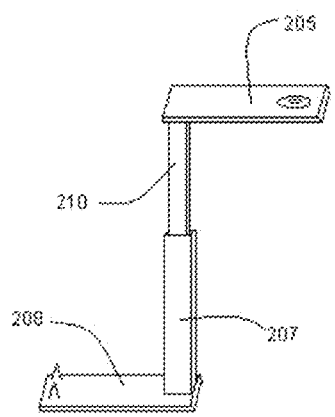

In another embodiment of the decompressive craniotomy device as shown in FIGS. 77 and 78 the head 205 rests on the outer surface of the bone flap and comprises a hole 206 for placement of a screw and a telescopic extension 210. The head 208 is attached to the inner surface of the skull with spikes 209 and comprises a telescopic housing extension 207. The extension 207 also houses a spring or an elastomeric cord connecting the telescopic extensions and/or the heads. FIG. 77 shows the telescopic extensions in a compressed position whereby extension 210 is contained inside the extension 207 and FIG. 78 shows the extensions 207 and 210 in a distracted position.

Figure 79:
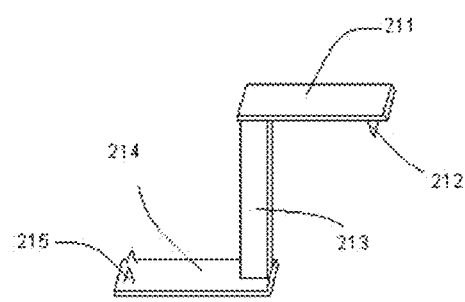
FIGS. 79 and 80 illustrate an exemplary cranial fixation device in accordance with an embodiment of the present invention.
Figure 80:
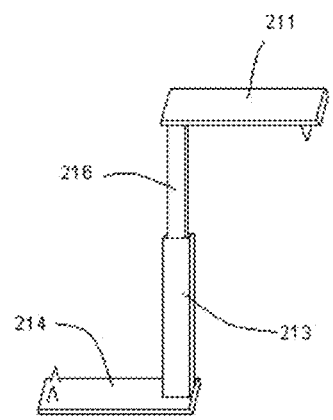
Figure 81:
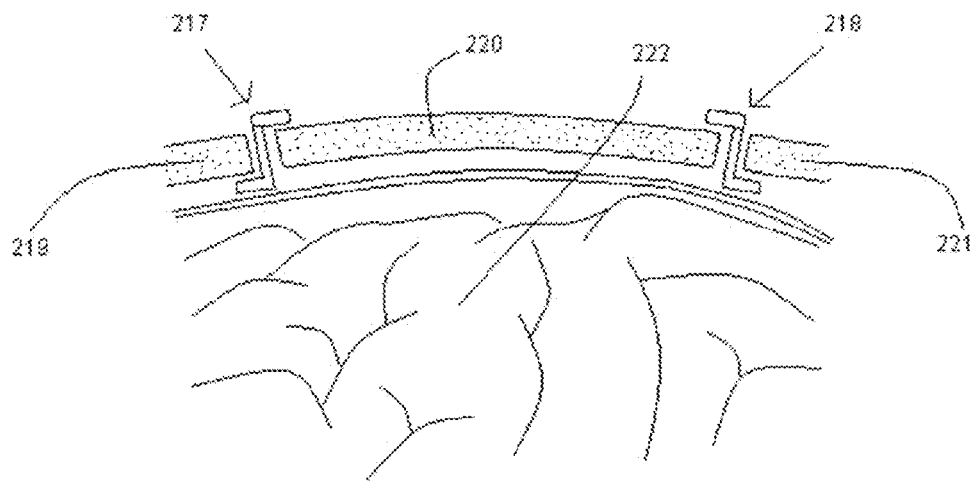
FIGS. 81 and 82 are cross sectional side views of exemplary cranial fixation devices attached to a skull and a bone flap for a decompressive craniotomy, in accordance with an embodiment of the present invention.
Figure 82:
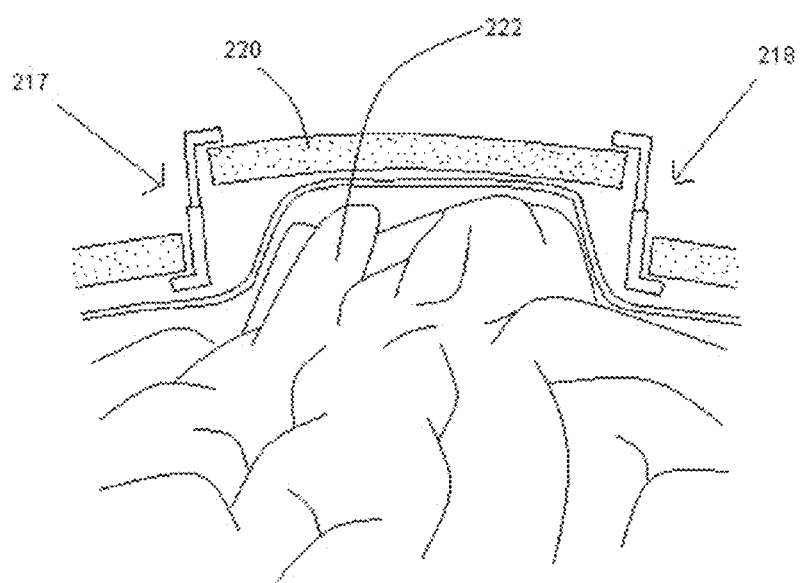

In another embodiment of the cranial fixation device as shown in FIGS. 79 and 80 the head 211 is attached to the outer surface of the bone flap with spikes 212 and comprises a telescopic extension 216. The head 214 is attached to the inner surface of the skull with spikes 215 and comprises a telescopic housing extension 213. The extension 213 also houses a spring or an elastomeric cord connecting the telescopic extensions and/or the heads. FIG. 79 shows the telescopic extensions in a compressed position whereby extension 216 is contained inside the extension 213 and FIG. 80 shows the extensions 213 and 216 in a distracted position. The method of decompressive craniotomy with the device in FIGS. 79 and 80 is illustrated in FIGS. 81 and 82. FIG. 81 illustrates the cranial fixation devices 217 and 218 in place attached to the outer surface of the bone flap 220 and the inner surface of the skull 219 and 221. The brain 222 is shown in its normal position. Typically two or more of the cranial fixation devices would be placed to fixate the bone flap 220 to the skull 219 and 221 with the cranial fixation device telescopes in a retracted position approximating the bone flap to the skull. As shown in FIG. 82, with the development of brain swelling or an increase in intracranial pressure from a hemorrhage, the swollen brain 222 pushes against the bone flap 220. The pressure on the bone flap places the cranial fixation device 217 and 218 telescopes in an extended position thereby allowing the bone flap to move outwards and accommodate the brain swelling.

Figure 85:
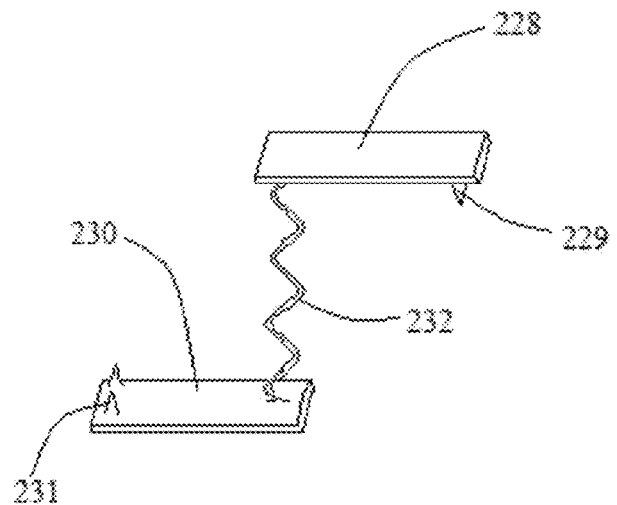
FIGS. 85 and 86 illustrate an exemplary cranial fixation device in accordance with an embodiment of the present invention.
Figure 86:
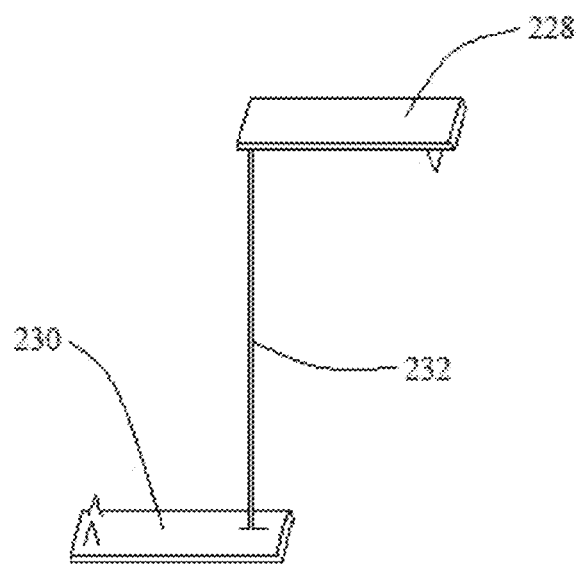

In another embodiment of the cranial fixation device as shown in FIGS. 85 and 86 the head 228 is attached to the outer surface of the bone flap with spikes 229. The head 230 is attached to the inner surface of the skull with spikes 231. The heads 228 and 230 are connected with an elastomeric cord 232. FIG. 85 shows the elastomeric cord 232 in a contracted position and FIG. 86 shows the elastomeric cord 232 stretched with heads 228 and 231 in a distracted position.

Figure 87:
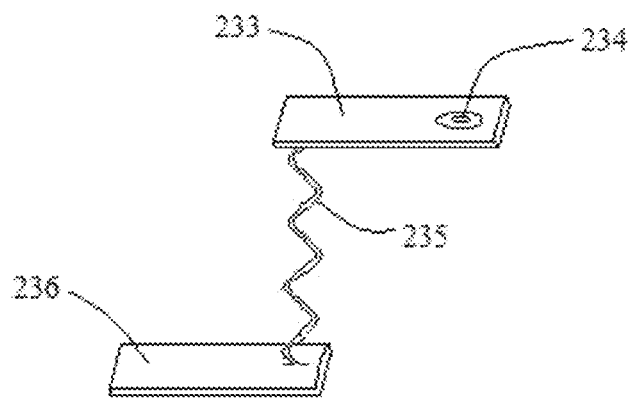
FIGS. 87 and 88 illustrate an exemplary cranial fixation device in accordance with an embodiment of the present invention.
Figure 88:
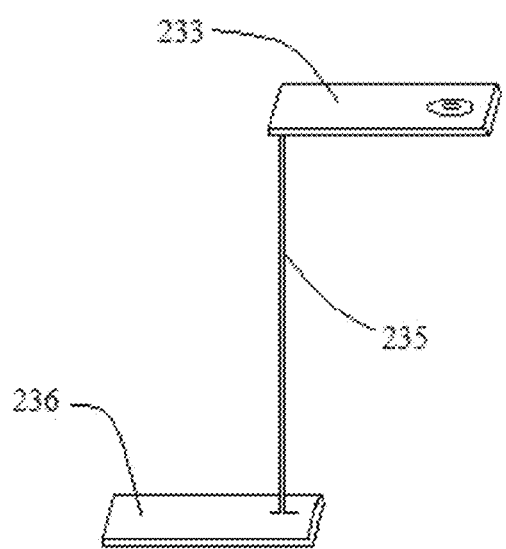

In another embodiment of the cranial fixation device as shown in FIGS. 87 and 88 the head 233 is attached to the outer surface of the bone flap with a screw placed through the hole 234. The head 236 is attached to the inner surface of the skull. The heads 233 and 236 are connected with an elastomeric cord 235. FIG. 87 shows the elastomeric cord 235 in a contracted position and FIG. 88 shows the elastomeric cord 235 stretched with heads 233 and 236 in a distracted position.

Figure 89:
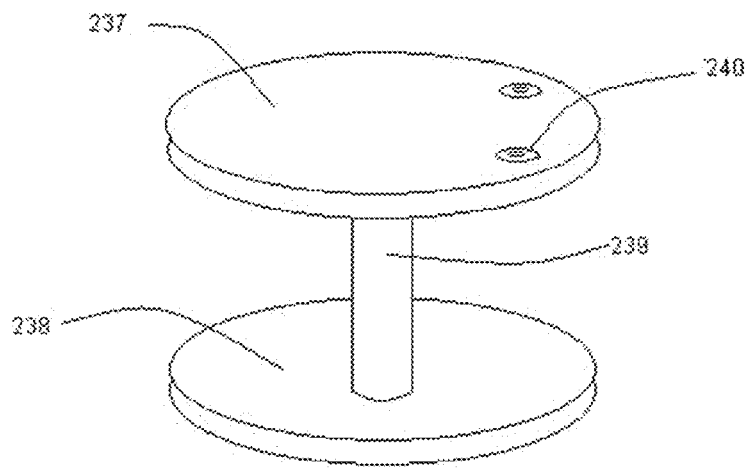
FIGS. 89 and 90 illustrate an exemplary cranial fixation device in accordance with an embodiment of the present invention.
Figure 90:
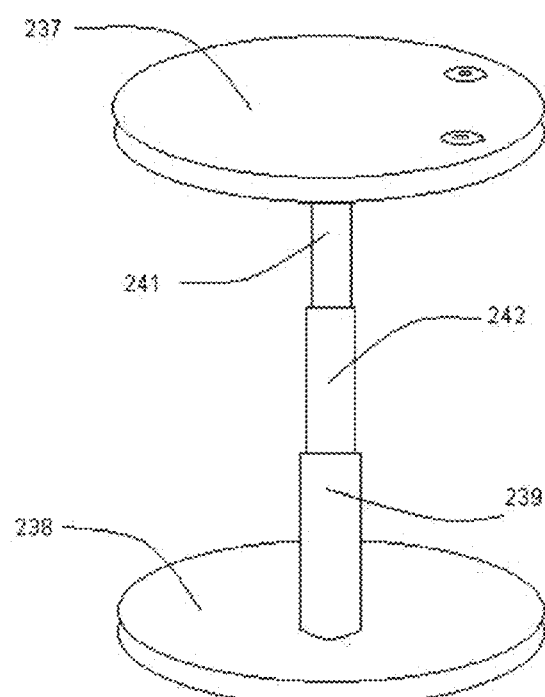

In another embodiment of the decompressive craniotomy device as shown in FIGS. 89 and 90, the device comprises of a head 237 and a head 238 connected with a telescopic portion 239. The head 237 resting on the outer surface of the bone flap and skull also comprising of holes 240 for screw placement. The side of the head 237 with screw holes 240 is secured to the bone flap and the opposing side of the head 237 rests on the skull. The head 238 rests on the inner surface of the skull and bone flap and the telescopic portion 239 is positioned in the skull defect. The telescopic portion 239 also comprises of extensions 241 and 242 along with an elastomeric cord or spring that allow for inward and outward movement of the head 237 secured at one end to the bone flap. FIG. 89 shows the telescopic portions in a retracted position and FIG. 90 shows the heads positioned away from each other with the telescopic portions in an extended position.

Figure 91:
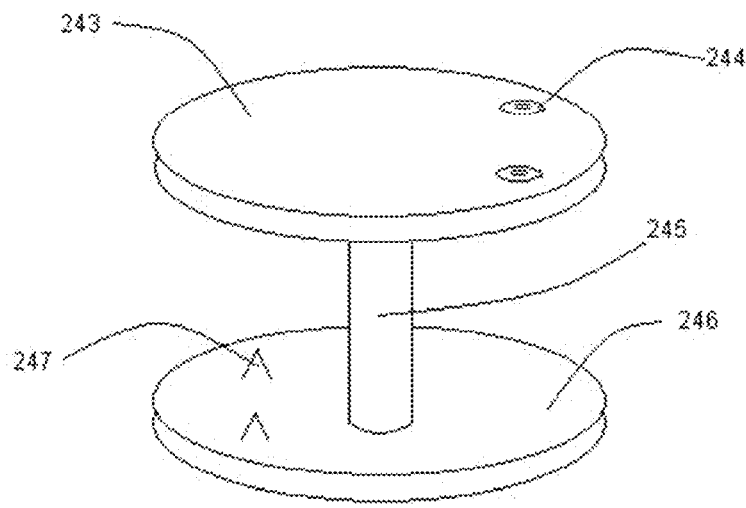
FIGS. 91 and 92 illustrate an exemplary cranial fixation device in accordance with an embodiment of the present invention.
Figure 92:
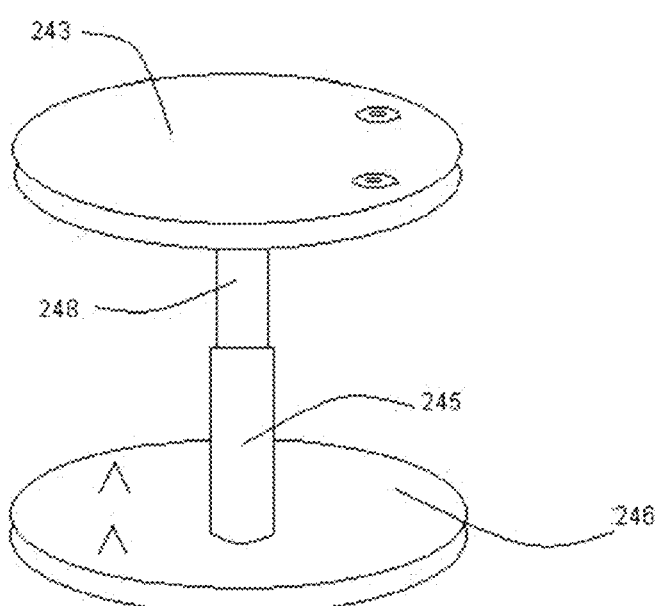

In another embodiment of the decompressive craniotomy device as shown in FIGS. 91 and 92, the device comprises of a head 243 and a head 246 connected with a telescopic portion 245. The head 243 resting on the outer surface of the bone flap and skull also comprises of holes 244 for screw placement. The side of the head 243 with screw holes 244 is secured to the bone flap and the opposing side of the head 243 rests on the skull. The head 246 rests on the inner surface of the skull and bone flap and the telescopic portion 245 is positioned in the skull burr hole opening. The side of the head 246 towards the skull comprises of spikes 247 for attachment to the inner surface of the skull. The telescopic portion 245 also comprises of extension 248 that allows outward movement of the head 243 secured at one end to the bone flap as shown in FIG. 92. The two heads or telescopic extensions are also connected with an elastomeric cord or spring that provides constrained inward and outward movement of the heads relative to each other. The spring or elastic cord can be positioned either inside the telescopic extensions or outside (not shown).

Figure 93:
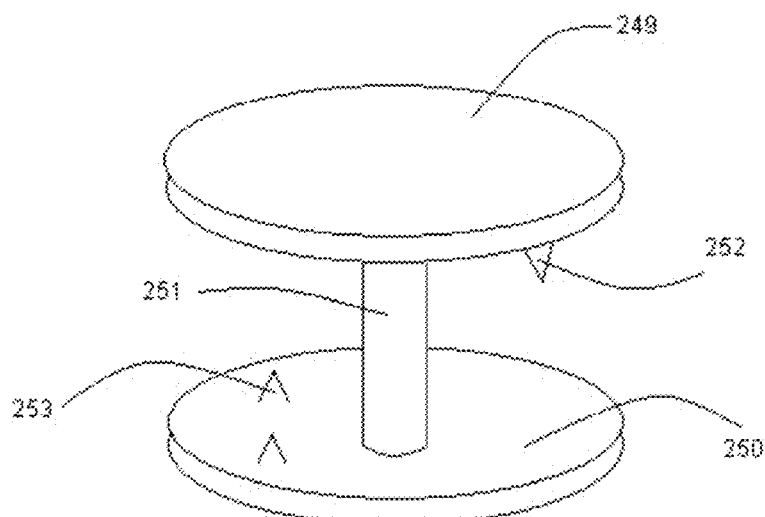
FIGS. 93 and 94 illustrate an exemplary cranial fixation device in accordance with an embodiment of the present invention.
Figure 94:
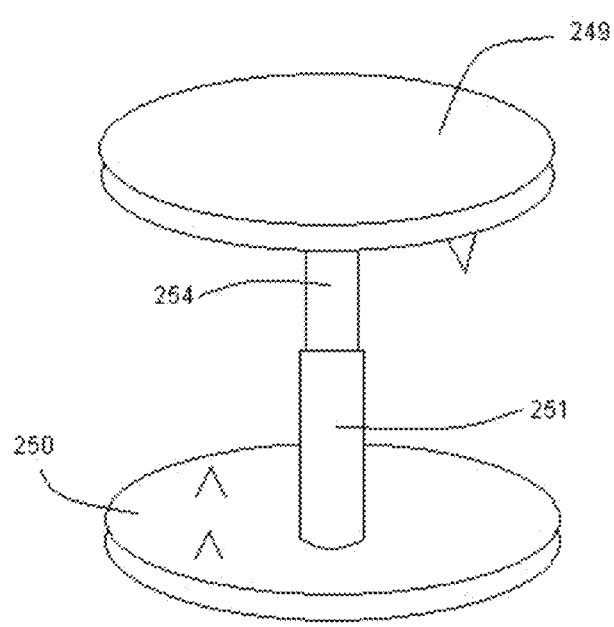
Figure 95:
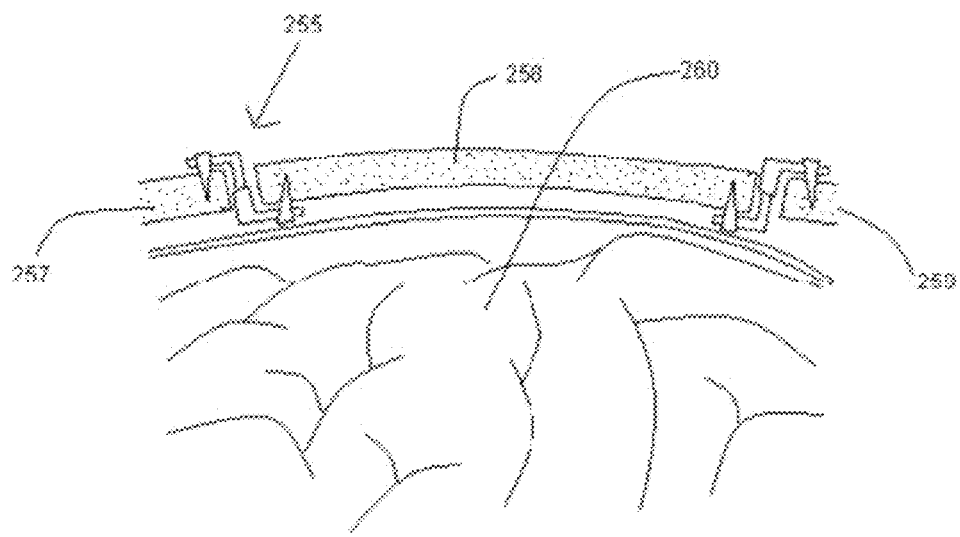
FIGS. 95 and 96 are cross sectional side views of exemplary cranial fixation devices attached to a skull and a bone flap for a decompressive craniotomy, in accordance with an embodiment of the present invention.
Figure 96:
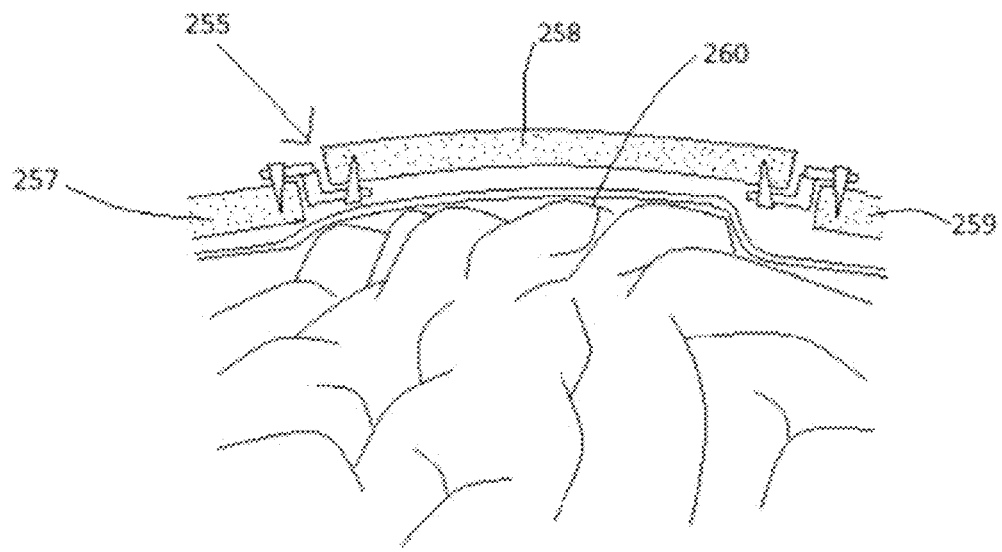

In another embodiment of the decompressive craniotomy device as shown in FIGS. 93 and 94, the device comprises of a head 249 and a head 250 connected with a telescopic portion 251. The head 249 resting on the outer surface of the bone flap and skull also comprising of spikes 252 on the side of the head secured to the bone flap and the opposing side of the head 249 rests on the skull. The head 250 rests on the inner surface of the skull and bone flap and the telescopic portion 251 is positioned in the skull defect. The side of the head 250 towards the skull comprises of spikes 253. The telescopic portion 251 also comprises of extension 254 that allows outward movement of the head 249 as shown in FIG. 94. The two heads or telescopic extensions are also connected with an elastomeric cord or spring that provides constrained inward and outward movement of the heads relative to each other. The method for cranial bone flap fixation with the device in FIGS. 93 and 94 is illustrated in FIGS. 95 and 96. FIG. 95 illustrates the cranial fixation devices 255 and 256 in place attached to the outer and inner surface of the bone flap 258 and the skull 257 and 259 respectively. The brain 260 is shown in its normal position. Typically two or more of the cranial fixation devices would be placed to fixate the bone flap 258 to the skull 257 and 259 with the cranial fixation device telescopes in a retracted position approximating the bone flap to the skull. As shown in FIG. 96, with the development of brain swelling or an increase in intracranial pressure from a hemorrhage, the swollen brain 260 pushes against the bone flap 258. The pressure on the bone flap places the cranial fixation device 255 and 266 telescopes in an extended position thereby allowing the bone flap to move outwards and accommodate the brain swelling. With subsidence of the brain swelling the springs or elastomeric cords retract the heads towards each other and approximate the bone flap to the skull.

Although several telescopic extension engaging mechanisms are described in the various embodiments, it is obvious that any variations made to the embodiments by those skilled in the art maintain the broad incentive concepts described herein.

The decompressive craniotomy device as shown in FIGS. 97 and 98 comprise of a head 261 with an extension 263 and a head 262 with an extension 264. The extensions 263 and 264 are telescopic and allow for distraction or compression of the heads relative to each other. FIG. 97 shows the telescopic extensions 263 and 264 in a distracted position and FIG. 98 shows the extensions in a compressed position whereby the extension 263 is contained within the extension 264. FIGS. 99 and 100 illustrate the cross sectional longitudinal view of the device in FIGS. 97 and 98. FIG. 99 shows the two heads 261 and 262 along with their telescopic extensions 263 and 264 in a distracted position. The spring 265 is positioned inside the hollow extensions 263 and 264 and connects the two heads 261 and 262. The spring could also be positioned outside the telescopic connectors, which would also provide for a smaller diameter or width of the telescopic extensions. FIG. 100 shows the two heads 261 and 262 along with their telescopic extensions 263 and 264 in a compressed position maintained by the spring 265.

Figure 101:
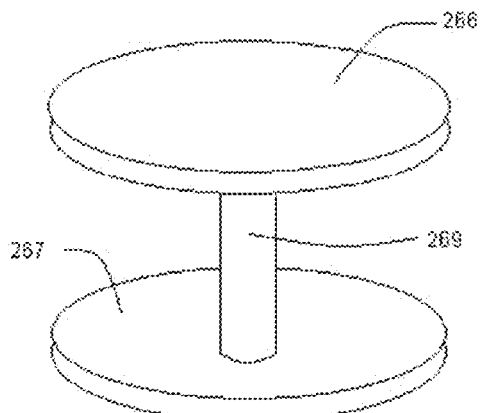
FIGS. 101 through 104 illustrate an exemplary cranial fixation device in accordance with an embodiment of the present invention.
Figure 102:
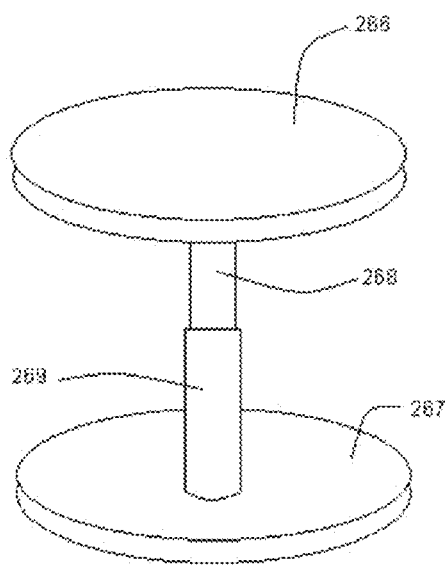
Figure 103:
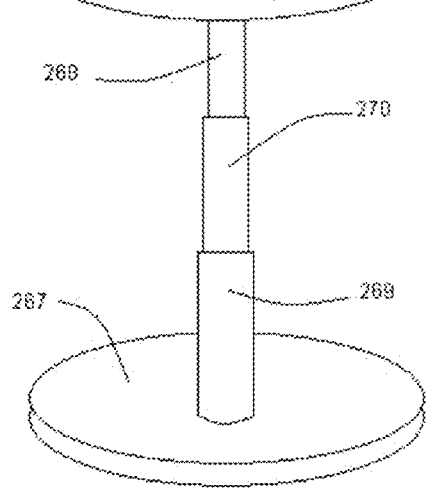

In another embodiment of the decompressive craniotomy device as shown in FIGS. 101-103, the head 266 comprises an extension 268 and the head 267 comprises an extension 269. The telescopic extensions from each head can also be connected with another intermediary telescopic component to allow further distraction of the heads if needed and retract into each other. The extensions 268 and 269 are telescopic and connected by an intermediate telescopic extension 270. The heads 266 and 267 are also connected by a spring or an elastic band or cord (not shown). FIG. 101 illustrates the completely retracted position of the telescopic extensions whereby the extensions 268 and 270 have retracted inside the extension 269. FIG. 102 illustrates the partially extended position of the telescopic extensions whereby the intermediate extension 270 has retracted into the extension 269. FIG. 103 illustrates the completely extended position of the telescopic extensions which allows the heads to move outwards in response to an elevated ICP.

Figure 104:
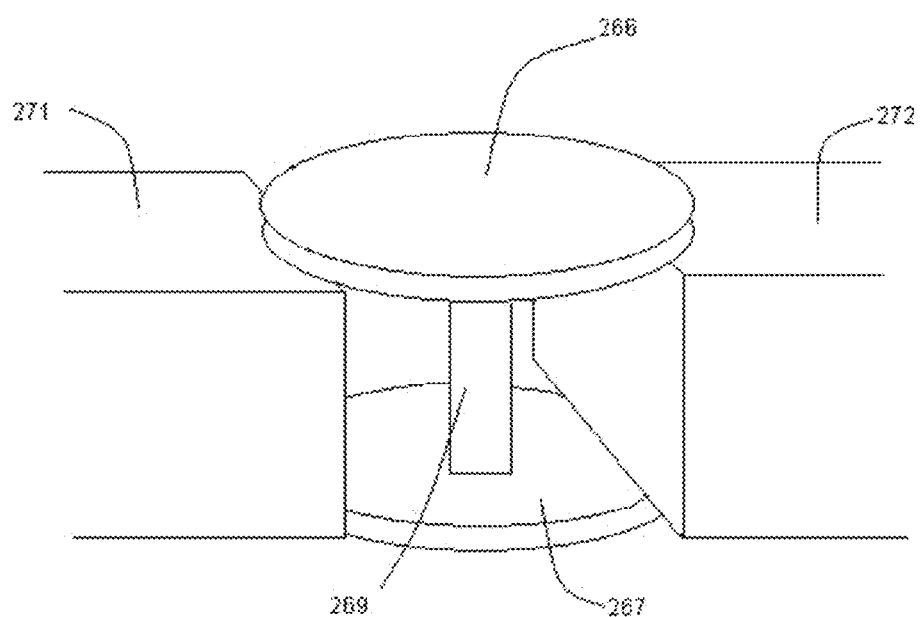

FIG. 104 illustrates the decompressive craniotomy device implanted on the skull in a retracted position. The head 266 is positioned on the outer surface of the skull 271 and bone flap 272. The head 267 is positioned on the inner surface of the skull 271 and bone flap 272. The spring inside the telescopic extension 269 allows the two heads to compress against the skull 271 and bone flap 272 thereby approximating them. The cranial fixation device heads are maintained in a distracted position manually and when the manual distraction is released after implantation to the skull the spring compresses the two heads together against the bone flap and skull. An elastomeric band or cord can also be used instead of a spring.

Figure 108:
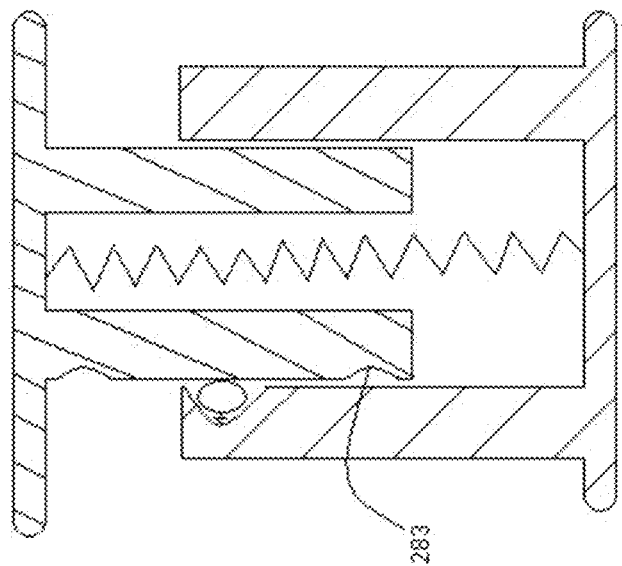
FIGS. 107 and 108 illustrate an exemplary cranial fixation device in accordance with an embodiment of the present invention.
Figure 107:
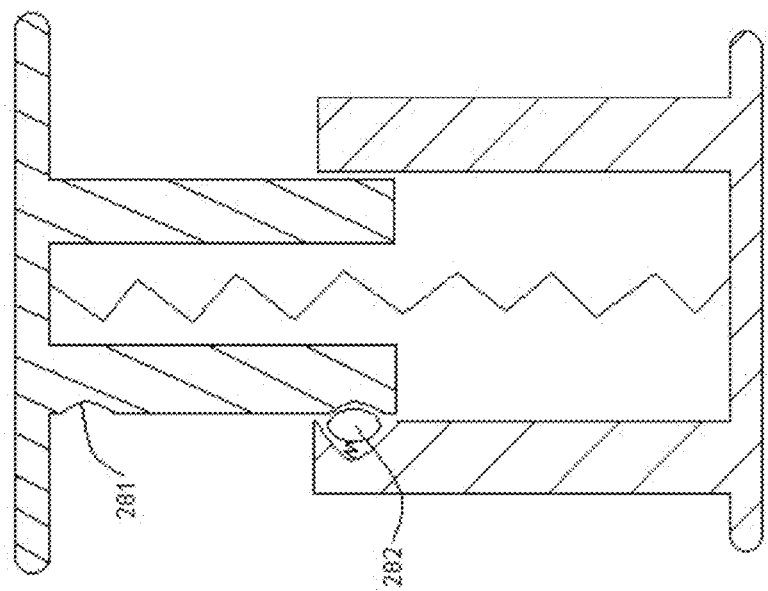
Figure 110:
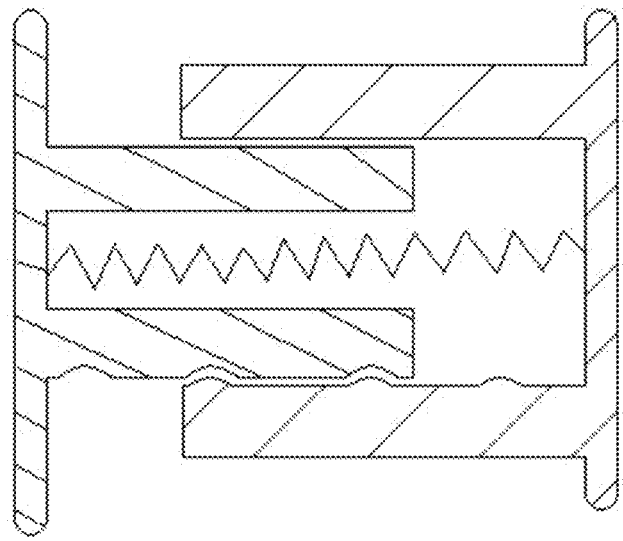
FIGS. 109 and 110 illustrate an exemplary cranial fixation device in accordance with an embodiment of the present invention.
Figure 109:
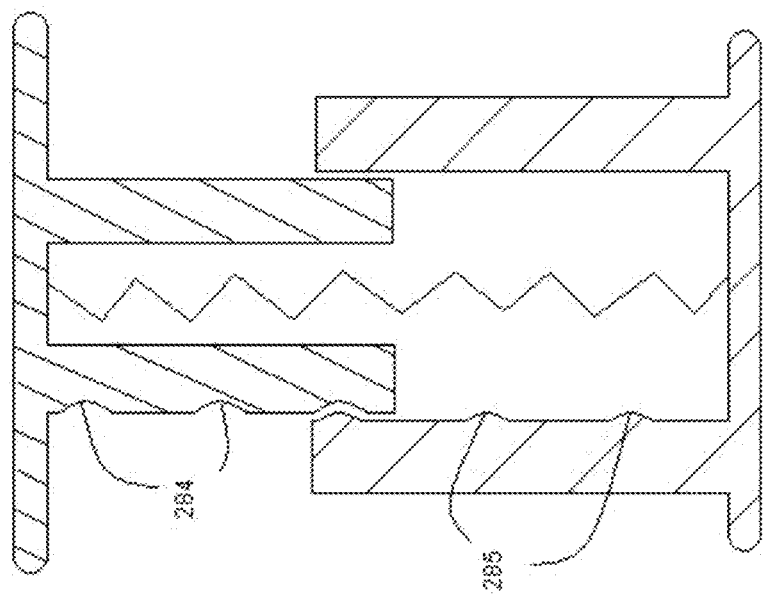
Figure 113:
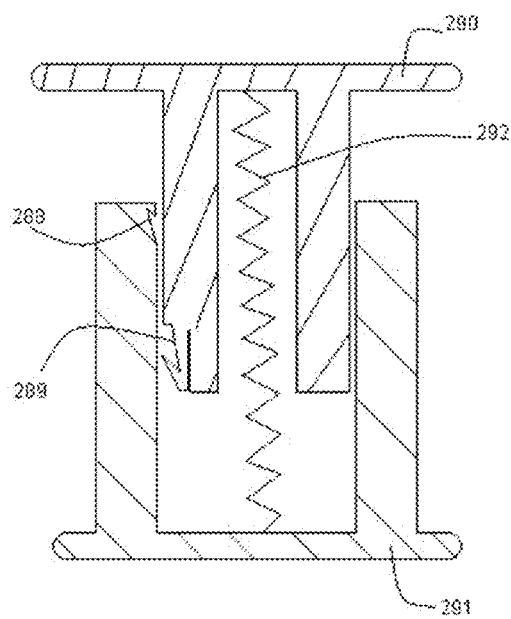
FIGS. 113 and 114 illustrate an exemplary cranial fixation device in accordance with an embodiment of the present invention.
Figure 114:
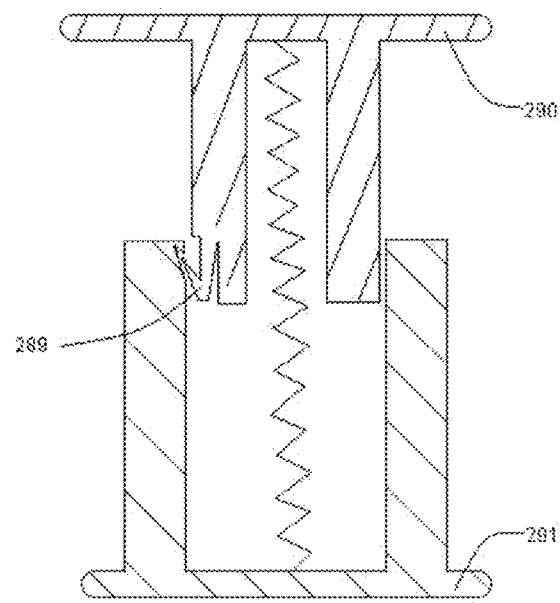

The heads can be maintained in a distracted position by a locking mechanism until ready for implantation. The locking mechanisms also prevent the telescopic extensions from pulling out from each other completely in an extended position. Several locking mechanisms are illustrated in the following embodiments. In one embodiment of the locking mechanism as shown in FIGS. 105 and 106, the telescopic extension 275 of head 273 comprises a socket 280. The telescopic extension 276 of head 274 comprises a collapsible ball 279. The collapsible ball and socket locking mechanism 277 maintains the two heads and their telescopic extensions along with the spring 278 in a distracted position as shown in FIG. 105. The locking mechanism can be released either by rotating the heads relative to one another or slightly distracting or compressing the heads, thereby placing the device in a retracted position facilitated by the spring 278 as shown in FIG. 106. In another embodiment of the decompressive craniotomy device as shown in FIGS. 107 and 108, the locking mechanisms engage during a completely distracted and retracted position. The locking mechanisms comprise of collapsible ball 282 with sockets 281 and 283. In a distracted position the ball 282 engages with the socket 283 as seen in FIG. 107 and in a retracted position the ball 282 engages with the socket 281. In another embodiment of the locking mechanism as illustrated in FIGS. 109 and 110, the ridges 285 engage with the grooves 284. In another embodiment, the locking mechanism illustrated in FIGS. 111 and 112 comprises of ratchets 286 and 287. In yet another embodiment, the locking mechanism as shown in FIGS. 113 and 114 comprises of a collapsible ratchet tooth 289 and corresponding recess 288. The two heads and telescopic extensions are maintained in a distracted position when the ratchet tooth 289 and recess 288 are engaged as shown in FIG. 114. The ratchet tooth 289 collapses and disengages from the recess 288 when the two heads 290 and 291 are pulled together by the spring 292 with normalization of the ICP as shown in FIG. 113.

Although several locking mechanisms are described in the various embodiments, it is obvious that any variations made to the embodiments by those skilled in the art maintain the broad incentive concepts described herein.

Figure 115:
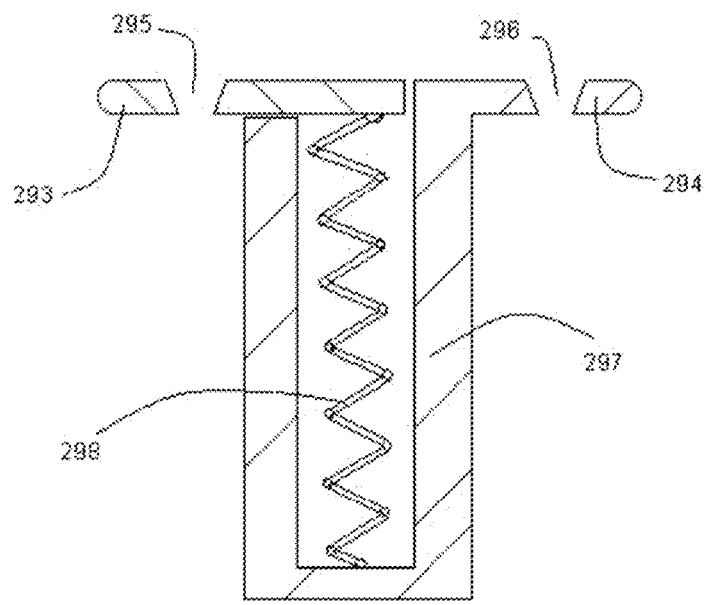
FIGS. 115 and 116 illustrate an exemplary cranial fixation device in accordance with an embodiment of the present invention.
Figure 116:
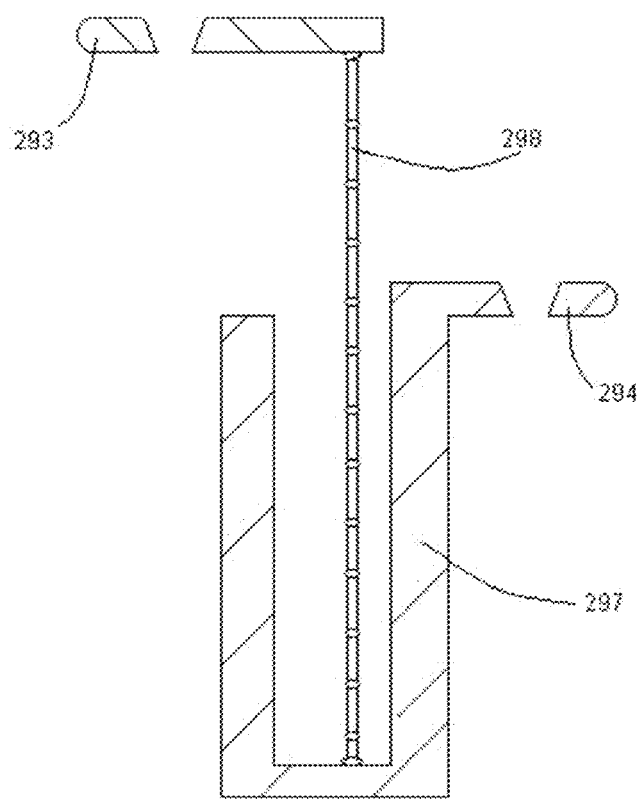
Figure 119:
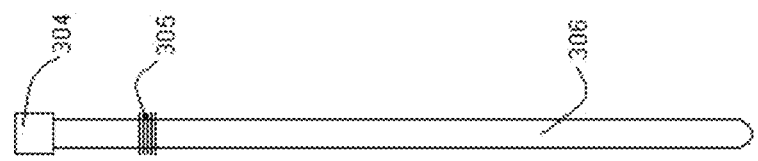
FIG. 119 is another schematic side view of the distracter in FIG. 118
Figure 118:
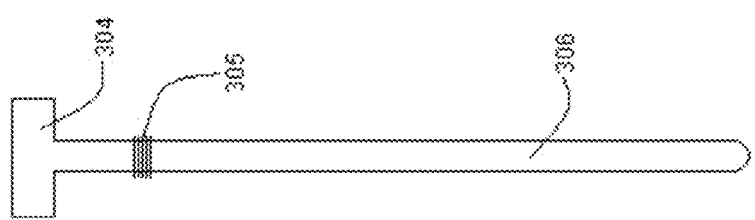
FIG. 118 is a schematic side view of the distracter for the cranial fixation device in FIG. 117.
Figure 117:
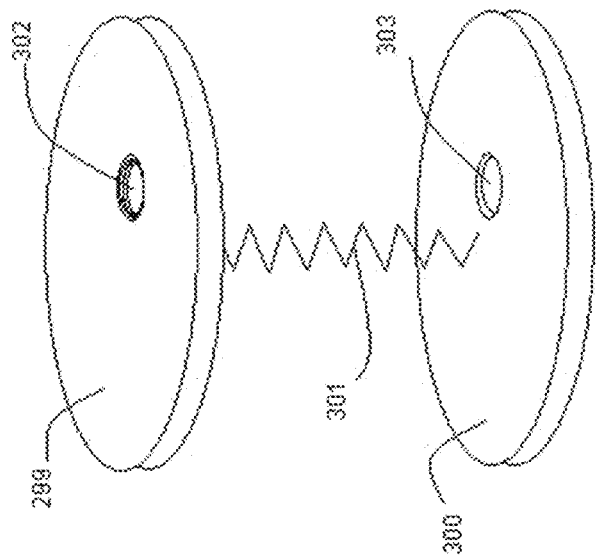
FIG. 117 is a schematic view of another embodiment of the cranial fixation device.

In another embodiment of the decompressive craniotomy device as shown in FIGS. 115 and 116, the head 294 comprises of an extension 297 and the head 293 is connected to the extension 297 with several cross-linked connectors 298. The head 293 also comprises of hole 293 for placement of a screw to fixate the bone flap. The head 294 comprises hole 296 for placement of a screw to the skull. With a normal ICP the heads 293 and 294 are positioned adjacent to each other as shown in FIG. 115. With an increase in ICP the head 295 attached to the bone flap is pushed outwards as shown in FIG. 116. The cross-links provide a constrained outward movement of the head 293 relative to the head 294.

In another embodiment of the decompressive craniotomy device as shown in FIGS. 117-121, the first head 299 comprises of a threaded hole 302 and the second head 300 contains a recess 303. The two heads 299 and 300 are connected by a spring 301. The device also comprises of a removable distracter shown in FIGS. 118 and 119 with a head 304, a shaft 306 with threads 305. As shown in FIG. 120 when the distracter is placed through the device with the shaft threads 305 engaged with the head hole threads 302 and the shaft 306 tip resting against the head recess 303, the two heads are in a distracted position ready for implantation onto the skull. As shown in FIG. 121, once the distracter is removed by manual rotation relative to the head 299, the threads 305 on the shaft disengage with the threads 302 in the head 299 and allow for compression between the two heads 299 and 300 by the spring 301.

Figure 123:
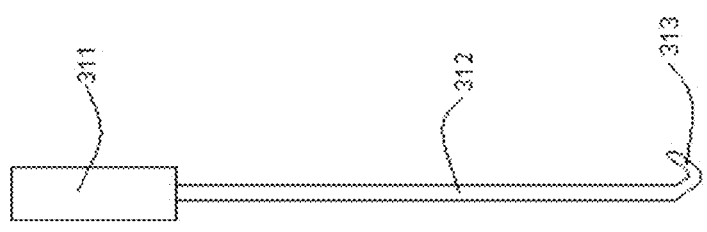
FIG. 123 is schematic view of the distracter for the cranial fixation device in FIG. 122.
Figure 122:
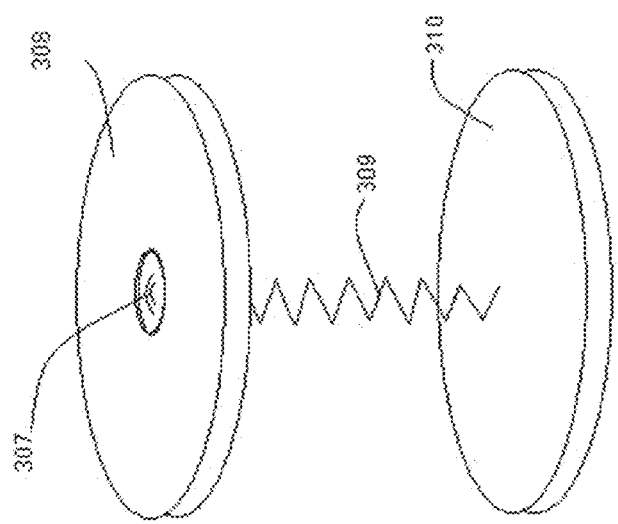
FIG. 122 is a schematic view of another embodiment of the cranial fixation device.
Figure 126:
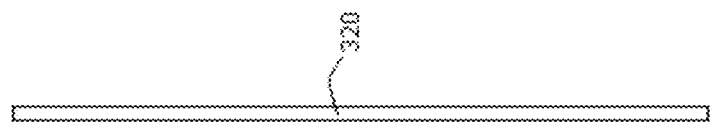
FIG. 126 is another schematic side view of the distracter in FIG. 125.
Figure 125:
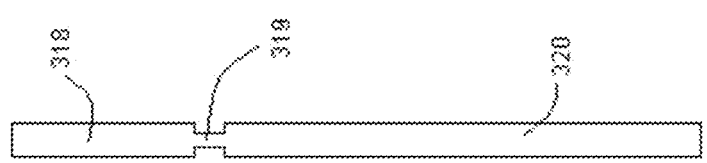
FIG. 125 is a schematic side view of the distracter for the cranial fixation device in FIG. 124.
Figure 124:
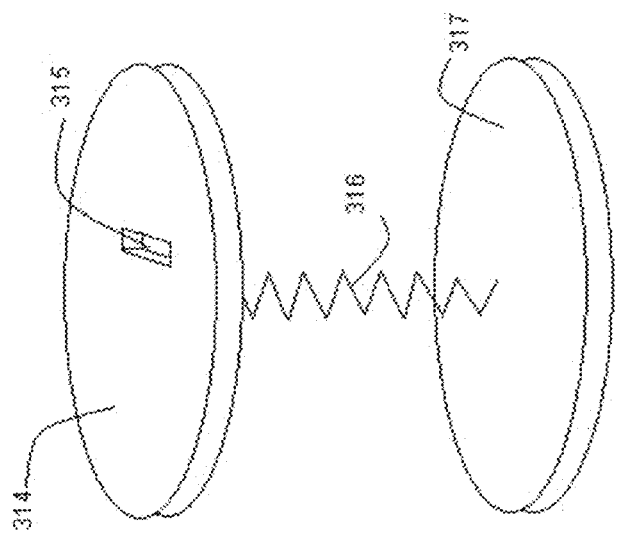
FIG. 124 is a schematic view of another embodiment of the cranial fixation device.

In another embodiment of the decompressive craniotomy device as shown in FIGS. 122 and 123, the first head 308 is connected to the second head 310 by a spring 309. The first head also comprises of a ridge 307 that can engage a hook instrument. The hook instrument as shown in FIG. 123 contains a head 311, a shaft 312, and a hook 313. The hook 313 engages with the ridge 307 and allows distraction of the heads 308 and 310 relative to each other prior to implantation to the skull.

Figure 127:
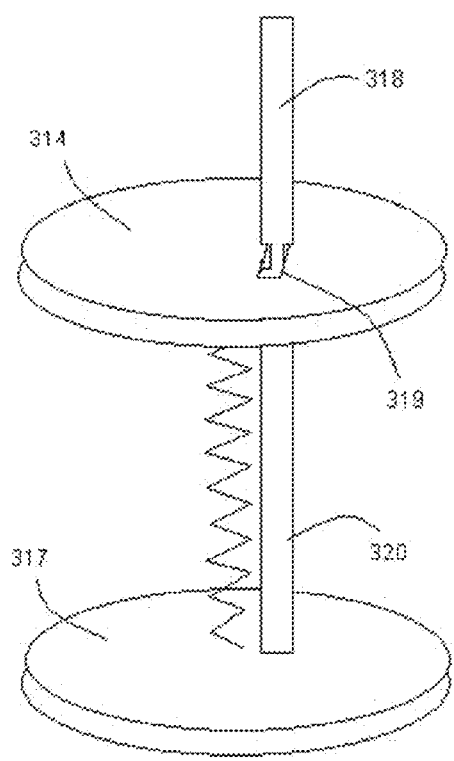
FIG. 127 is a schematic view of the cranial fixation device in FIG. 124 in an extended state with the distracter in FIG. 125 in place.
Figure 128:
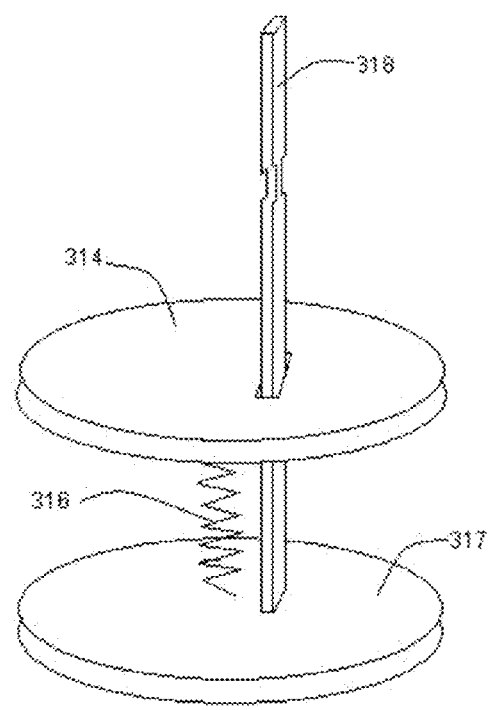
FIG. 128 is a schematic view of the cranial fixation device in FIG. 124 in a retracted state with the removable distracter in FIG. 125 in place.
Figure 131:
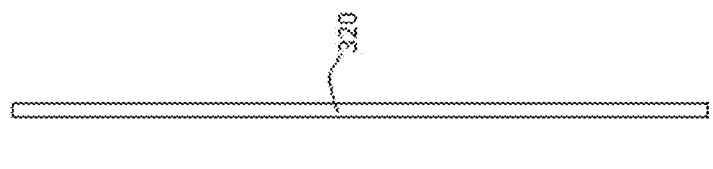
FIG. 131 is another schematic side view of the distracter in FIG. 129.
Figure 130:
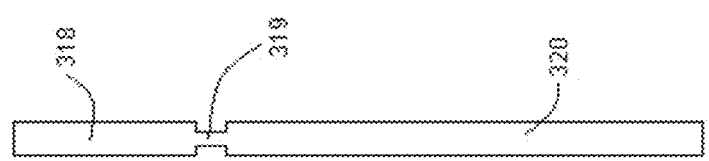
FIG. 130 is schematic view of the distracter for the cranial fixation device in FIG. 129.
Figure 129:
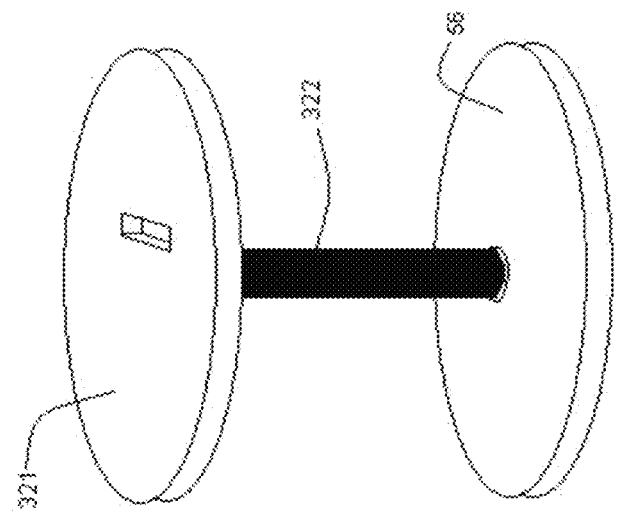
FIG. 129 is a schematic view of another embodiment of the cranial fixation device.
Figure 132:
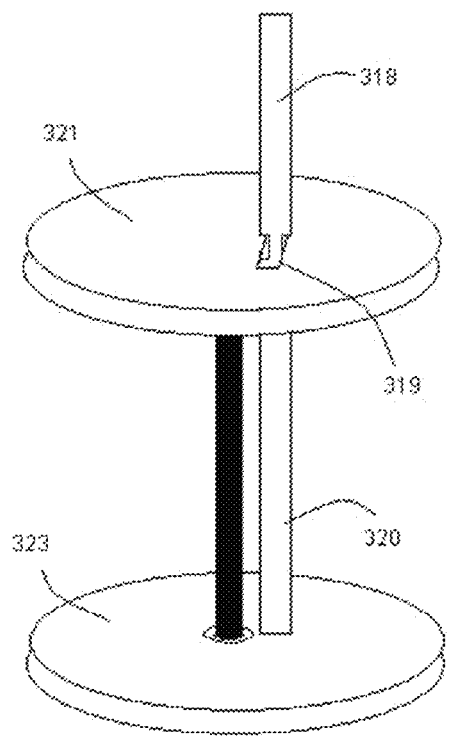
FIG. 132 is a schematic view of the cranial fixation device in FIG. 129 in an extended state with the distracter in FIG. 130 in place.
Figure 133:
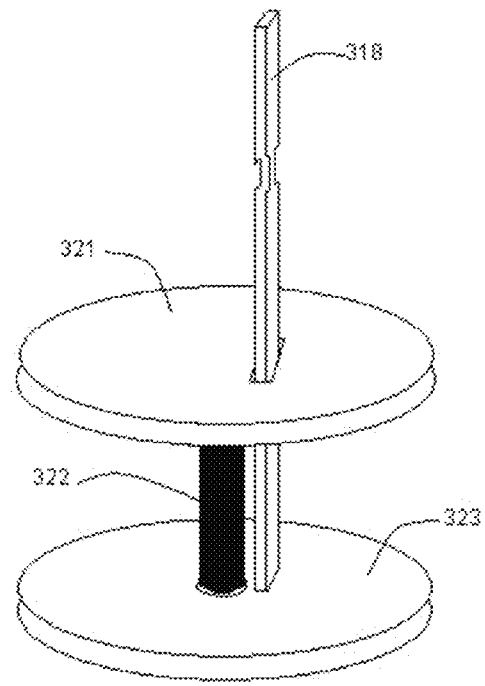
FIG. 133 is a schematic view of the cranial fixation device in FIG. 129 in a retracted state with the removable distracter in FIG. 130 in place.

In another embodiment of the decompressive device as shown in FIGS. 124-128, the first head 314 comprises of a rectangular opening 315. The head 314 is connected to the second head 317 by a spring 316. The spring maintains the two heads in a compressed position. The distracter shown in FIGS. 125 and 126 comprises of a head 318, shaft 319, and a narrow rectangular segment 319. The rectangular opening 315 in the first head 314 is configured to allow placement of the distracter and once the narrow portion 319 of the distracter is positioned in the opening 315, rotation of the distracter by 90 degrees engages the first head. As shown in FIG. 127, the two heads 314 and 317 are maintained in a distracted position by the distracter 318 placed through the head opening 315. The rectangular narrowing 319 in the shaft rests against the inner surface of the first head 314 with the shaft tip 320 resting on the inner surface of the second head 317. As illustrated in FIG. 128, the two heads 314 and 317 are allowed to compress by the spring 316 once the distracter 318 is rotated 90 degrees allowing for disengagement of the distracted position of the two heads and removal of the distracter. In another embodiment of the device above as shown in FIGS. 129-133, the heads 321 and 323 are connected with an elastomeric cord 322 instead of a spring. In another embodiment of the distracter as shown in FIGS. 134-136, the distracter comprises of a head 324, shaft 326, and a wider rectangular portion 325. The rectangular opening 315 in the first head 314 is configured to allow placement of the distracter and once the wider portion 325 is passed through the opening, the distracter shaft is rotated 90 degrees allowing for the wider portion 325 to rest against the inner surface of the head 314 and maintaining a distracted position of the two heads. Similarly the distracted position can be released by rotating the distracter to 90 degrees again whereby allowing the two heads to compress and secure the bone flap to the skull.

Figure 137:
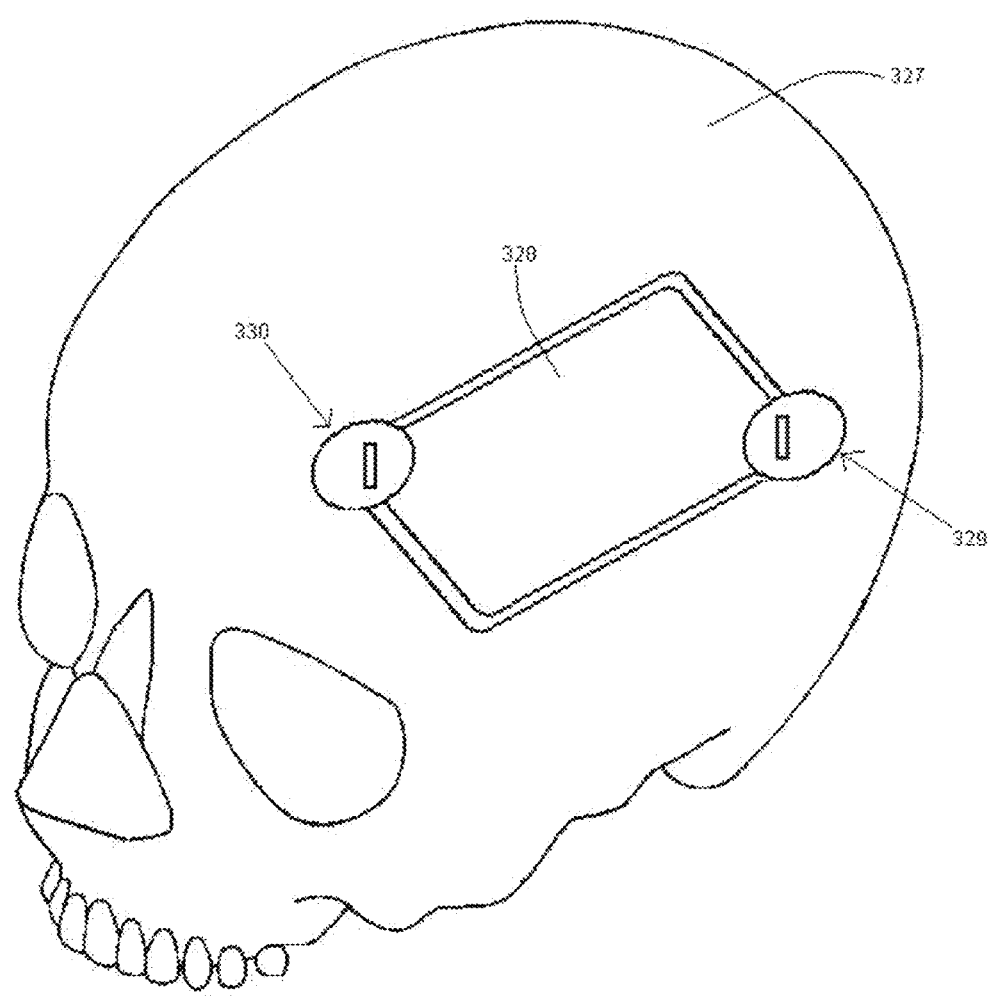

The implanted decompressive craniotomy devices are shown in FIGS. 137 and 138. Following the craniotomy, the bone flap 328 is replaced attaching to the skull 327 with the devices 329 and 330 placed through the burr hole defects. The device heads cover the burr hole openings and compress the bone flap against the skull as shown in FIG. 137. With an increase in ICP, the swollen brain pushes against the bone flap which moves the device head on the outer surface of the bone flap outwards as shown in FIG. 138. The outwards movement of the bone flap provided by the device accommodates the increase in ICP and once the brain swelling subsides, the spring or elastomeric cord retracts the device heads towards each other and approximates the bone flap to the skull.

Figure 140:
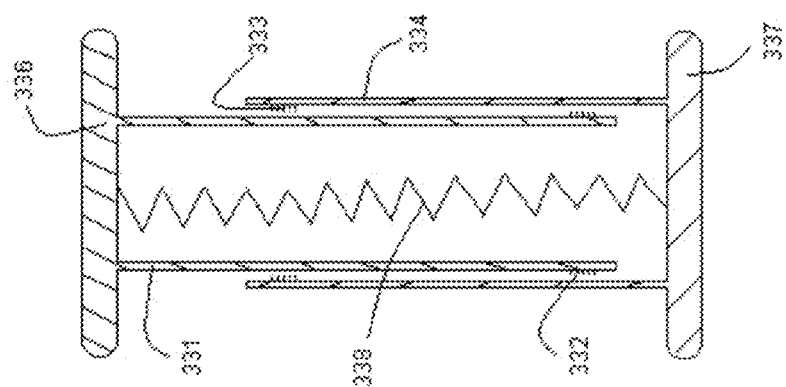
FIGS. 139 and 140 illustrate fixation device according to certain embodiments of the invention.
Figure 139:
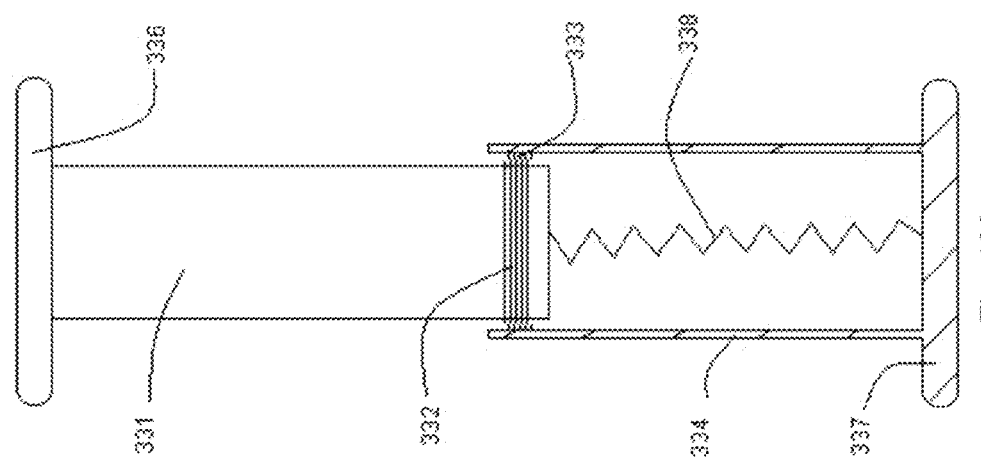

In another embodiment, the decompressive craniotomy device illustrated in FIGS. 139-142 comprises of a first head 336 with a telescopic extension 331 and a second head 337 with a telescopic extension 334. The telescopic extensions are hollow cylinders and contain a spring 338 connecting the two heads 336 and 337. The spring can reside inside or outside the telescopic extensions. The outer portion of the first telescopic portion distal end 332 and the inner portion of the second telescopic distal end 333 are threaded. As shown in FIG. 139 the cranial fixation is in an extended position with the telescopic extension threads 332 and 333 engaged. Once the device is placed through the burr hole opening between the skull and the bone flap, the head 336 is rotated relative to the head 337 until the threads disengage thereby allowing the spring to compress the heads together against the skull and bone flap. The compressed state of the heads is illustrated in FIG. 140. The head 336 with the telescopic extension 331 slides inside the telescopic extension 334 of the head 337, facilitated by the spring 338. The partial threads 333 and 332 are in the disengaged position. In another embodiment as shown in FIGS. 141 and 142, the inner portion of the second telescopic extension 334 comprises of partial threads at the proximal end 335 and distal end 333. Once the heads are in a contracted position, they can also be locked by the proximal threads 335 on extension 334 engaging with the distal threads 332 on extension 331.

In another embodiment the decompressive craniotomy device illustrated in FIGS. 143-145 comprises of a head 339 with a cylindrical extension 341 slidably coupled to a hollow cylindrical extension 342 with a head 340. The two heads are connected by a spring. As shown in FIG. 143 the two heads are maintained in a distracted position by a locking mechanism comprised of a ridge 344 at the distal end of the telescopic extension 341 and a longitudinal opening 343 in the telescopic extension 342. The longitudinal opening is L-shaped and when the ridge is engaged in the short arm 345 of the L-shape, the heads are in a distracted position. As shown in FIG. 144 rotating the heads 339 and 340 relative to each other places the ridge 344 in the long arm of the L-shaped opening 343, thereby, allowing the heads to compress and the telescopic extensions to slide into each other. FIG. 145 is a magnified view of the locking mechanism along the line A with the ridge 344 on the telescope 341 engaging the corresponding opening 345 in the telescope 342.

Figure 146A:
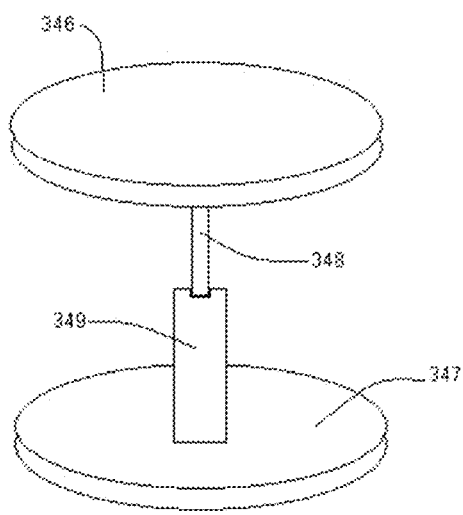
FIGS. 146A through 148 illustrate an exemplary cranial fixation device in accordance with an embodiment of the present invention.
Figure 146B:
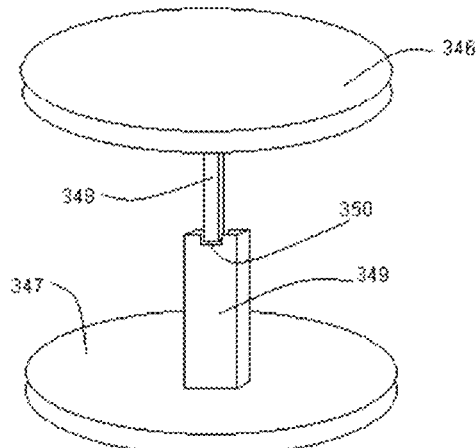
Figure 147:
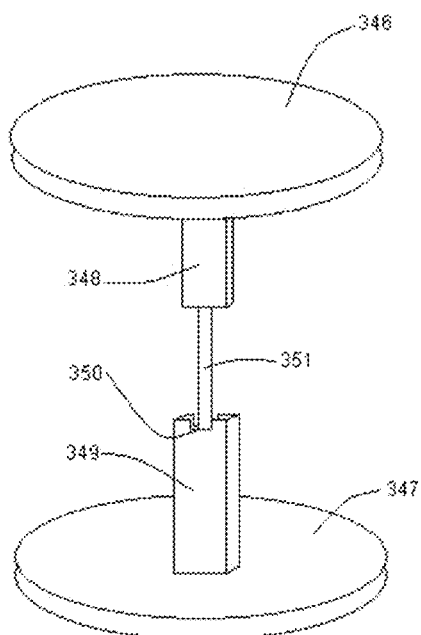
Figure 148:
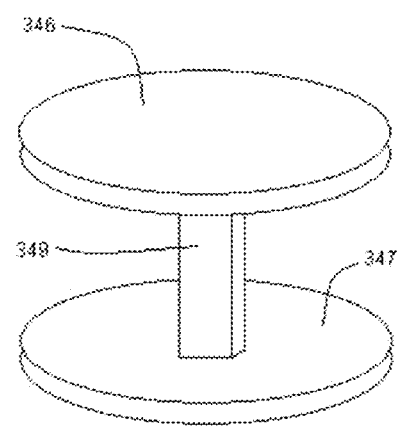

In another embodiment illustrated in FIGS. 146 and 147, the decompressive craniotomy device comprises of a head 346 with a rectangular telescopic extension 348 slidably coupled to a hollow rectangular telescopic extension 349 with a head 347. The telescopic extension 349 has a recess 350 at the distal end. As shown in FIG. 146 when the telescopic extension 348 is rotated 90 degrees in an extended state relative to the telescopic extension 349, the distal end of the telescopic extension 348 rests in recess 350 at the distal end of the telescopic extension 349. As shown in FIG. 147 rotation of the head 346 relative to head 347 another 90 degrees places the corresponding telescopic extensions parallel to each other. The elastomeric band 351 subsequently retracts the extension 348 into the extension 349 placing the heads closer towards each other as shown in FIG. 148. In an alternate embodiment a spring can be used instead of an elastic hand.

Figure 149:
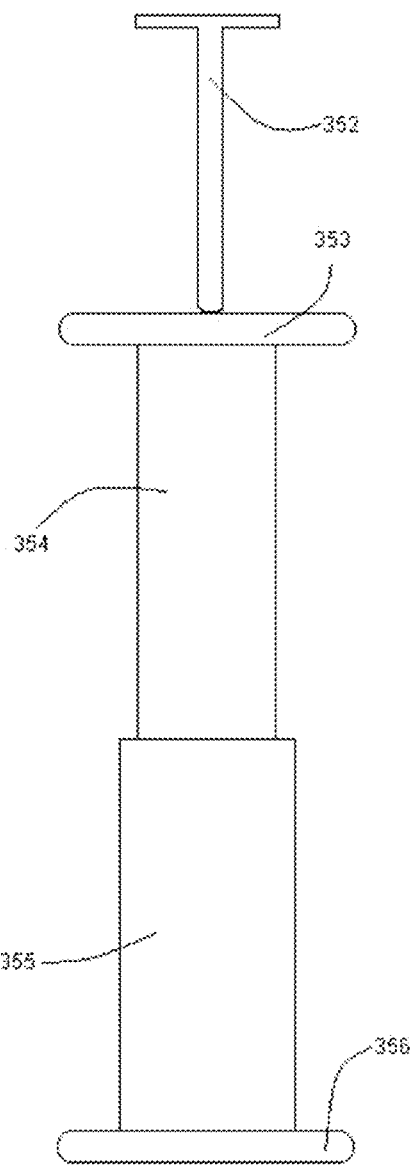
FIGS. 149 and 150 illustrate an exemplary cranial fixation device in accordance with an embodiment of the present invention.
Figure 150:
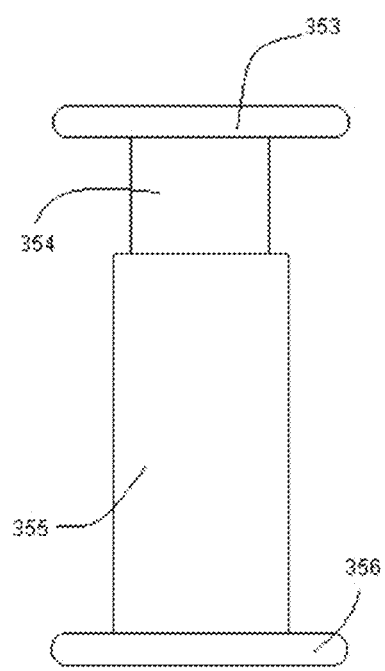

The telescopic engaging mechanism can be released either by rotating the heads relative to one another or slightly distracting the heads further. In any of the above described embodiments, the head placed on the outer skull surface can also contain an opening to accommodate a hook or similar instrument to maintain a distracted position. The hook can also be used to rotate or further distract the head in the embodiments that contain a locking mechanism. The head on the outer portion of the skull can also contain an extension as illustrated in FIG. 149. The head 353 positioned on the outer surface of the skull comprises of an extension 352 and a telescope 354. The head 356 positioned on the inner surface of the skull comprises of a telescope 355. The extension 352 is used to distract or rotate head 353 relative to the head 356. The extension 352 can be removed by manually snapping it off or with the use of a cutting instrument. FIG. 150 illustrates the cranial fixation device with the telescopic extensions 354 and 355 in a retracted position with the extension 352 removed from the head 353.

In other embodiments, the locking mechanisms described above can engage during a distracted position as well as a retracted position. While the spring connecting the two heads illustrated in the various embodiments above resides inside the telescopic component, it can be placed outside the telescopic portions. In other embodiments the telescopic extensions can be positioned inside the central hollow portion of the spring.

Figure 151:
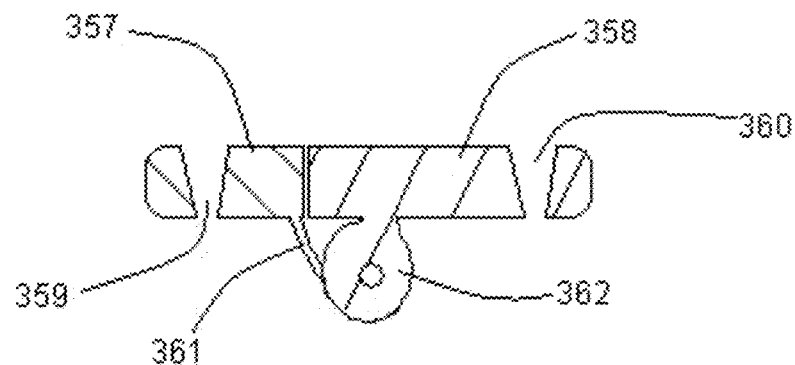
FIGS. 151 and 152 illustrate an exemplary cranial fixation device in accordance with an embodiment of the present invention.
Figure 152:
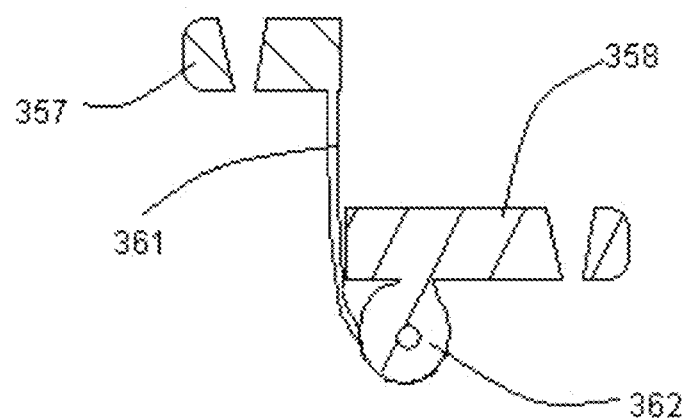

In another embodiment of the decompressive craniotomy device shown in FIGS. 151 and 152, the head 357 rests on the outer surface of the bone flap and the head 358 rests on the outer surface of the skull. The head 357 comprises a hole 359 for placement of a screw to secure the head to the bone flap. The head 358 comprises a hole 360 for placement of a screw to secure the head to the skull. The head 358 also comprises a capstan extension 362 which is positioned in the skull burr hole defect. The head 357 also comprises a spiral compression-distraction capstan connected to the head 357 with a wire or cable 361. The capstan can contain a spring which provides resistance when the head 357 moves outwards relative to the head 358 as seen in FIG. 152 and also retracts the heads towards each other once the ICP normalizes as seen in FIG. 151.

Figure 153:
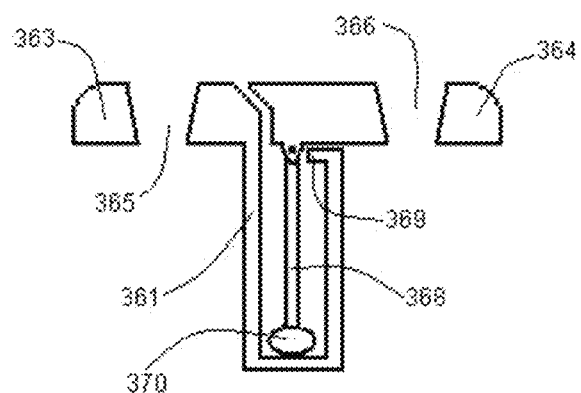
FIGS. 153 and 154 illustrate an exemplary cranial fixation device in accordance with an embodiment of the present invention.
Figure 154:
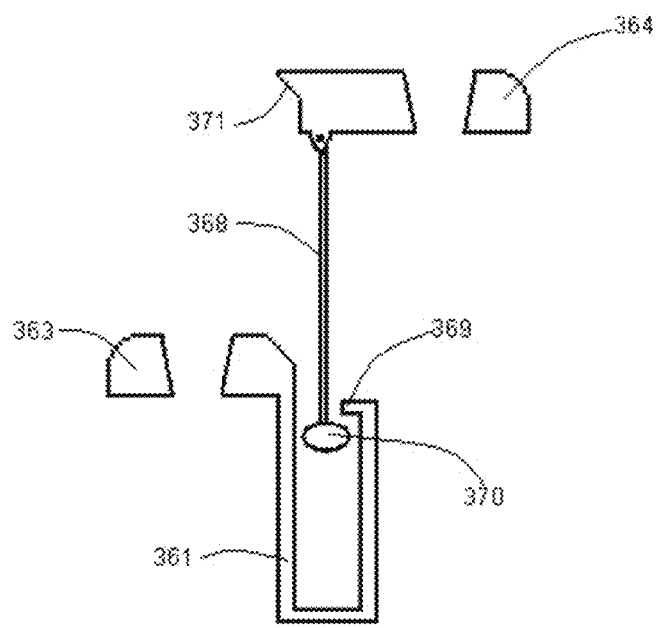

In another embodiment of the decompressive craniotomy device as shown in FIGS. 153 and 154, the first head 363 comprises a bone screw holes 365 for attachment to the skull and a hollow extension 361 that resides in the skull defect. The second head 364 comprises bone screw holes 366 for attachment to the bone flap and an elastomeric extension 368. The elastomeric extension is secured to the head 364 at one end and comprises of an enlarged solid portion 370 at the other end. The elastomeric extension 368 stretches when the head 364 moves outwards with an increase in ICP as shown in FIG. 154 and subsequently with normalization of ICP the elastic extension 368 retracts the head 364 back towards the head 363 as shown in FIG. 153. The medial edges of the heads can be sloped 371 to prevent the head 364 from moving inwards beyond the head 363.

Although the flexible component connecting the two heads described in most embodiments of the decompressive craniotomy device is a spring, it can also be an elastomeric band or cord. The elastomer can be made out of rubber, rubber derivative, silicone or any elastic biocompatible material. It could also be made out of a shape memory alloy like nitinol.

Figure 155:
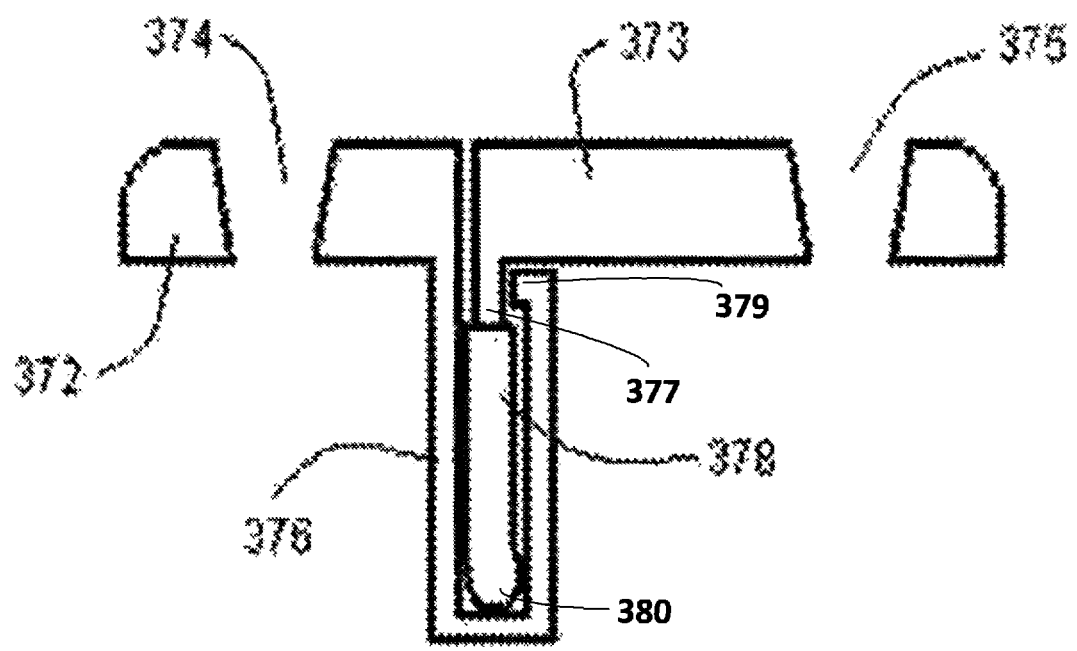
FIGS. 155 through 157 illustrate an exemplary cranial fixation device in accordance with an embodiment of the present invention.
Figure 156:
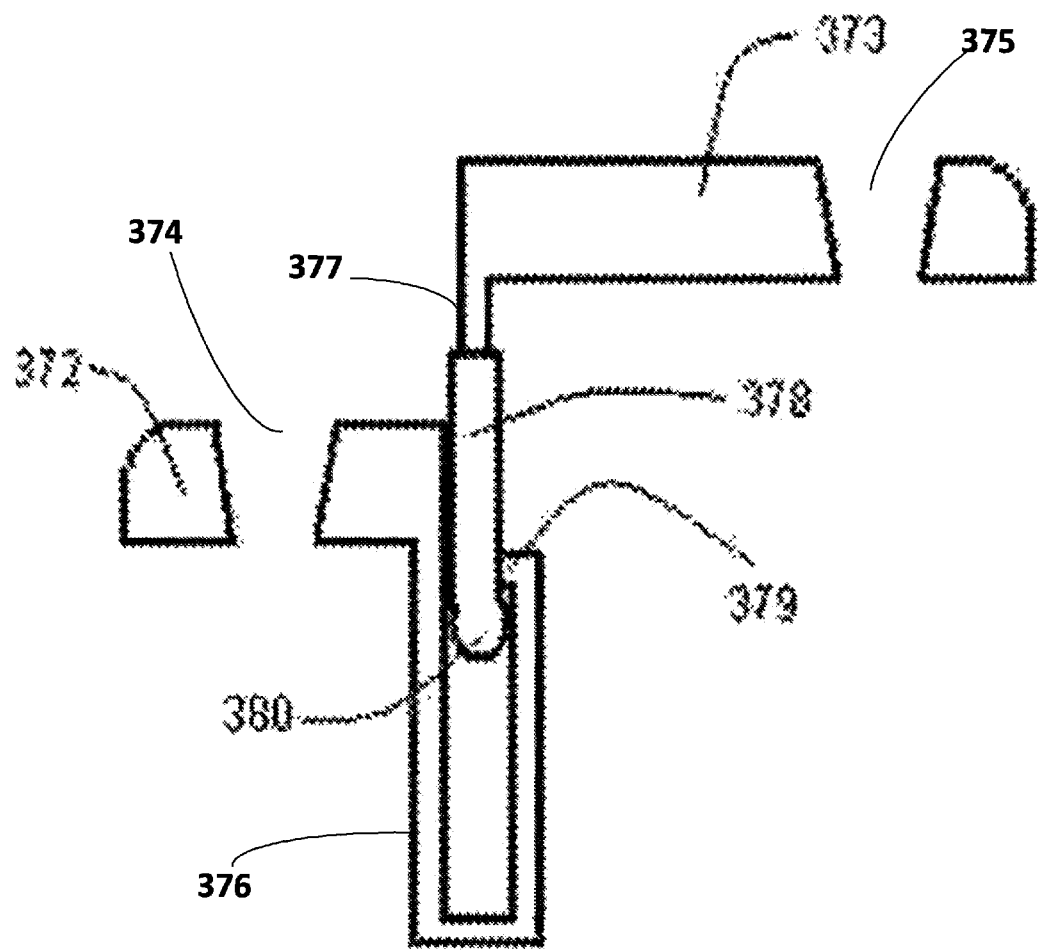
Figure 157:
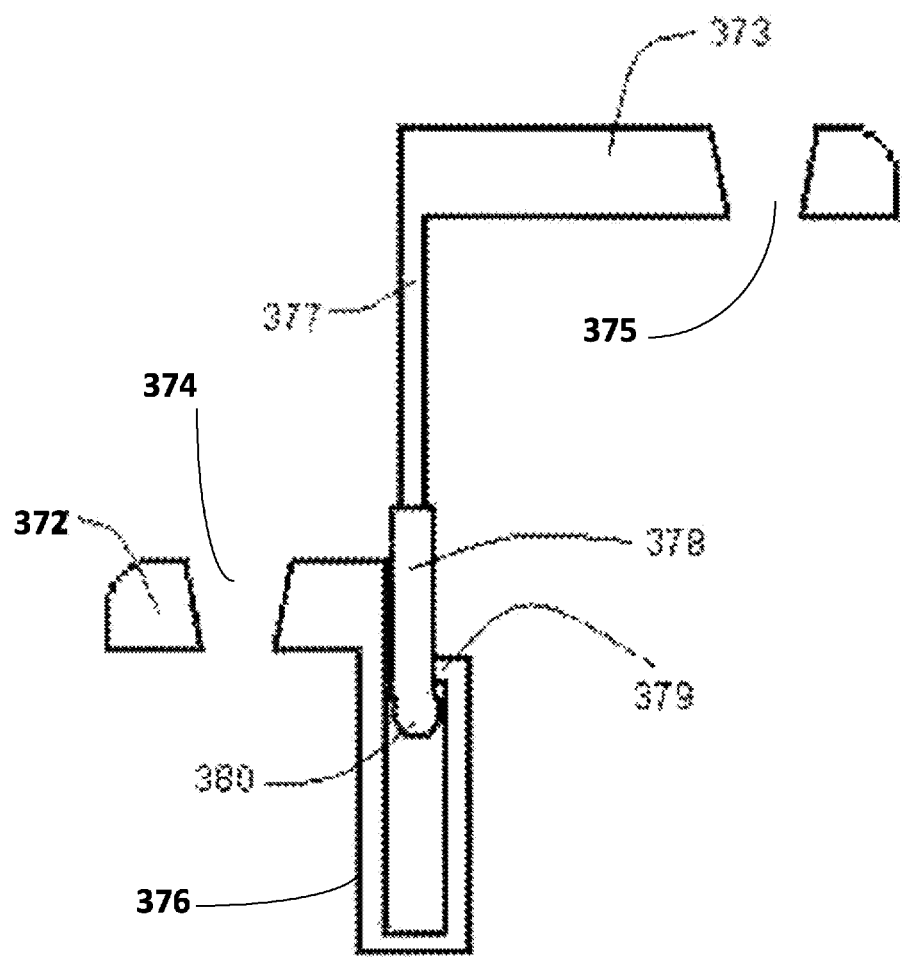

In another embodiment of the decompressive craniotomy device as illustrated in FIGS. 155 and 156, the head 372 comprises a housing extension 376 that is positioned in the skull defect and a bone screw hole 374 for attachment to the skull. The head 373 comprises telescopic extensions 377 and 378 as well as bone screw hole 375 for attachment to the bone flap. The telescopic extension 377 partly resides inside the telescopic extension 378 when the heads 372 and 373 are positioned together as shown in FIG. 155. The telescopic housing extension 376 comprises an inner extension 379 that engages with the enlarged telescopic extension end 380 in a completely extended position to prevent the extension 378 from completely pulling out of the housing extension 376 as shown in FIGS. 156 and 157.

In another embodiment of the decompressive craniotomy device as shown in FIGS. 158 and 159, the head 380 comprises a socket 385 positioned in the skull defect and a bone screw hole 382. The head 381 comprises a ball 384 and a bone screw hole 383. The ball 381 and socket 385 joint connection at the head ends allows the head 381 to move upwards relative to the head 380 as shown in FIG. 159 and also prevents the head 381 from moving inwards beyond the head 380 as shown in FIG. 158.

Figure 160:
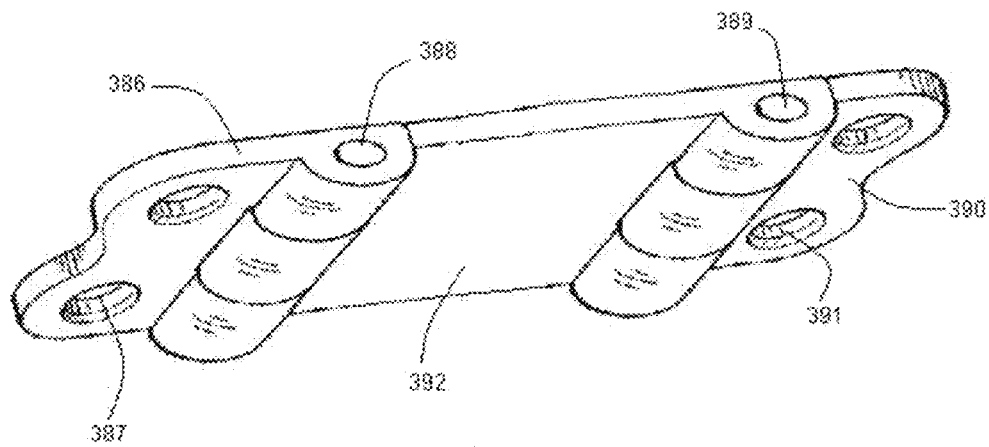
FIGS. 160 through 162 illustrate an exemplary cranial fixation device in accordance with an embodiment of the present invention.
Figure 161:
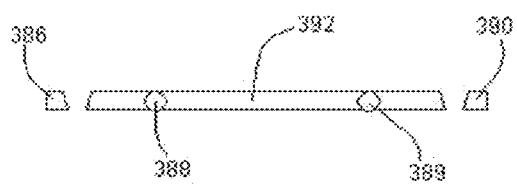
Figure 162:
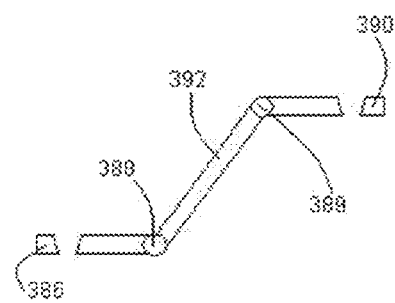
Figure 165:
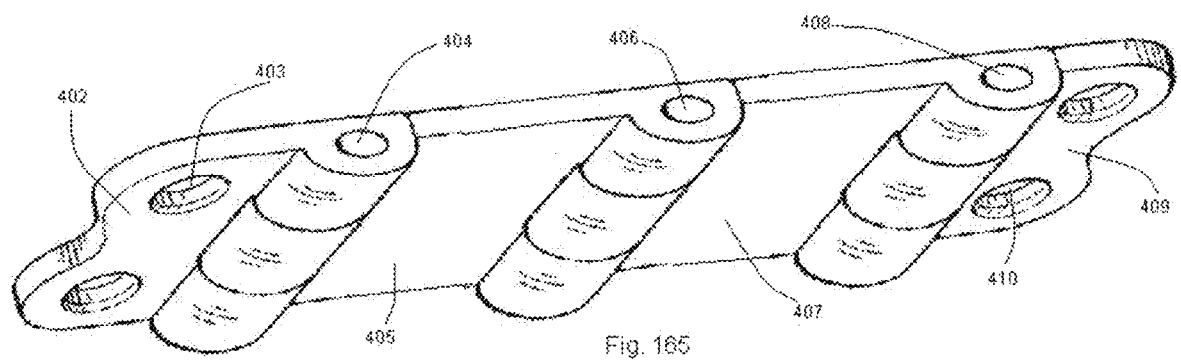
FIGS. 165 through 170 illustrate an exemplary cranial fixation device in accordance with an embodiment of the present invention.
Figure 166:
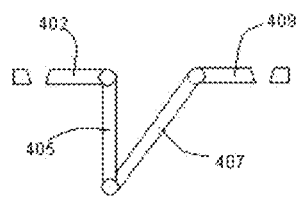
Figure 167:
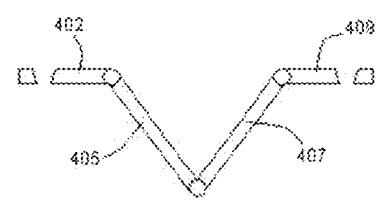
Figure 168:
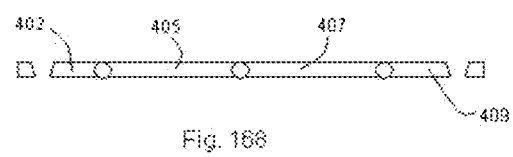
Figure 169:
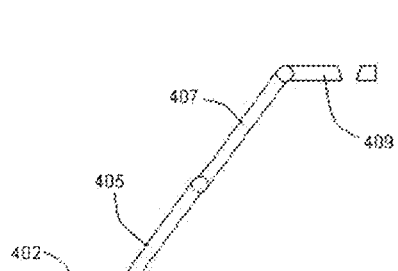
Figure 170:
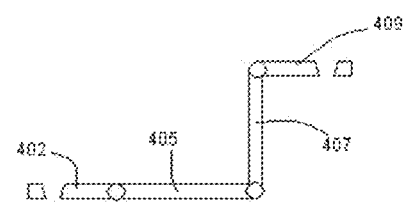
Figure 176:
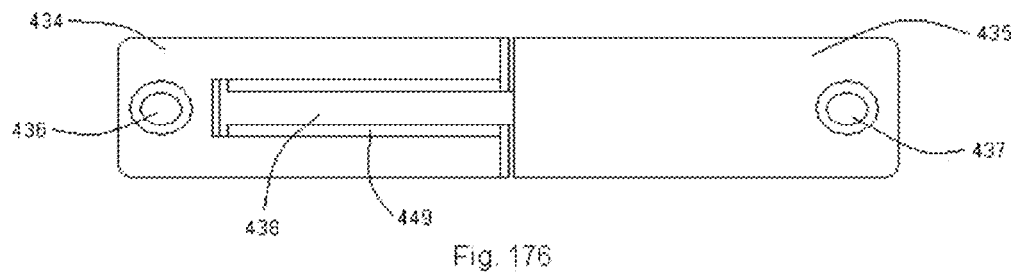
FIGS. 176 through 182 illustrate an exemplary cranial fixation device in accordance with an embodiment of the present invention.
Figure 177:
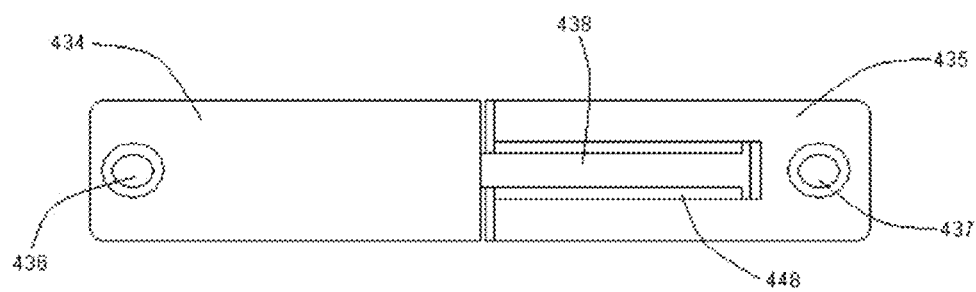
Figure 178:
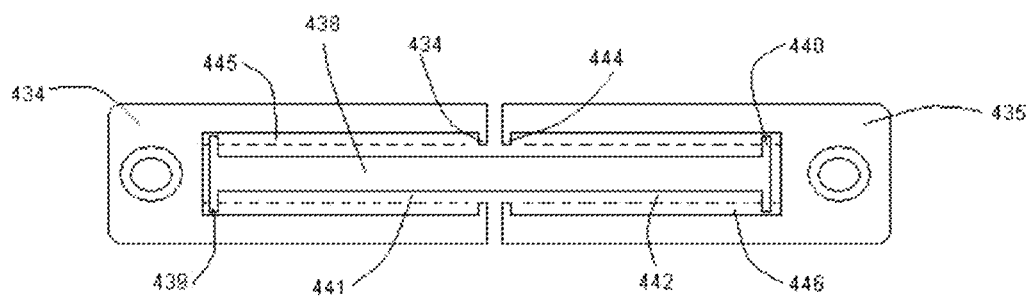

In another embodiment of the decompressive craniotomy device shown in FIGS. 160-162, the head 386 comprises bone screw holes 387 for attachment to the skull and a hinge 388. The head 390 comprises bone screw holes 391 for attachment to the bone flap and a hinge 389. The hinges 388 and 389 are connected by a plate 392 that covers the burr hole skull defect. FIGS. 160 and 161 illustrate the device with the heads 386 and 390 at the same position. FIG. 162 illustrates the head 390 positioned upwards relative to head 386.

In another embodiment of the decompressive craniotomy device as shown in FIGS. 163 and 164, the head 393 comprises bone screw holes 394 and a socket 396. The head 400 comprises bone screw holes 401 and a socket 399. The sockets 396 and 399 are connected with a connector 395 containing balls 397 and 398 at the ends. FIG. 163 shows the device with the heads 393 and 400 in the same position and FIG. 164 shows the head 400 positioned upwards relative to the head 393.

In another embodiment of the decompressive craniotomy device shown in FIGS. 165-170, the heads 402 and 409 are connected by two intermediate plates 405 and 407 with hinges 404, 406, and 408. The head 402 also comprises of holes 403 for placement of screws into the skull and the head 409 comprises of holes 410 for placement of screws into the bone flap. FIGS. 166-170 illustrate the various head and intermediate plate positions facilitated by the hinges.

In another embodiment of the decompressive craniotomy device shown in FIGS. 171 and 172, the heads 411 and 421 are connected by two intermediate connectors 415 and 418 with balls 414, 417, and 420 and their respective sockets 413, 416, and 419. FIG. 171 illustrates the heads 411 and 421 in the same position and FIG. 172 illustrates the head 421 moved upwards relative to head 411. The ball and socket joints allow upward movement of the head 421 relative to the head 411 but do not allow the head 421 to move below the head 411.

In another embodiment of the decompressive craniotomy device shown in FIGS. 173-1.75, the heads 423 and 432 are connected by two plates 427 and 429 with a ball & socket joints 426 & 425 and 430 & 431. The two intermediate plates 427 and 429 are connected to each other with a hinge 428. Various different positions of the head 432 relative to the head 423 are shown in FIGS. 173-175.

Figure 179:
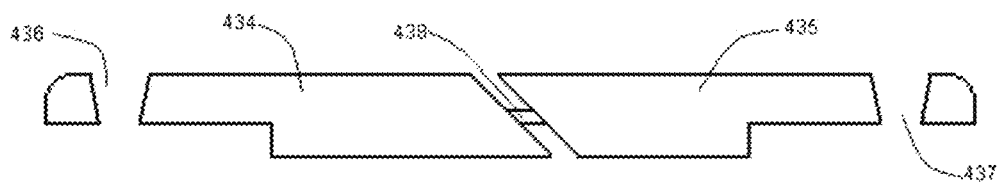
Figure 180:
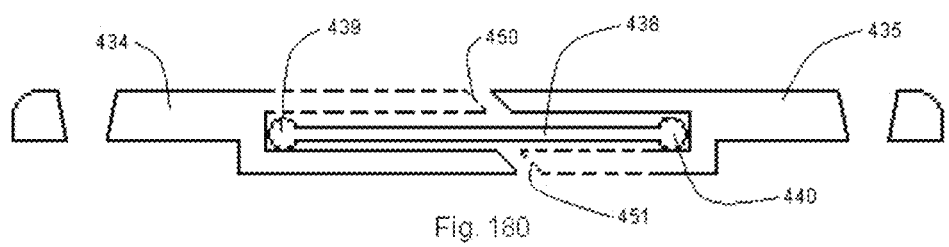
Figure 181:
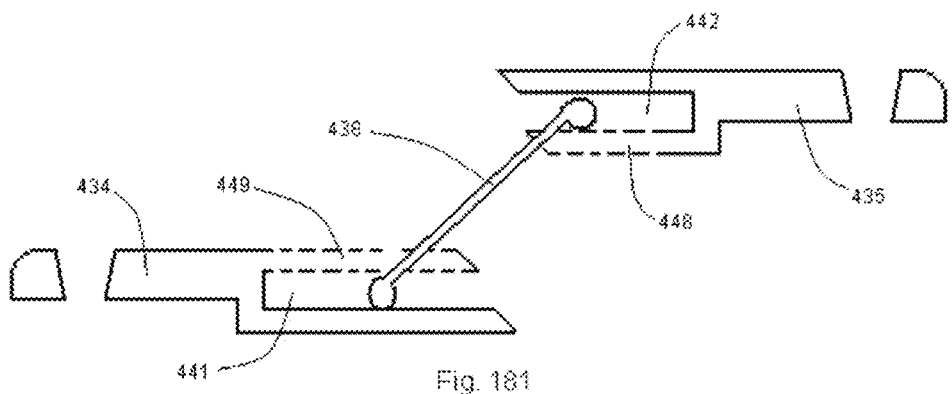
Figure 182:
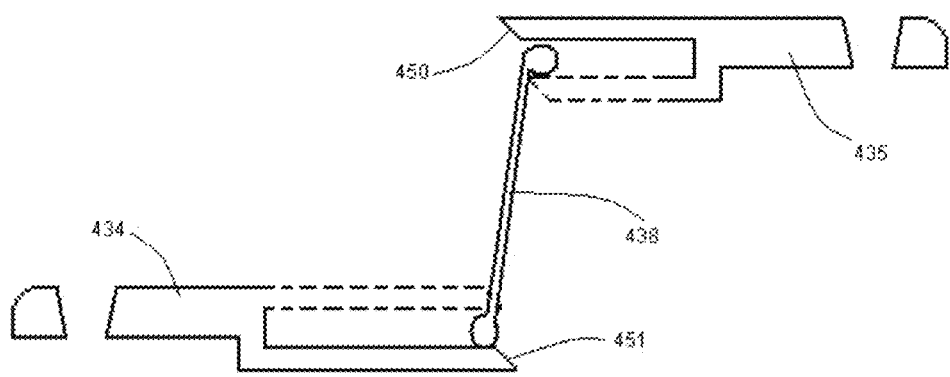

In another embodiment of the decompressive craniotomy device shown in FIGS. 176-182, the two heads 434 and 435 are linked by a sliding connector 438. The head 434 comprises a screw hole 436 for attachment to the skull and the head 435 comprises a screw hole 437 for attachment to the bone flap. Alternative embodiments can comprise of two or more screw holes at each head. The heads also comprise a hollow portion 441 and 442 which contains the sliding connector 438. The connector 428 has elongated ends 439 and 440 that engage with the hollow portions enlarged ends 434 and 444 and constrains the outward movement of the head 435 relative to head 434. The hollow portion also has hollow longitudinal extensions on both sides 445 and 446 that allow the sliding connectors enlarged ends 439 and 440 to slide inside the hollow portion. The head 435 hollow portion 442 has a longitudinal opening 448 on the top part and the head 434 hollow portion 441 has a longitudinal opening 449 on the bottom part. FIGS. 179-180 show the device with the heads 434 and 435 positioned together. The medial end of the head 435 is sloped 451 and the medial end of head 434 is also sloped 450 in the same direction. The sloped ends along with the solid parts of the hollow component encasing the sliding link prevent the head 434 from moving inwards beyond the head 435. FIG. 181 shows the device with the head 434 moved upwards relative to head 435 facilitated by the sliding link 438 and FIG. 182 shows the completely extended position of the device and the link. In an alternative embodiments, the sliding link 438 can be made of an elastomeric component or even a spring that can stretch and retract the heads back towards each other. The enlarged hollow portion is designed to be positioned inside the burr hole skull defect to provide a very low profile and avoid overlying skin irritation or erosion.

In another embodiment of the decompressive craniotomy device as illustrated in FIGS. 183-187, the sliding connector 457 comprises of multiple links 460 joined by hinges 461. The head 453 comprises a screw hole 455 for attachment to the skull and the head 454 comprises a screw hole 456 for attachment to the bone flap. The heads also comprise a hollow portion 441 and 442 which contains the sliding connector 438. The connector 428 has elongated ends 439 and 440 that engage with the hollow portions enlarged ends 434 and 444 and constrains the outward movement of the head 435 relative to head 434. The hollow portion also has hollow longitudinal extensions on both sides 445 and 446 that allow the sliding connectors enlarged ends 439 and 440 to slide inside the hollow portion. The head 435 hollow portion 442 has a longitudinal opening 448 on the top part and the head 434 hollow portion 441 has a longitudinal opening 449 on the bottom part. FIGS. 179-180 show the device with the heads 434 and 435 positioned together. The medial end of the head 435 is sloped 451 and the medial end of head 434 is also sloped 450 in the same direction. The sloped ends along with the solid parts of the hollow component encasing the sliding link prevent the head 434 from moving inwards beyond the head 435. FIG. 181 shows the device with the head 434 moved upwards relative to head 435 facilitated by the sliding link 438 and FIG. 182 shows the completely extended position of the device and the link. In an alternative embodiment, the sliding link 438 can be made of an elastomeric component or even a spring that can stretch and retract the heads back towards each other. The enlarged hollow portion is designed to be positioned inside the burr hole skull defect to provide a very low profile and avoid overlying skin irritation or erosion.

Figure 183:
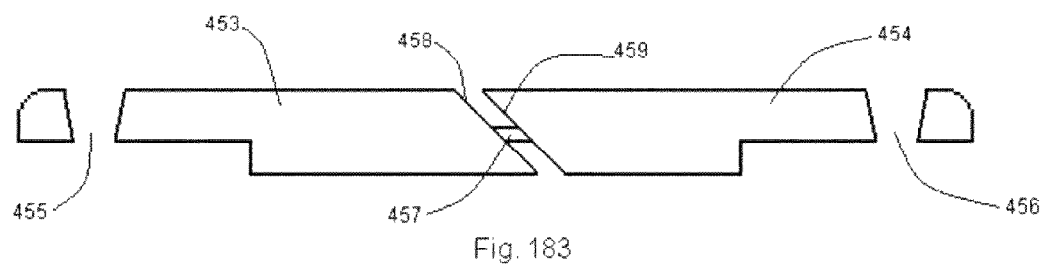
FIGS. 183 through 187 illustrate an exemplary cranial fixation device in accordance with an embodiment of the present invention.
Figure 184:
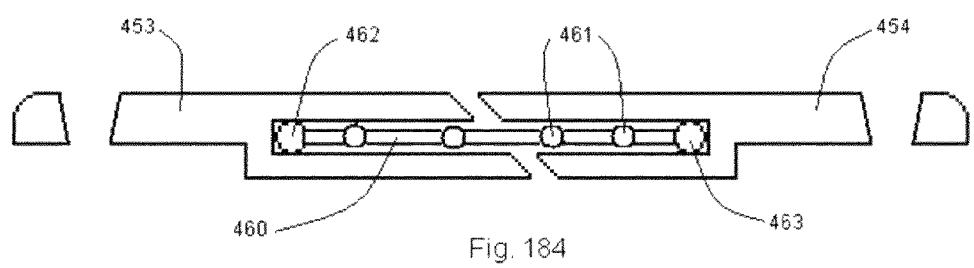
Figure 185:
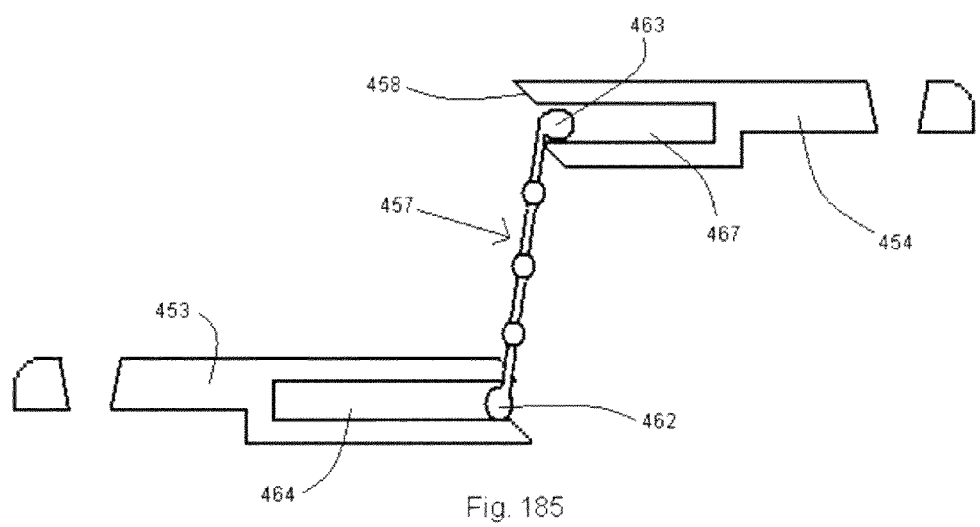
Figure 186:
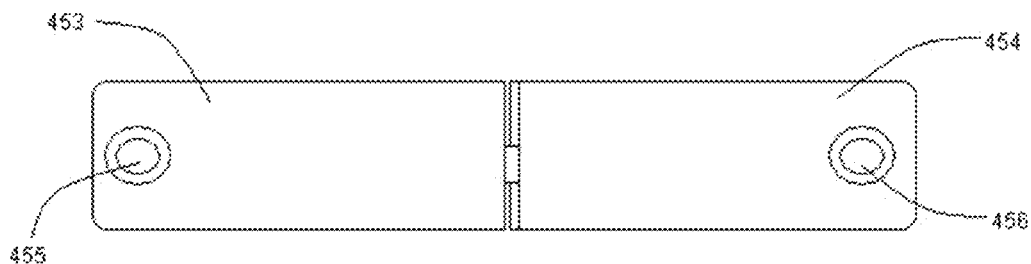
Figure 187:
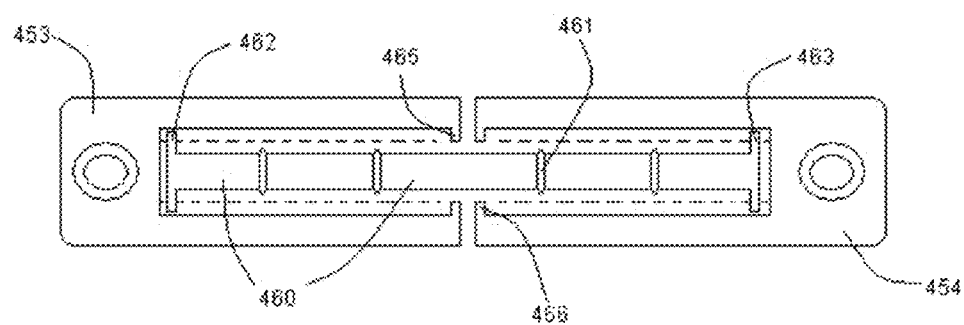

In another embodiment of the decompressive craniotomy device as illustrated in FIGS. 183-187, the sliding connector 457 comprises of multiple cross-links 460 joined by hinged connectors 461. The head 453 comprises a screw hole 455 for attachment to the skull and the head 454 comprises a screw hole 456 for attachment to the bone flap. The heads also comprise a hollow portion 464 and 467 which contains the sliding cross-links 457. The cross-links 457 have elongated ends 462 and 463 that engage with the hollow portions enlarged ends 465 and 466 and constrain the outward movement of the head 454 relative to head 453. The hollow portion also has hollow longitudinal extensions on both sides 467 and 468 that allow the sliding connectors enlarged ends 462 and 463 to slide inside the hollow portion. FIGS. 183-184 show the device with the heads 453 and 454 positioned together. The medial end of the heads is sloped 458 which prevent the head 454 from moving inwards beyond the head 453. FIG. 185 shows the device with the head 454 moved upwards relative to head 453 facilitated by the sliding cross-links 457.

Figure 188:
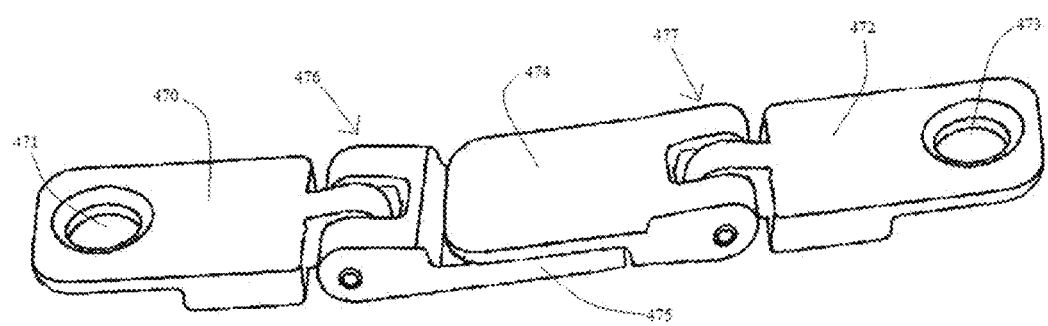
FIGS. 188 and 189 illustrate an exemplary cranial fixation device in accordance with an embodiment of the present invention.
Figure 189:
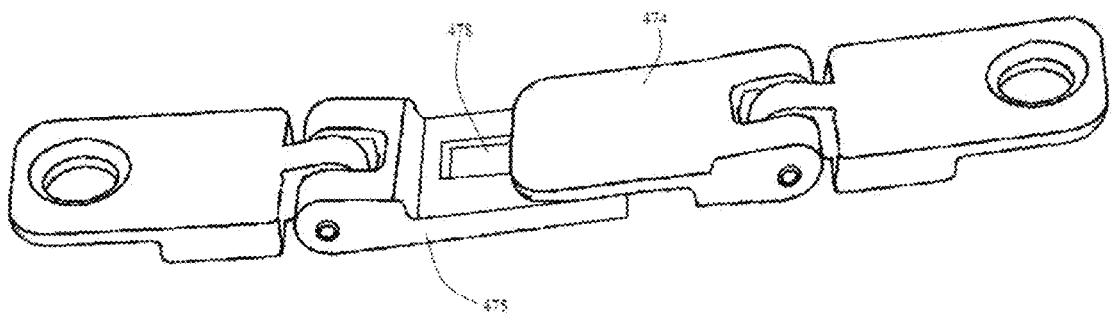
Figure 190:
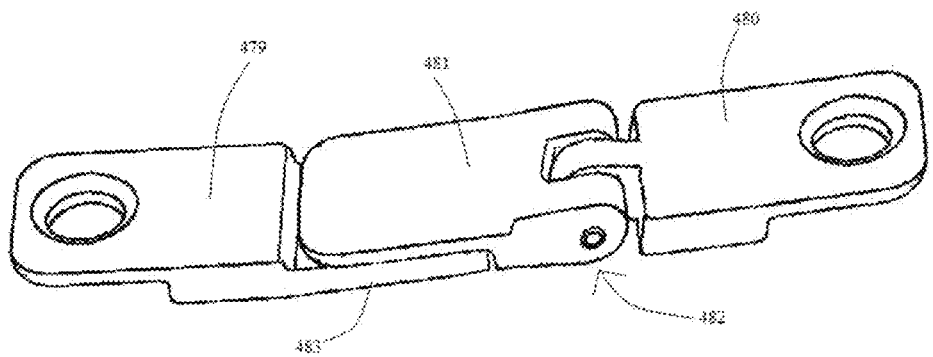
FIGS. 190 through 191*a* illustrate an exemplary cranial fixation device in accordance with an embodiment of the present invention.
Figure 191:
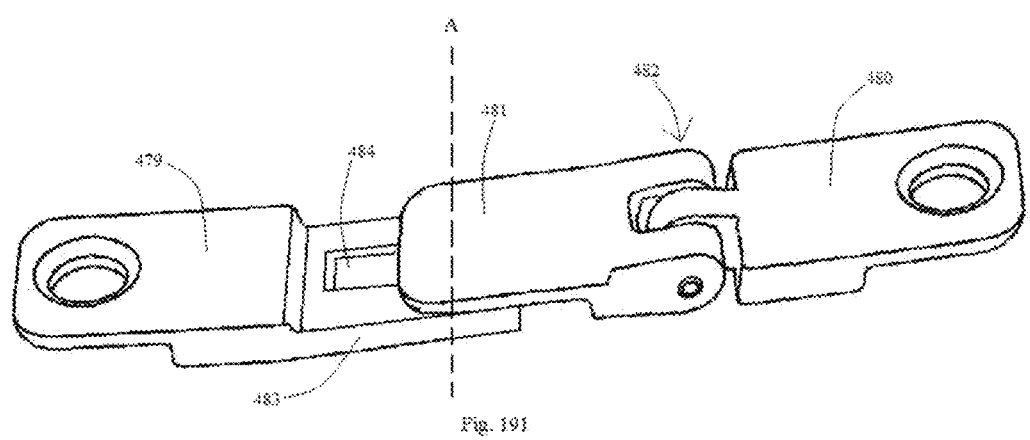
Figure 191A:
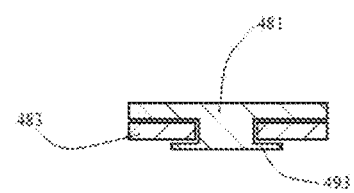
Figure 192:
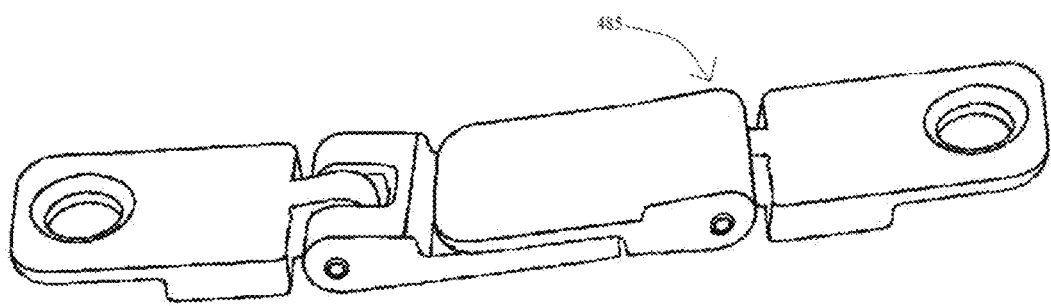
FIGS. 192 and 193 illustrate an exemplary cranial fixation device in accordance with an embodiment of the present invention.
Figure 193:
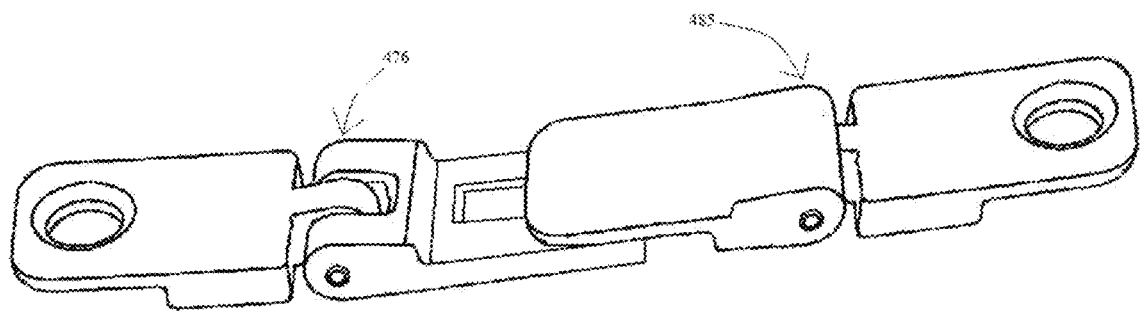
Figure 194:
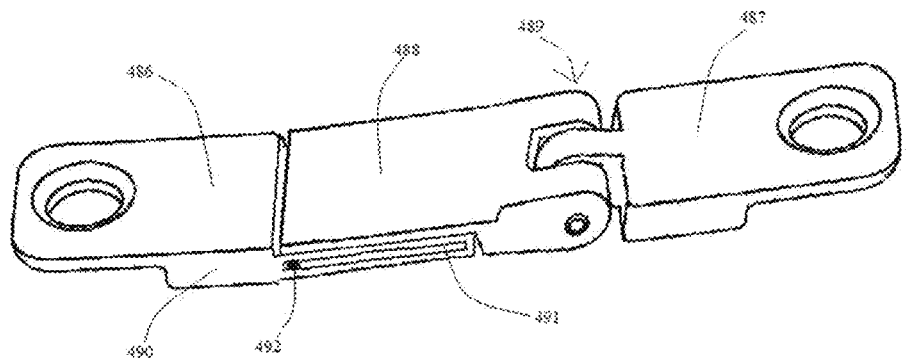
FIGS. 194 through 196 illustrate an exemplary cranial fixation device in accordance with an embodiment of the present invention.
Figure 195:
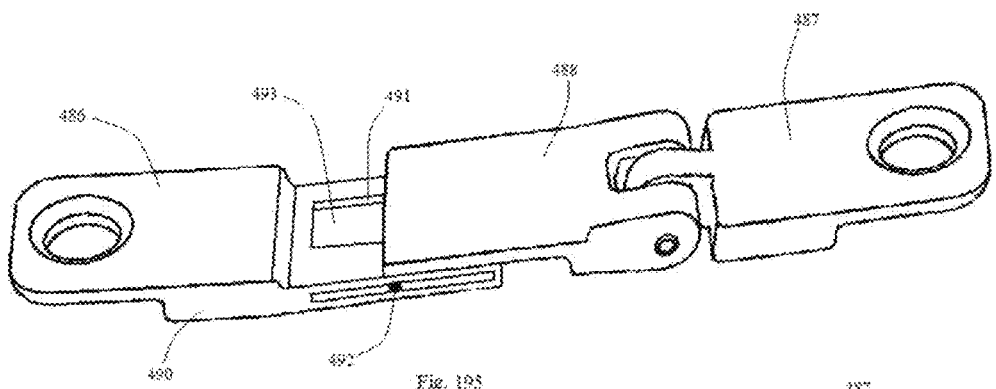
Figure 196:
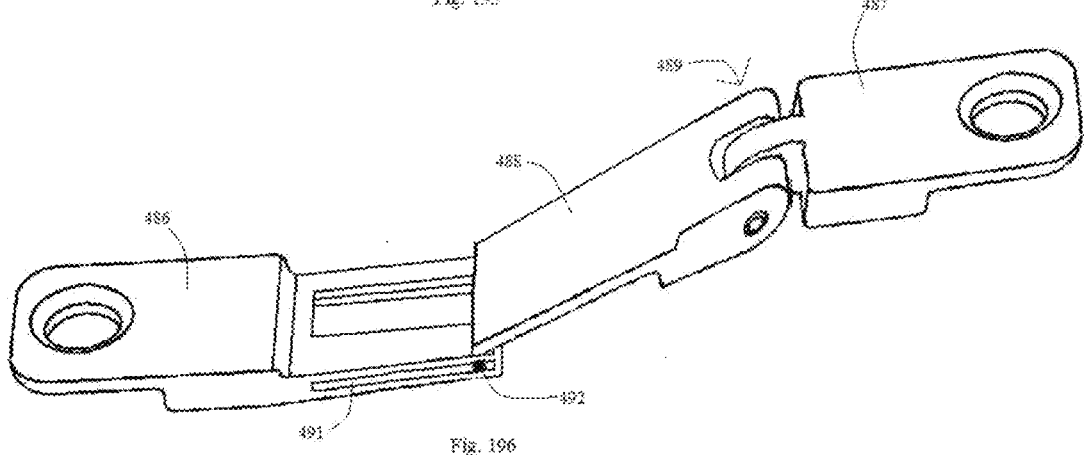
Figure 197:
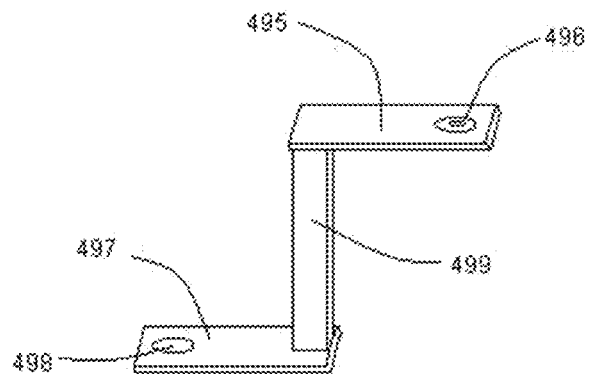
FIGS. 197 and 198 illustrate an exemplary cranial fixation device in accordance with an embodiment of the present invention.
Figure 198:
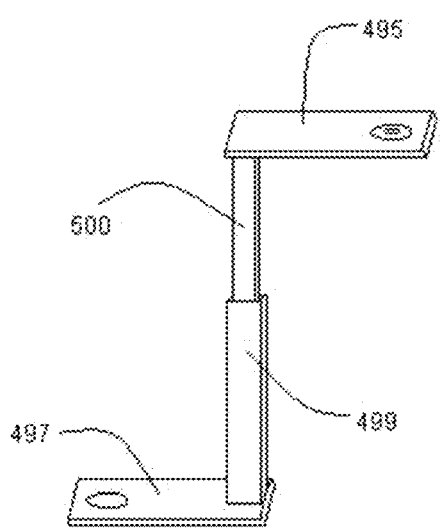

In other embodiments, the decompressive craniotomy device utilizes the sliding and hinge mechanisms in combination to move the two heads relative to each other and allows for a constrained outward bone flap movement in response to an elevated ICP. As shown in FIGS. 188 and 189, the head 470 comprises a bone screw hole 471 and the head 472 comprises a bone screw hole 473. The intermediate component linking the two heads comprises of extensions 475 and 474. The intermediate extension 474 is attached to the head 470 with a bidirectional hinge 476. The intermediate extension 474 is attached to the head 472 with a bidirectional hinge 477. The extensions 474 and 475 are slidably linked to each other with an opening 478 in extension 474 attached to the undersurface of extension 474. The heads are secured to the bone flap and skull with bone screws and the intermediate component can be placed in the burr hole skull defect for a more cosmetic and low profile fixation of the bone flap to the skull following a craniotomy. With an increase in ICP, the head 472 attached to the bone flap moves outwards relative to the head 470 attached to the skull. This outward movement of the head 472 is enabled by the hinges 477 and 476 as well as the extensions 474 and 475 sliding away from each other. The hinges 476 and 477 can also be unidirectional so as to not allow the head 472 to move inward beyond the position of the head 470. FIGS. 190-191a illustrate another embodiment of the device. The head 479 comprises an extension 483 and the head 480 is attached to the intermediate component 481 with a hinge 482. The sliding mechanism of the intermediate components 481 and 483 are shown in FIGS. 191 and 191a. The intermediate component 481 comprises of a T-shaped extension 493 in the middle that is slidably linked to the opening 484 in the extension 483. FIGS. 192 and 193 illustrate another embodiment of the device comprising of a unidirectional hinge 485 attached to one head and a bidirectional hinge 476 attached to the other head. In another embodiment as shown in FIGS. 194-196, the head 487 is attached to the intermediate component 488 with a hinge 489. The head 486 comprises an extension 490 that is slidably linked to the intermediate component 488. The extension 490 also comprises an opening in the middle 493 and openings one the side walls 491. The intermediate component 488 comprises an extension 492 at the end that slidably engages with the side wall opening 491. FIG. 194 shows the device in a retracted position with a normal ICP and the bone flap approximated to the skull. FIG. 196 illustrates the extended position of the two heads 487 and 486 relative to each other. The combination of the constrained sliding mechanism of the intermediate components 488 and 490 along with the hinge 489 allows the head 487 to move upwards relative to head 486 keeping the bone flap parallel to the skull. This outward movement of two heads staying parallel to each other allows a uniform outward movement of the bone flap in all directions rather than a fulcrum at the attached device end which would be seen with an isolated hinge without a sliding mechanism.

Figure 199:
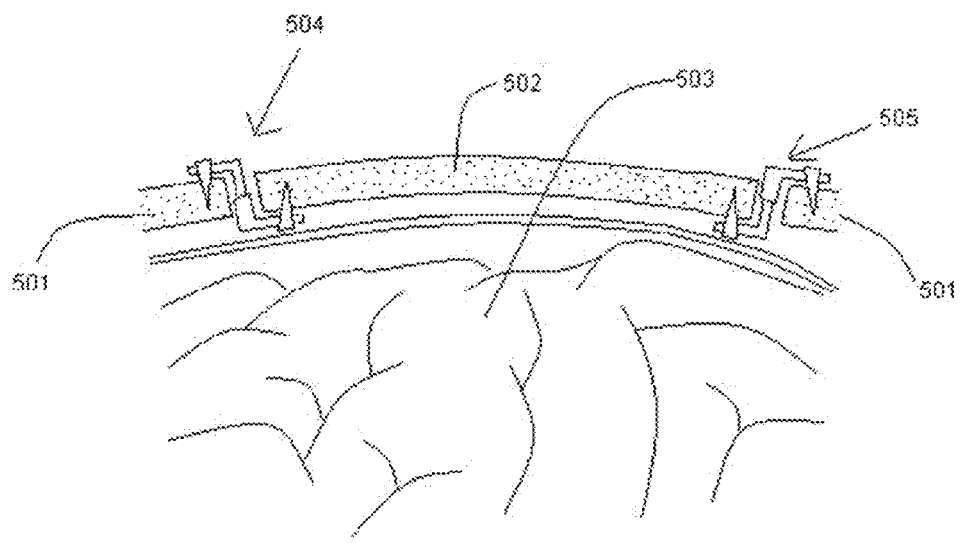
FIGS. 199 and 200 are cross sectional side views of exemplary cranial fixation devices attached to a skull and a bone flap for a decompressive craniotomy, in accordance with an embodiment of the present invention.
Figure 200:
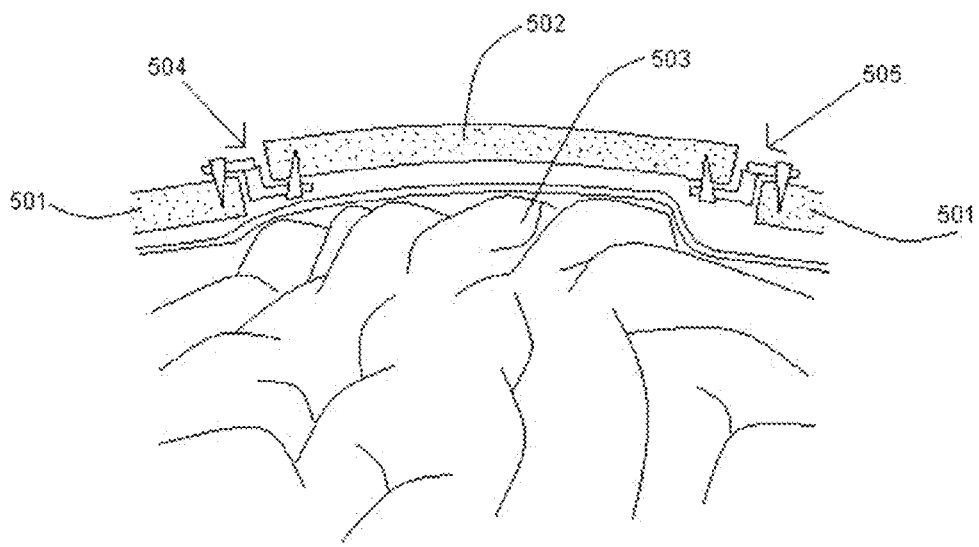

In another embodiment of the decompressive craniotomy device as shown in FIGS. 197-200, the head 495 comprises an extension 500 and a bone screw hole 496. The head 497 comprises an extension 499 and a bone screw hole 498. The extension 500 is telescopic and resides inside extension 499 when the heads are closer to each other. Following a craniotomy procedure, the bone flap 502 is positioned back into the skull with devices 504 and 505 in place. As shown in FIG. 199, the devices 504 and 505 approximate the bone flap 502 to the skull 501 when the telescopic extensions are in a distracted position. With an increase in ICP or brain swelling 503 as shown in FIG. 200, the bone flap 502 is pushed outward relative to the skull 501 to accommodate the swelling, placing the devices 504 and 505 telescopic extensions in a retracted position.

Figure 201:
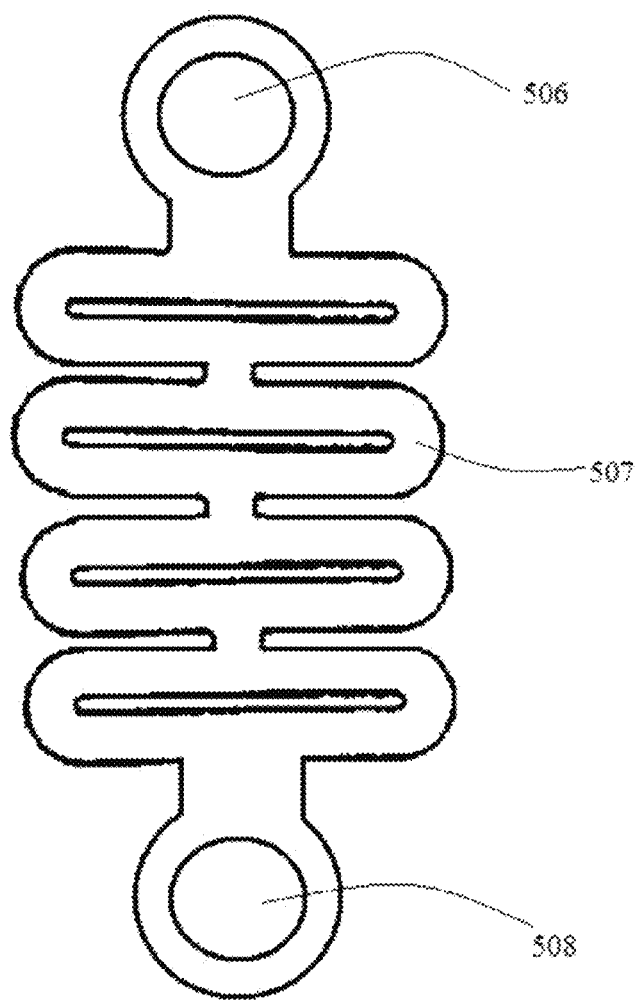
FIGS. 201 and 202 illustrate an exemplary cranial fixation device in accordance with an embodiment of the present invention.
Figure 202:
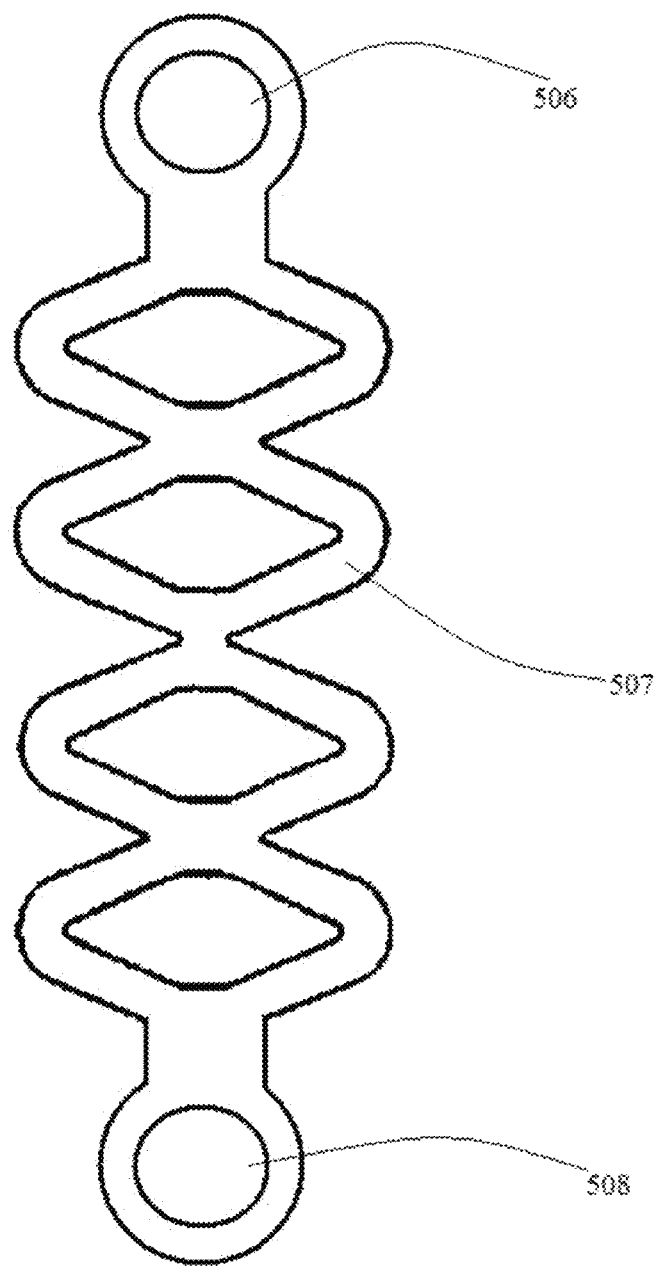
Figure 203:
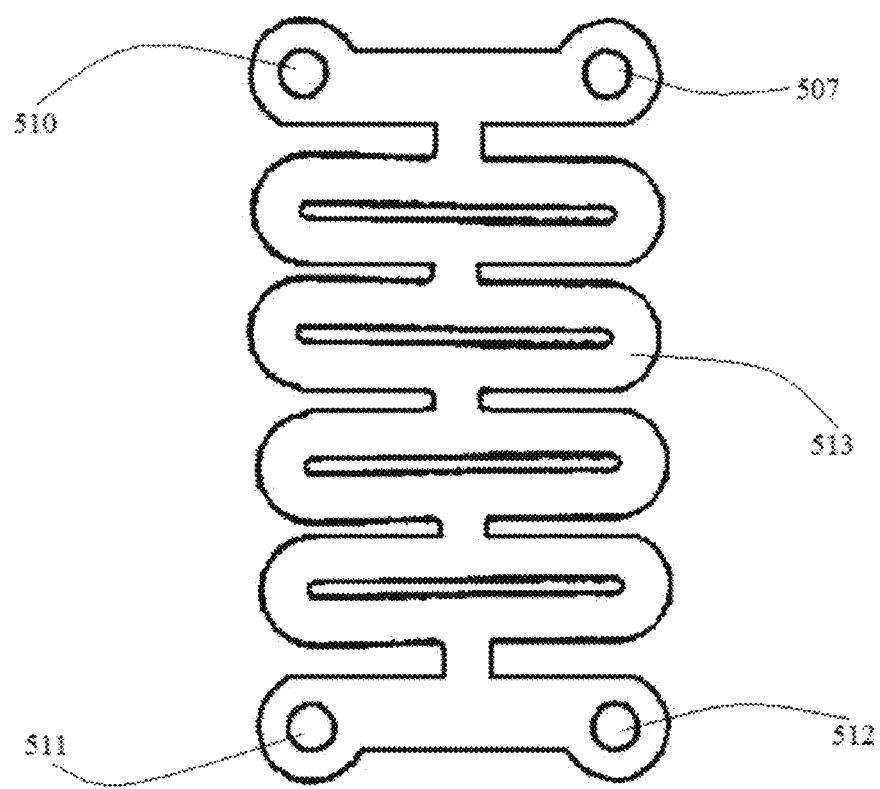
FIGS. 203 and 204 illustrate an exemplary cranial fixation device in accordance with an embodiment of the present invention.
Figure 204:
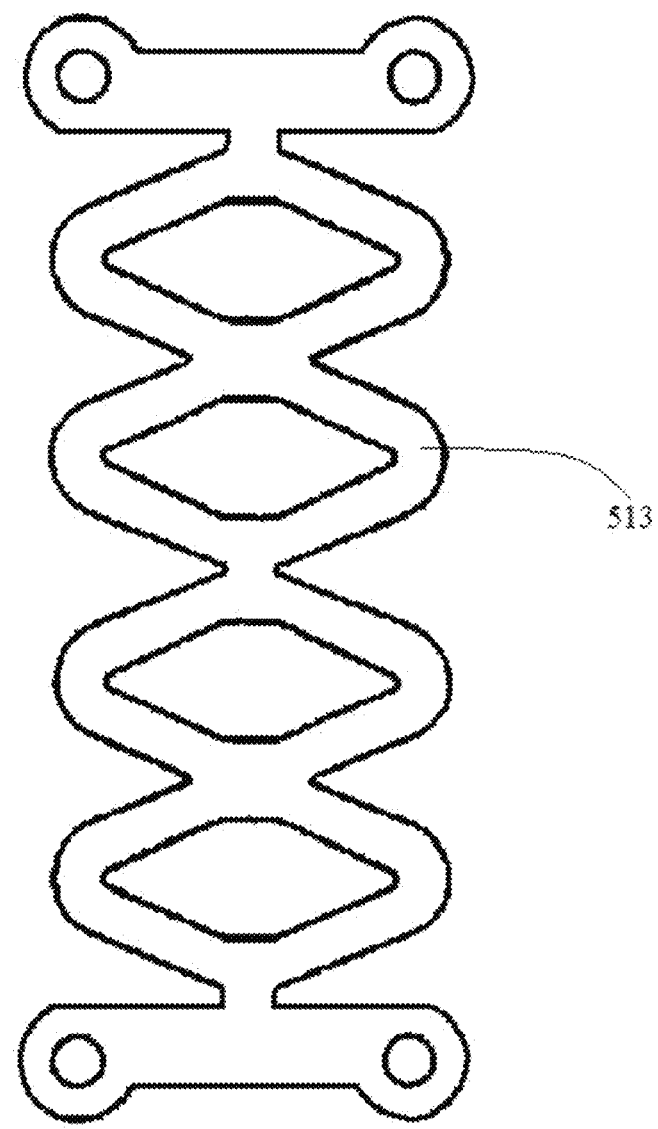
Figure 205:
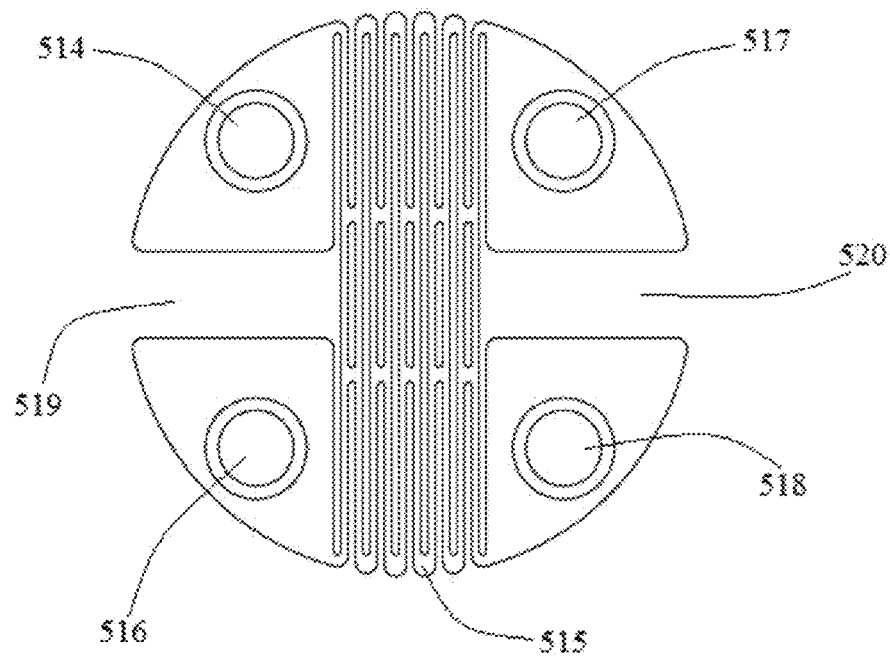
FIGS. 205 and 206 illustrate an exemplary cranial fixation device in accordance with an embodiment of the present invention.
Figure 206:
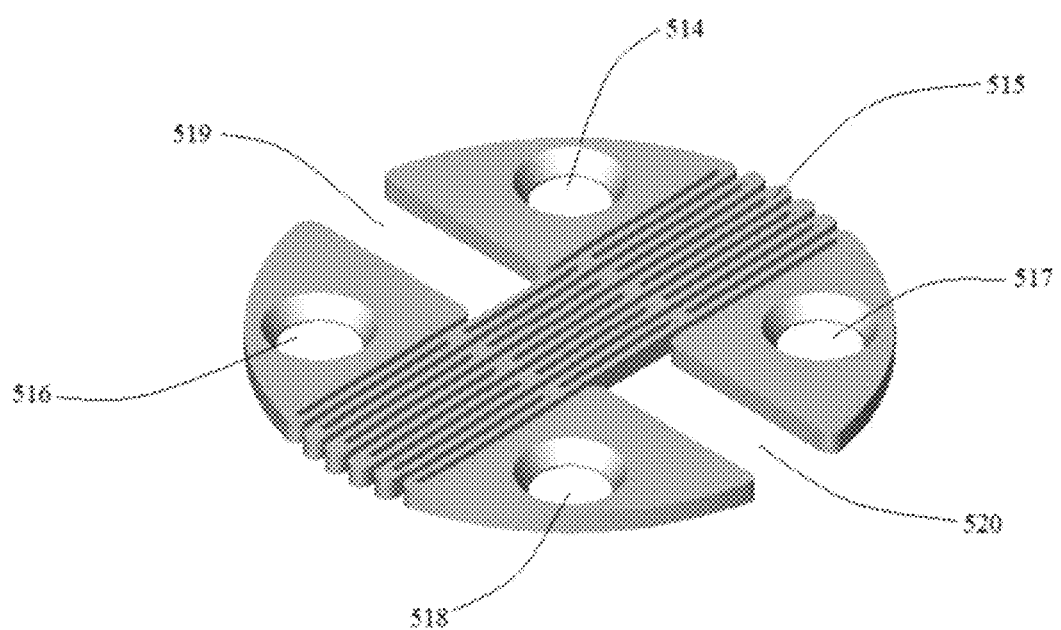

In another embodiment, the decompressive craniotomy device as shown in FIGS. 201 and 202 comprises a bone fastener hole 506 for attachment to the skull and a bone fastener hole 508 for attachment to the bone flap. The intermediate component 507 comprises a series of elastic tension spring members that expand or contract depending on the ICP and allow outward movement of the bone flap relative to the skull. FIG. 201 illustrates the contracted position of the intermediate component 507 and FIG. 202 illustrates the expanded position of the intermediate component 507. In another embodiment of the device as shown in FIGS. 203 and 204, the skull attachment portion comprises of two bone fastener holes 509 and 510 and the bone flap attachment portion also comprises of two bone fastener holes 511 and 512 with an intermediate component 513 shown in a contracted position in FIG. 204 and an expanded position in FIG. 205. In another embodiment as shown in FIGS. 205 and 206, the device comprises of anchor components with bone fastener holes 514 and 516 separated by a space 519 and anchor components with bone fastener holes 517 and 518 separated by a space 520. The anchor components 514 and 516 are connected with anchor components 517 and 518 by an intermediate component 515. The intermediate component 515 is comprised of a plurality of bridges that reversibly expand or contract dependent upon the pressure exerted on one anchor component versus the other. Ideally the bridges are designed to expand when the ICP exceeds 20-25 mm Hg and retract when the ICP is normal (<15-20 mmHg). The device can be formed from an integral metal sheet.

Figure 83:
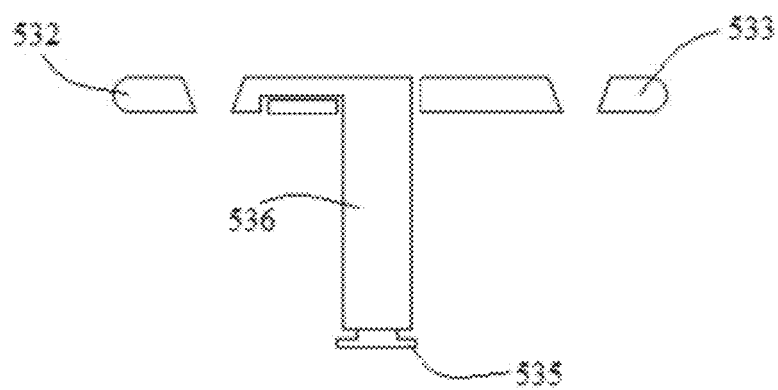
FIGS. 83 and 84 illustrate an exemplary cranial fixation device in accordance with an embodiment of the present invention.
Figure 84:
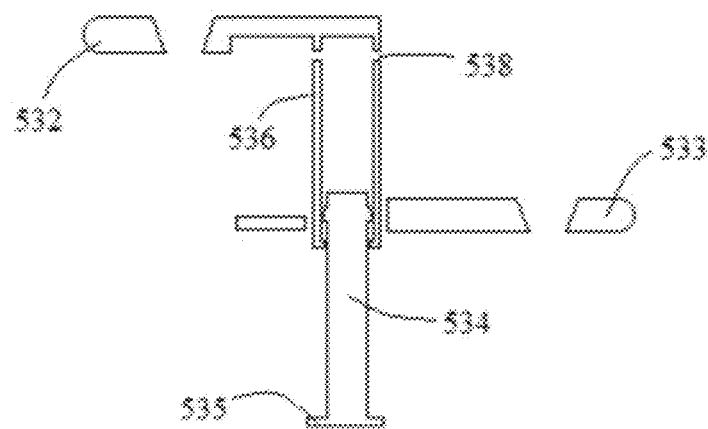
Figure 207:
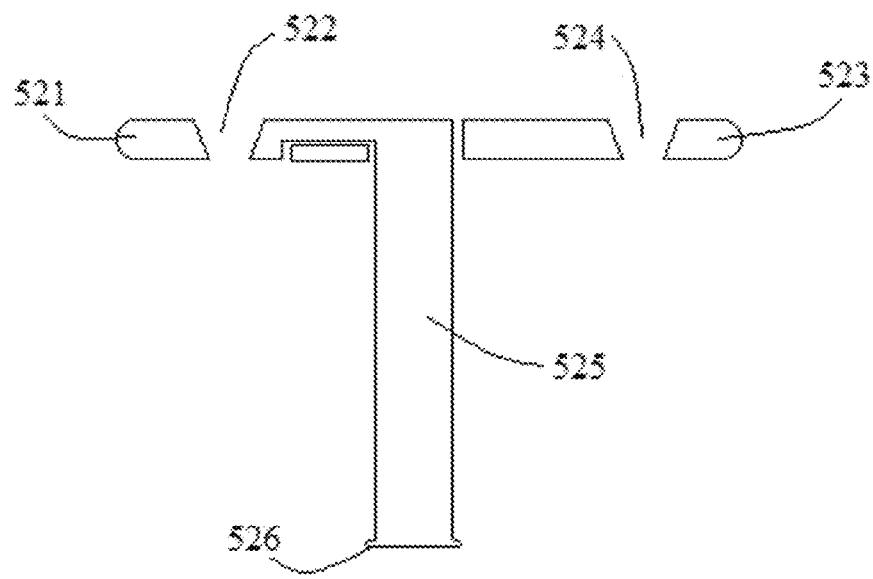
FIGS. 207 and 208 illustrate an exemplary cranial fixation device in accordance with an embodiment of the present invention.
Figure 208:
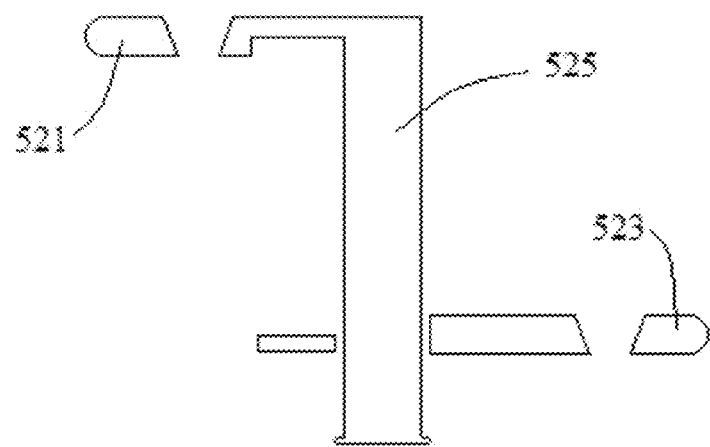
Figure 209:
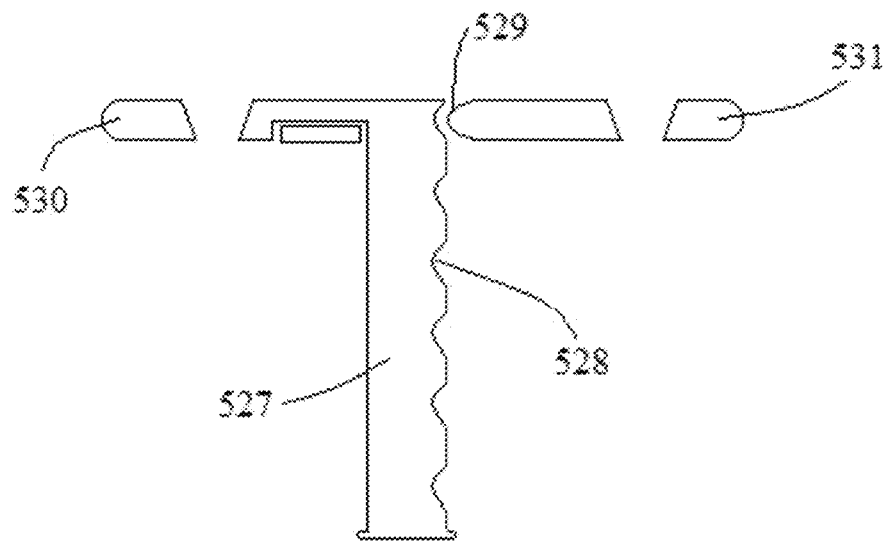
FIGS. 209 and 210 illustrate an exemplary cranial fixation device in accordance with an embodiment of the present invention.
Figure 210:
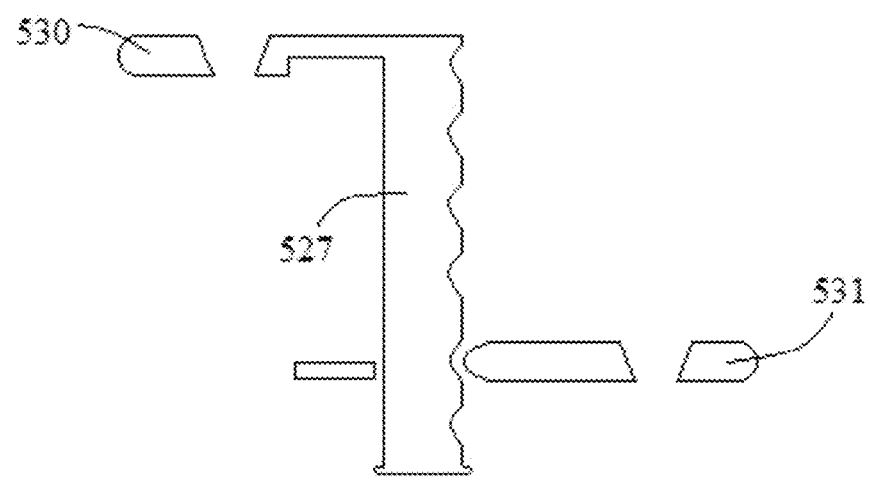
Figure 211:
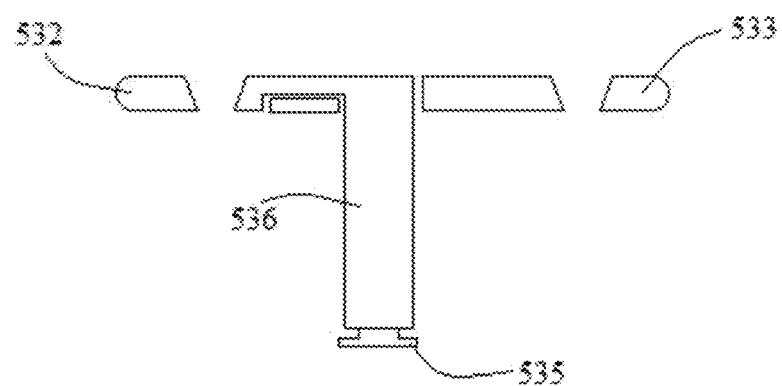
FIGS. 211 and 212 illustrate fixation device according to some embodiments of the invention.
Figure 212:
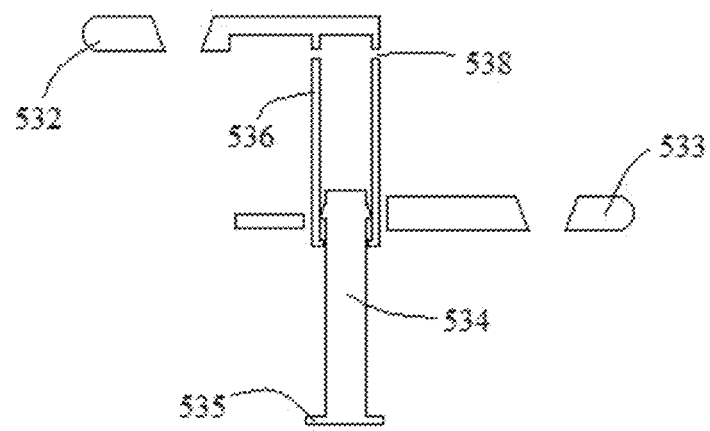

In another embodiment, the decompressive craniotomy device shown in FIGS. 207 and 208 comprises a head 521 with an extension 525 that is slidably connected to an opening in the head 523. The head 521 comprises a bone fastener hole 522 for attachment to the bone flap and the head 523 comprises a hone fastener hole 524 for attachment to the skull. When the ICP is normal, the two heads 521 and 523 are positioned next to each other with the extension 525 in the skull defect or burr hole as shown in FIG. 207. An increase in ICP pushes the bone flap as well as the head 521 outwards relative to head 523 attached to the skull. The extension 525 provides constrained outward movements of the two heads relative to each other. The wider distal portion 526 of the extension 525 prevents the extension 525 from completely pulling out from the opening in head 523. In another embodiment as shown in FIGS. 209 and 210, the device comprises a first head 530 with an extension 527 and a second head 531 with an opening for the extension 527. The head 531 opening is configured to contour the shape 529 that engages with recesses 528 in the extension 527. FIG. 209 shows the device in a retracted position and FIG. 210 shows the device in a distracted position. In another embodiment as shown in FIGS. 83 and 84, the device comprises a first head 532 with an extension 536 and a second head 533 with an opening for the extension 536. The extension 536 is telescopic and encloses another extension 534 to allow further distraction between the two heads. FIG. 209 shows the device in a retracted position and FIG. 210 shows the device in a distracted position.

In the various embodiments described herein the preferred head configuration is circular so as to cover the burr hole or skull opening. Other head configurations could be rectangular, square, X-shaped, fan shaped, or any other configuration able to connect the skull to the bone flap. Similarly, the telescopic configurations described are either cylindrical or rectangular and hollow designed to fit into the burr hole or skull opening. Other telescopic configurations could be partially solid, tapered, V-shaped or any other configuration that fit's the skull opening. The cranial fixation device can be made of titanium or titanium alloy for MRI imaging compatibility. It could also be made of a bio-absorbable material (polyesters, poly amino acids, polyanhydrides, polyorthoesters, polyurethanes, polycarbonates, homopolymers, copolymers of poly lactic acid and poly glycolic acid, copolyesters of e-caprolactone, trimethylene carbonate, and para-dioxanone), or allograft or xenograft bone that is absorbed by the body over time once the bone flap has fused with the skull. Alternatively, it could be made of a radiolucent material (polyetheretherketone), plastic, or a combination of plastic and metal to reduce CT and MRI imaging artifact.

Although the application for the cranial fixation device described in the various embodiments is for fixation of the bone flap to the skull following a craniotomy, it can also be used to cover a burr hole or skull fracture. Other applications include treatment of increased intracranial pressure following traumatic injury, subdural hemorrhage, epidural hemorrhage, subarachnoid hemorrhage, intra-ventricular hemorrhage, brain hemorrhage, ischemic stroke, hemorrhagic stroke, hypoxia, tumor, infection, brain swelling, and/or seizure. The heads positioned on the inner and outer surface of the skull and bone flap connected by a spring not only approximate the bone flap to the skull but can also allow external movement of the bone flap relative to the skull in case of an increased intracranial pressure. The external movement of the bone flap increases the intracranial space to accommodate the increase in intracranial pressure and provides for a decompressive craniectomy. Following normalization of the intracranial pressure, the bone flap is compressed back towards the skull by the spring or the elastomeric band and the two heads.

In cases of re-operation requiring removal of the bone flap, the cranial fixation device described in the various embodiments can be removed by simply distracting the two heads apart by pulling the head on the outer surface either manually or with an instrument.

The normal intracranial pressure is less than 20 mm Hg and with any brain swelling or hemorrhage the intracranial pressure can increase to greater than 20 mm Hg. With an increase in the intracranial pressure above the normal range, the cranial fixation devices are designed to disengage the locking mechanism and place the telescopic extensions into an extended position from a retracted position and therefore place the two heads apart, thereby allowing the bone flap to move outwards from the skull in a constrained manner and accommodate the higher intracranial pressure. Once the intracranial pressure reaches below 20 mm Hg again the telescopic extensions retract and position the bone flap downwards to the skull level.

In the various embodiments described herein the preferred head configuration is either circular or semi-circular coming together in a circular shape when the telescopic extensions are in a compressed position. The circular shape covers the burr hole skull defect. Other head shapes can include oval, rectangular, square, semi-oval, C-shape, L-shape, T-shape, X-shape, Y-shape, Z-shape, fan shaped or any other configuration able to connect the skull to the bone flap. Similarly, the telescopic configurations described are either cylindrical or rectangular and hollow designed to fit into the burr hole or skull opening. Other telescopic configurations could be partially solid, tapered, V-shaped or any other configuration that fit's the skull opening. The cranial fixation device can be made of titanium or titanium alloy for MRI imaging compatibility. It could also be made of a bioresorbable (polyesters, poly amino acids, polyanhydrides, polyorthoesters, polyurethanes, polycarbonates, homopolymers, copolymers of poly lactic acid and poly glycolic acid, copolyesters of e-caprolactone, trimethylene carbonate, and para-dioxanone), or allograft, or xenograft bone that is absorbed by the body over time once the bone flap has fused with the skull. Alternatively, it could made of a radiolucent material like polyetheretherketone (PEEK) or polyaryletherketone (PEAK), high molecular weight polyethylene, carbon fiber, polyurethane, plastic, or a combination of plastic and metal to reduce CT and MRI imaging artifact. The cranial fixation device discussed herein can be of unitary construction, such that the heads and telescopic portions can be integral or formed from a single piece material. Alternative embodiments contemplate that the components of the cranial fixation device can be non-integral, and can be attached to and/or coupled to other components of the device. The thickness of the heads can range from 0.3 mm to 20 mm. The size of the head can range from 6 mm to 40 mm. The length of the telescopic portion in a retracted position can range from 5 mm to 20 mm and in an extended position can range from 10 mm to 60 mm. The length of the screws can range from 4 mm to 20 mm. The expandable material of the intermediate components in some embodiments may be made of various different materials such as, but not limited to, silicone, rubber, ethylene propylene compounds, flourocarbon, polyurethane, titanium, other metal components designed to reversibly expand and/or contract, etc. The expandable intermediate component of the cranial fixation device is typically capable of reversibly expanding from 1 to 1.000% of its contracted size. While the above-mentioned size range of the device components reflects the preferred embodiments, other embodiments can comprise of head, telescope, and screw sizes outside of the aforementioned ranges. The angulations of the telescopic component in the preferred embodiment are 90 degrees relative to the heads but could any other angle from perpendicular to parallel to the head.

Although the application for the cranial fixation device described in the present embodiment is for fixation of the bone flap to the skull following a craniotomy and to provide for a decompressive craniotomy to treat increased ICP, cranial fixation devices according to various embodiments of the preset invention may be used to treat ICP resulting from various different causes such as, but not limited to, traumatic injury, subdural hemorrhage, epidural hemorrhage, subarachnoid hemorrhage, intra-ventricular hemorrhage, brain hemorrhage, ischemic stroke, hemorrhagic stroke, hypoxia, tumor, infection, brain swelling, or seizure, etc. Moreover, some embodiments may be used in different types of applications including, but not limited to, covering a burr hole, repairing a skull fracture, treating congenital cranial skull defects such as, but not limited to, craniosynostosis, etc.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Having fully described at least one embodiment of the present invention, other equivalent or alternative methods of providing an expandable fixation device according to the present invention will be apparent to those skilled in the art. The invention has been described above by way of illustration, and the specific embodiments disclosed are not intended to limit the invention to the particular forms disclosed. For example, the particular implementation of the anchor portions may vary depending upon the particular type of item on which the anchor portions are to be attached. The anchor portions described in the foregoing were directed to cranial implementations that attach to the skull; however, similar techniques are to provide expandable fixation devices with various different types of anchor portions for use in different areas of the anatomy such as, but not limited to, ribs, vertebrae, other bones, soft tissue, etc. Non-cranial implementations of the present invention are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. A method comprising the steps of:
removing a bone flap from a skull bone;
joining a first portion of a fixation device to outer surface of the skull bone;
joining a second portion of the fixation device to the outer surface of the bone flap;
operatively connecting the first portion and the second portion of the fixation device with an elastomeric band, which is connected to both an upper surface of the first portion and an upper surface of the second portion externally to the fixation device;
responding to changes in intracranial pressure by moving the fixation device upwardly and downwardly; and
constraining the downwardly movement of the bone flap from moving inward beyond the outer surface of the skull bone, wherein medial edges of the first portion and of the second portion are sloped and overlap each other to not allow the second portion from moving inward beyond the first portion.

2. The method of claim 1, wherein the step of joining the first portion of the fixation device to the skull bone includes the step of using at least one bone fastener component, and wherein the step of joining the second portion of the fixation device to the bone flap includes the step of using at least one bone fastener component.

3. The method of claim 1, wherein the fixation device includes a couple of telescopic extensions, each of which is connected to the first portion or the second portion.

4. The method of claim 1, wherein the fixation device includes at least one housing operatively connected to the intermediate portion enabling upwardly and downwardly movement in response to variations of the intracranial pressure while preventing the bone flap from moving inward beyond the outer surface of the skull.

5. A craniotomy method comprising the steps of:
providing a fixation device, the device including a first portion, a second portion, a first bone fastener portion, a second bone fastener portion operatively joined to the first bone fastener portion forming an intermediate portion, the intermediate portion being moveable upwardly and downwardly to accommodate change in intracranial pressure;
removing a bone flap from a skull bone;
joining the first portion of the fixation device to the skull bone;
joining the second portion of the fixation device to the bone flap, wherein the second portion is operatively connected to the first portion with an elastomeric band, which is connected to both an upper surface of the first portion and an upper surface of the second portion externally to the fixation device;
constraining the downward movement of the bone flap from moving inward beyond an outer surface of the skull bone, wherein medial edges of the first portion and of the second portion are sloped and overlap each other to not allow the second portion from moving inward beyond the first portion.

6. The method of claim 5, wherein the fixation device includes at least one housing operatively connected to the intermediate portion enabling upwardly and downwardly movement in response to variations of the intracranial pressure while preventing the bone flap from moving inward beyond the outer surface of the skull.

7. The method of claim 5, wherein the fixation device includes a couple of telescopic extensions, each of which is connected to the first portion or the second portion.

8. A craniotomy method comprising the steps of:
providing at least one fixation device, the device including a first portion, a second portion, a first bone fastener portion, a second bone fastener portion operatively joined to the first bone fastener portion forming an intermediate portion, the intermediate portion being moveable upwardly and downwardly to accommodate changes in intracranial pressure;
removing a bone flap from a skull bone;
joining the first portion of a fixation device to an outer surface of the skull bone;
joining the second portion of the fixation device to an outer surface of the bone flap, wherein the second portion is operatively connected to the first portion with an elastomeric band, which is connected to both an upper surface of the first portion and an upper surface of the second portion externally to the fixation device, wherein medial edges of the first portion and of the second portion are sloped and overlap each other to not allow the second portion from moving inward beyond the first portion to constrain the bone flap when moving downward from moving inward beyond the outer surface of the skull bone.

9. The method of claim 8, wherein the fixation device includes a couple of telescopic extensions, each of which is connected to the first portion or the second portion.

* * * * *